(12) United States Patent
Cheruvallath et al.

(10) Patent No.: US 7,381,736 B2
(45) Date of Patent: Jun. 3, 2008

(54) THIAZOLE AND THIADIAZOLE INHIBITORS OF TYROSINE PHOSPHATASES

(75) Inventors: Zacharia S. Cheruvallath, San Diego, CA (US); Colin J. Loweth, San Diego, CA (US); Ruth F. Nutt, Santa Fe, NM (US); Darryl Rideout, San Diego, CA (US); Joseph E. Semple, San Diego, CA (US); Jing Wang, San Diego, CA (US); Feiyue Wu, Poway, CA (US); Shankari Mylvaganam, San Diego, CA (US); Hengyi Zhu, San Diego, CA (US); Jianzhong Sun, San Diego, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 0 days.

(21) Appl. No.: 11/219,402

(22) Filed: Sep. 2, 2005

(65) Prior Publication Data

US 2006/0194768 A1    Aug. 31, 2006

Related U.S. Application Data

(60) Provisional application No. 60/642,292, filed on Jan. 6, 2005, provisional application No. 60/638,447, filed on Dec. 22, 2004, provisional application No. 60/607,034, filed on Sep. 2, 2004.

(51) Int. Cl.
*A61K 31/427* (2006.01)
*C07D 277/18* (2006.01)

(52) U.S. Cl. .................. 514/370; 548/202; 548/193

(58) Field of Classification Search ............... 514/370; 548/202, 190, 193
See application file for complete search history.

(56) References Cited

U.S. PATENT DOCUMENTS

| | | | |
|---|---|---|---|
| 3,710,795 A | 1/1973 | Higuchi et al. |
| RE28,819 E | 5/1976 | Thompson |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 5,033,252 A | 7/1991 | Carter |
| 5,052,558 A | 10/1991 | Carter |
| 5,323,907 A | 6/1994 | Kalvelage |
| 5,348,969 A | 9/1994 | Romine et al. |
| 5,378,803 A | 1/1995 | Morgan et al. |
| 5,480,874 A | 1/1996 | Shoji et al. |
| 5,502,032 A | 3/1996 | Haupt et al. |
| 5,654,322 A | 8/1997 | Hirata et al. |
| 5,705,145 A | 1/1998 | Miklean et al. |
| 5,709,874 A | 1/1998 | Hansen et al. |
| 5,733,882 A | 3/1998 | Carr et al. |
| 5,759,542 A | 6/1998 | Gurewich |
| 5,840,674 A | 11/1998 | Yatvin et al. |
| 5,860,957 A | 1/1999 | Jacobsen et al. |
| 5,900,252 A | 5/1999 | Calanchi et al. |
| 5,948,433 A | 9/1999 | Burton et al. |
| 5,972,366 A | 10/1999 | Haynes et al. |
| 5,983,134 A | 11/1999 | Ostrow |
| 5,985,307 A | 11/1999 | Hanson et al. |
| 5,985,317 A | 11/1999 | Venkateshwaran et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |
| 6,048,736 A | 4/2000 | Kosak |
| 6,060,082 A | 5/2000 | Chen et al. |
| 6,071,495 A | 6/2000 | Unger et al. |
| 6,120,751 A | 9/2000 | Unger |
| 6,131,570 A | 10/2000 | Schuster et al. |
| 6,139,865 A | 10/2000 | Friend et al. |
| 6,167,301 A | 12/2000 | Flower et al. |
| 6,174,874 B1 | 1/2001 | Wang et al. |
| 6,256,533 B1 | 7/2001 | Yuzhakov et al. |
| 6,261,595 B1 | 7/2001 | Stanley et al. |
| 6,267,983 B1 | 7/2001 | Fujii et al. |
| 6,271,359 B1 | 8/2001 | Norris et al. |
| 6,274,552 B1 | 8/2001 | Tamarkin et al. |

(Continued)

FOREIGN PATENT DOCUMENTS

| | | |
|---|---|---|
| EP | 1115729 B1 | 7/2001 |
| EP | 1452530 A1 | 9/2004 |
| JP | 62244059 | 10/1987 |
| JP | 06161014 | 6/1994 |
| JP | 06306089 | 11/1994 |

(Continued)

OTHER PUBLICATIONS

U.S. Appl. No. 11/814,239, filed Jul. 18, 2007, Cheruvallath et al.
Abdelrazek et al. "Nitriles in heterocyclic synthesis: synthesis of 2-substituted 4-phenylthiazoles from phenacyl thiocyanate" J. Chem. Res. Synop. vol. 8, pp. 246-247, 1985.

(Continued)

*Primary Examiner*—Kamal A. Saeed
*Assistant Examiner*—Yong Chu
(74) *Attorney, Agent, or Firm*—Saliwanchik, Lloyd & Saliwanchik

(57) ABSTRACT

Compounds and compositions are provided for modulating the activity of protein tyrosine phosphatases. In one embodiment, the compounds and compositions are thiazoles and thiadiazoles that inhibit the activity of protein tyrosine phosphatase 1B.

19 Claims, No Drawings

U.S. PATENT DOCUMENTS

| | | |
|---|---|---|
| 6,316,652 B1 | 11/2001 | Steliou |
| 6,486,141 B2 | 11/2002 | Lau et al. |
| 6,486,142 B2 | 11/2002 | Leblanc et al. |
| 6,498,151 B2 | 12/2002 | Li et al. |
| 6,583,126 B2 | 6/2003 | Leblanc et al. |
| 6,777,433 B2 | 8/2004 | Leblanc et al. |
| 6,784,205 B2 | 8/2004 | Wiesmann et al. |
| 7,094,794 B2 | 8/2006 | Petry et al. |
| 7,115,624 B1 | 10/2006 | Andersen et al. |
| 7,163,932 B2 | 1/2007 | Dufresne et al. |
| 7,169,797 B2 | 1/2007 | Xin et al. |
| 2002/0058644 A1 | 5/2002 | Leblanc et al. |
| 2002/0072516 A1 | 6/2002 | Liu et al. |
| 2002/0169157 A1 | 11/2002 | Liu et al. |
| 2003/0064979 A1 | 4/2003 | Hansen et al. |
| 2003/0114703 A1 | 6/2003 | Leblanc et al. |
| 2004/0138255 A1 | 7/2004 | Huang et al. |
| 2004/0167187 A1 | 8/2004 | Saunders et al. |
| 2004/0167188 A1 | 8/2004 | Xin et al. |
| 2004/0176330 A1 | 9/2004 | Dufresne et al. |
| 2004/0191926 A1 | 9/2004 | Zhang et al. |
| 2004/0214870 A1 | 10/2004 | Xin et al. |
| 2005/0065118 A1 | 3/2005 | Wang et al. |
| 2005/0065196 A1 | 3/2005 | Inaba et al. |
| 2005/0119332 A1 | 6/2005 | Jeppesen et al. |
| 2006/0030544 A1 | 2/2006 | Hangauer, Jr. et al. |
| 2006/0135483 A1* | 6/2006 | Cheruvallath et al. ........ 514/92 |
| 2006/0135488 A1 | 6/2006 | Lee et al. |
| 2006/0135773 A1 | 6/2006 | Semple et al. |
| 2006/0142250 A1 | 6/2006 | Blaskovich et al. |
| 2006/0194768 A1 | 8/2006 | Cheruvalath et al. |
| 2006/0281802 A1 | 12/2006 | Choi et al. |

FOREIGN PATENT DOCUMENTS

| | | |
|---|---|---|
| JP | 07112975 | 5/1995 |
| JP | 07149745 | 6/1995 |
| JP | 08208632 | 8/1996 |
| JP | 10120512 | 5/1998 |
| JP | 11302177 | 11/1999 |
| JP | 2002114768 A2 | 4/2002 |
| JP | 2002105065 | 10/2002 |
| JP | 2003335680 | 11/2003 |
| WO | WO 93/19054 | 9/1993 |
| WO | WO 94/13695 | 6/1994 |
| WO | WO 96/20689 | 7/1996 |
| WO | WO 97/41097 | 11/1997 |
| WO | WO 98/08871 | 3/1998 |
| WO | WO 98/27108 | 6/1998 |
| WO | WO 99/01423 | 1/1999 |
| WO | WO 99/03861 | 1/1999 |
| WO | WO 99/19300 | 4/1999 |
| WO | WO 99/19313 | 4/1999 |
| WO | WO 99/32098 | 7/1999 |
| WO | WO 00/15229 | 3/2000 |
| WO | WO 00/15230 | 3/2000 |
| WO | WO 00/17211 | 3/2000 |
| WO | WO 00/25780 | 5/2000 |
| WO | WO 00/45635 | 8/2000 |
| WO | WO 01/44226 | 6/2001 |
| WO | WO 01/46206 | 6/2001 |
| WO | WO 01/70753 | 9/2001 |
| WO | WO 02/36116 | 5/2002 |
| WO | WO 03/015777 | 2/2003 |
| WO | WO 03/032916 A | 4/2003 |
| WO | WO 03/037328 | 5/2003 |
| WO | WO 03/041729 | 5/2003 |
| WO | WO 2004/002480 | 1/2004 |
| WO | WO 2004/029040 | 4/2004 |
| WO | WO 2004/041799 | 5/2004 |
| WO | WO 2004/050646 | 6/2004 |
| WO | WO 2004/063147 | 7/2004 |
| WO | WO 2004/065374 | 8/2004 |
| WO | WO 2004/071448 | 8/2004 |
| WO | WO 2004/099192 | 11/2004 |
| WO | WO 2004/101568 | 11/2004 |
| WO | WO 2005/011685 | 2/2005 |
| WO | WO 2005/012280 | 2/2005 |
| WO | WO 2005/035551 | 4/2005 |
| WO | WO 2005/044277 | 5/2005 |
| WO | WO 2005/047898 | 5/2005 |
| WO | WO 2005/081954 | 9/2005 |
| WO | WO 2005/081960 | 9/2005 |
| WO | WO 2005/097773 | 10/2005 |
| WO | WO 2005/116003 | 12/2005 |
| WO | WO 2006/009876 | 1/2006 |
| WO | WO 2006/017124 | 2/2006 |
| WO | WO 2006/044531 | 4/2006 |
| WO | WO 2006/050097 | 5/2006 |
| WO | WO 2006/050212 | 5/2006 |
| WO | WO 2006/055525 | 5/2006 |
| WO | WO 2007/009911 | 1/2007 |
| WO | WO 2007/081755 | 7/2007 |

OTHER PUBLICATIONS

Abou-Gharbia, et al., "Synthesis and Structure Activity Relationship of Substituted Tetrahydro-and Hexahydro-1, 2-benzisothiazol-3-one, 1, 1-Dioxides and Thiadiazinones: Potential Anxiolytic Agents" J. Med. Chem., 1989, 32, pp. 1024-1033.

Acharya, et al., "Surface-mediated solid phase reactions: a simple, efficient and base-free synthesis of phosphonates and phosphates on Al2O3" Process Technology Development Division.

Ahima, et al., "Appetite Suppression and Weight Reduction by a Centrally Active Aminosterol", Diabetes, vol. 51, Jul. 2002. pp. 2099-2104.

Ahmad, et al., "Synthesis of novel benzofuran isoxazolines as protein tyrosine phosphatase 1B inhibitors", Bioorganic & Medicinal Chemistry Letters, vol. 16, 2006, pp. 2139-2143.

Akiyama, et al., "A1Cl3-N, N-Dimethylaniline: A new Benzyl and Allyl Ether Cleavage Reagent", Tetrahedron Letters, vol. 32, No. 10, pp. 1321-1324, 1991.

Ala, et al., "Structural Insights into the design of Nonpeptidic Isothiazolidinone-containing Inhibitors of Protein-tyrosine Phosphatase 1B", Journal of Biological Chemistry, Dec. 8, 2006, vol. 281, No. 49, pp. 38013-38021.

Ala, et al., "Structural Basis for inhibition of Protein-tyrosine Phosphatase 1B by Isothiazolidinone Heterocyclic Phosphonate Mimetics", Journal of Biological Chemistry, Oct. 27, 2006, vol. 281. No. 43, pp. 32784-32795.

Alcaraz, et al. "Novel N-Aryl and N-heteroaryl sulfamide Synthesis via palladiu Cross Coupling", Organic Letters, 2004, vol. 6, No. 16, pp. 2705-2708.

Andersen, et al., "A Genomic perspective on protein tyrosine phophatases: gene structure, pseudogenes, and genetic disease linkage", The FASEB Journal, vol. 18, 2004, pp. 8-30.

Andersen, et al., "Discovery and SAR of a Novel Selective and Orally Bioavaliable Nonpeptide Classical Competitive Inhibitor Class of protein-tyrosine Phosphatase 1B", J. Med. Chem., 2002, vol. 45, pp. 4443-4459.

Anderie, et al., "Direct interaction between ER membrane-bound PTP1B and its plasma membrane-anchored targets", Cellular Signaling, vol. 19, 2007, pp. 582-592.

Andersen, et al., "2-(Oxalylamino)-Benzioc Acid is a general, Competitive Inhibitor of protein-tyrosine phosphatases", J. of Biol. Chem., vol. 275, No. 10, pp. 7101-7108, 2000.

Aronov, et al., "Synthesis and structure-activity relationships of adenosine analogs as inhibitors of trypanosomal glyceraldehyde-3-phosphate dehydrogenase. Modifications at positions 5' and 8" Bioorganic & Medicinal Chemistry Letters, vol. 8, 1998, pp. 3505-3510.

Asante-Appiah, et al., "Conformation-assisted Inhibition of Protein-tyrosine phosphatase-1B Elicites Inhibitor Selectivity over T-cell Protein-tyrosine Phosphatase" The Journal of Biological Chemistry, vol. 281, No. 12, pp. 8010-8015, Mar. 24, 2006.

Asante-Appiah, et al., "Protein Tyrosine phosphatase: the quest for negative regulators of insulin action" Am. J. Physiol. Endocrinol Meta., vol. 284, pp. E663-E670, 2003.

Baird, et al., "The preparation and rearrangement of 1-prenylindoles and 3-prenylindolenines", Heterocycles, vol. 15, No. 2, 1981, pp. 713-717.

Banwell, et al., "Palladium-Catalyzed Cross-Coupling and Related Reactions Involving Pyrroles", Eur, J. Org. Chem., 2006, pp. 3043-3060.

Barford, et al., "Crystal Structure of Human Protein Tyrosine Phosphatase 1B", Science Mar. 11, 1994, vol. 263, No. 5152, pp. 1397-1404.

Barford, et al. "Purification and Crystallization of the Catalytic Domain of human Protein Tyrosine Phosphatase 1B Expressed in *Escherichia coli*" J. Mol. Biol., 1994, 239, pp. 726-730.

Barr, et al., "Crystal Structure of Human Protein Tyrosine Phosphatase 14 (PTPN14) at 1.65-A Resolution", Proteins: Structure, Function, and Bioinformatics, vol. 63, pp. 1132-1136, 2006.

Bartholomew, et al., "Regulation of the catalytic activity of PTP1B: Roles for cell adhesion, tyrosine residue 66, and proline residues 309 and 310", Experimental cell Research, vol. 311, 2005, pp. 294-306.

Barton, et al. "The Chemistry of Pentavalent Organobismuth Reagents. Part 7, The Possible Role of Radical Mechanisms in the Phenylation Process for Bismuth (v), and Related Lead (IV), Iodine (iii), and Antimony (V) Reagents", J. Chem. Society, Perkin Trans, 1987, pp. 241-249.

Bashford, et al., "N-H Insertion reactions of rhodium carbenoids. Part 3. The development of a modified Bischler indole synthesis and a new protecting-group strategy for indoles", J. Chem. Soc. Perkin Trans., vol. 1, 2002, pp. 1672-1687.

Bashford, et al. "A new protecting-group strategy for indoles" Tetrahedron Letters, vol. 43, 2002, pp. 135-137.

Basuki, et al. "Enhancement of Insulin signaling pathway in adipocytes by oxovanadium (IV) complexes", ScienceDirect, Biochemical and Biophysical Research Communications, vol. 349, 2006, pp. 1163-1170.

Behrman, et al., "Reactions of Phosphonic Acid Esters with Nucleophiles. I. Hydrolysis", J. Org. Chemistry, vol. 35. No. 9, 1970, pp. 6063-6069.

Bence, et al., "Neuronal PTP1B regulates body weight, adiposity and leptin action", Nature Medicine, 2006, pp. 1-8.

Bennett, et al., "Organometallic and Organometalloidal Fluorine Compounds. Part VII. Triflurormethyl Compounds of Phosphorus", Nature, 1950, pp. 1565-1571.

Bento, et al., "Association of Protein Tyrosine Phosphatase 1B Gene Polymorphisms with type 2 Diabetes", Diabetes, vol. 53, 2004, pp. 3007-3012.

Berger, "A Rapid Convenient Reduction of Indoles to Indolines and of Tetrahydrocarbazoles to Hexahydrocarbazoles by Trimethylamine/Borane" Communications, 1974, pp. 508-510.

Bergstrom, et al., "Synthesis and Characterization of a New Fluorine Substituted Nonionic Dinucleoside Phosphonate Analogue, P-Deoxy-P-(difluoromethyl) thymidylyl (3'-5) thymidine", J. Org. Chem., 1988, vol. 53, pp. 3953-3958.

Bernard, et al., "New Rearrangement reactions as revealed in decomposition of 3-benzyl-3-cyanoindazole", Tetrahedron Letters, No. 44, pp. 4529-4532, 1972.

Berti, et al. "Stereospecfic Reduction of 3-Hydroxy-3H-indoles and of their Corresponding N-Oxides with NaBH4 and LiAiH4. Synthesis of True 1-Hydroxy-2, 3-disubstituted Indoles. Crystal and Molecular Structure of 3-Hydroxy-2, 3-diphenylindoline" JCS Perkins, II, pp. 339-346.

Bhagwat et al., "phenyl 4-phenyl-2-thiazolyl diketones" J. Indian Chem. Soc., vol. 45, pp. 270-272, 1968.

Bhat, et al., "The total synthesis of (-)Dihydroaszonalenin and the stereochemistry of aszonalenin", Tetrahedron Letters, vol. 27, No. 48, pp. 5873-5874, 1986.

Bialy, et al., "Inhibitors of Protein Tyrosine Phosphatases: Next Generation Drugs", Angew Chem. Int. Ed., 2005, 44, vol. 3814-3839.

Biomol Drug Discovery News, "SIRT1: A New Target for Cancer", pp. 1-3.

Bishop, et al., "A Gatekeeper Residue for inhibitor sensitization of protein tyrosine phophatases", Bioorganic & Medicinal Chemistry Letters, vol. 16, 2006, pp. 4002-4006.

Bjorge, et al., "Identification of Protein-tyrosine Phosphatase 1B as the Major Tyrosine Phosphatase Activity Capable of Dephosphorylating and activating c-Src in Several Human Breast Cancer Cell Lines", vol. 275, No. 52, pp. 41439-41446, 2000.

Blackburn, et al. "Trifluoromethylphosphinyl Bis-Triazolides in the synthesis of trifluoromethylphosphonate Analogs of Nucleotides" Tetrahedron Letters, vol. 34, No. 1, pp. 149-152, 1993.

Bolm, et al. "Palladium-Catalyzed N-Arylation of Sulfoximines with Aryl Bromides and Aryl Iodies", J. Org. Chem., 2000, vol. 65, pp. 169-175.

Boutselis, et al., "Synthesis and Cell-Based Activity of a Potent and Selective Protein Tyrosine Phosphatase 1B Inhibitor Prodrug", 2006, Journal of Medicinal Chemistry, pp. A-I.

Braselton et al. "Gas Chromatographic and Mass Spectral Properties of Sulfonylurea N-Methyl-N'-perfluoracyl Derivatives" Analytical Chemistry, 1976, pp. 1386-1394, vol. 48 No. 9.

Brazil, Melanie "Outside the site: A lateral approach to phosphatase inhibition", Research Highlights, Drug Metabolism, Sep. 2004, vol. 3, pp. 736. www.nature.com/reviews/drugdis.

Brondel, et al. "New Strategy for the synthesis of phosphatase inhibitors TMC-69-6H and analogs", Tetrahedron Letters, vol. 47, 2006, pp. 9305-9308.

Brown-Shimer et al., "Effect of Protein Tyrosine Phosphatase 1B Expression on Transformation by the Human Neu Oncogene", Cancer Res., vol. 52, pp. 478-482, 1993.

Brunet, et al., "One Scientist's Quest for The Origin of our Species", News Focus, Nov. 29, 2002, vol. 298, Science, pp. 1708-1711.

Burke, et al., "Potent Inhibition of Insulin Receptor Dephosphorylatin by a Hexamer Peptide Containing the phosphotyrosyl Mimetic F2Pmp", vol. 204, No. 1, 1994, pp. 129-134.

Burke, et al. Synthesis of 4-phosphono(difluromethyl)-D, L-phenylalanine and N-Boc and N-Fmoc Derivatives Suitably Protected for Solid-Phase Synthesis of Nonhydrolyzable Phosphotyrosyl Peptide Analogues., Tetrahedron Letters, vol. 34, No. 26, pp. 4125-4128, 1993.

Burke, et al., "Small Molecule Interactions with Protein-Tyrosine Phosphatase PTP1B and their use in Inhibitor Design", Biochemistry, 1996, vol. 35, pp. 15989-15996.

Burke, et al., "Phosphoryltyrosyl Mimetics in the design of Peptide-based signal transduction inhibitors", Biopolymers (Peptide Science), vol. 60, pp. 32-44.

Burton, et al. "Allylation of [(Diethoxyphosphinyl) difluoromethyl]zinc Bromide as a Convenient Route to 1, 1-Difluoro-3-alkenephosphates" J. Organic Chem., 1989, vol. 54, pp. 613-617.

Burton, et al., "A Facile Synthesis of Trifluoromethane- and Pentafluorobenzenephosphonates", Aug. 1979, Communications.

Business Wire, May 25, 2006, "Ceptyr, Inc. Begins IND-Enabling Studies with Its PTP-1B Inhibitor for Type II Diabetes".

Calbiochem, Cat No. 475950, Monoperoxo (picolinato) oxovanadate (V), Nov. 1997.

Calbiochem, Cat No. 203695 Potassium Bisperoxo (1, 10-phenanthroline) oxovanadate (V), Feb. 2006.

Calis, et al., "Synthesis and Anticonvulsant Activity of Some New 4-Aryl-4-imidazoline-2-one Derivatives", Drug. Res., vol. 42, (9I), No. 5, 1992, pp. 592-594.

Casara, et al. "Synthesis of Acid Stable 5'O-Fluoromethyl Phosphonates of Nucleosides Evaluation as Inhibitors of Reverse Transcriptase" Bioorganic & Medicinal Chemistry Letters, vol. 2, No. 2, pp. 145-148, 1992.

Casini, et al., "Carbonic Anhydrase Inhibitors: Inhibition of Cytosolic Isozymes I and II with Sulfamide Derivatives" Bioorganic & Medicinal Chemistry Letters, vol. 13, 2003, pp. 837-840.

Casnati, et al., "Electrophilic Substitution in Indoles: Direct Attack at the 2-position of 3-alkylindoes", Tetrahedron Letters, No. 52, pp. 5277-5280, 1972.

Catt, et al. "Trifluoroacetic Acid Cleavage of N-tert-Butylamides. A New Synthesis of Primary Sulfamides", J. Org. Chem., vol. 39, No. 4, 1974, pp. 566-568.

Chan, et al., "Iridium (III) Hydride Complexes for the Catalytic Enantioselective Hydrogenation of Imines", J. Am. Chem. Soc., 1990, vol. 112, pp. 9400-9401.

Charbonneau, et al., "Human Placenta protein-tyrosine phoshatase: Amino acid sequence and relationship to a family of receptor-like protein", Proc. Natl Acad. Sci, vol. 86, pp. 5252-5256, 1989.

Cho, et al., "Direct and indirect reductive amination of aldehydes and ketones with solid acid-activated sodium borohydide under solvent-free conditions", Tetrahedron, vol. 61, 2005, pp. 5725-5734.

Chemical Abstract #1001:286133 corresponding to JP2002114768.
Chemical Abstract #119:28002 corresponding to DE4127152.
Chemical Abstract #121:241670 corresponding to JP06161014.
Chemical Abstract #133:309911 corresponding to DE19918297.
Chemical Abstract #136:294822 corresponding to JP2002105065.
Chemical Abstract #1988:195893 corresponding to JP62244059.
Chemical Abstract #1995:767402 corresponding to JP06306089.
Chemical Abstract #1995:867676 corresponding to JP07149745.
Chemical Abstract #1995:896167 corresponding to JP07112975.
Chemical Abstract #1996:666870 corresponding to JP08208632.
Chemical Abstract #1998:287418 corresponding to JP10120512.
Chemical Abstract #1999:699078 corresponding to JP11302177.
Chemical Abstract #2003:918699 corresponding to JP2003335680.

Chen, et al. "Why is Phosphonodifluoromethyl Phenylalanine a more potent inhibitory moiety than phosphonomethyl phenylalanine toward protein-tyrosine phophatases?", Biochemical And Biophysical research Communications, vol. 216, No. 3, 1995, pp. 976-984.

Chen, et al., "Effects of SOV-induced phosphatase inhibition and expression of protein tyrosine phosphatases in rat corneal endothelial cells", Experimental Eye Research, vol. 81, 2005, pp. 570-580.

Cheng, et al., "Coordinated action of protein tyrosine phosphatases in insulin signal transduction" Eur. J. Biochem., vol. 269, pp. 1050-1059, 2002.

Cheon, et al., "Discovery of a Novel Protein Tyrosine phosphatase-1B, KR61639: potential development as an antihyperglycemic agent" European Journal of Pharmacology, vol. 485, 2004, pp. 333-339.

Cho, et al., "PTP-1B inhibitors: Cyclopental [d] [1, 2]-oxazine derivatives", Bioorganic & Medicinal Chemistry, Letters, vol. 16, 2006, pp. 499-502.

Chong, et al., "Effect of rosuvastatin on hepatic production of apolipoprotein B-containing lipoproteins in an animal model of insulin resistance and metabolic dyslipidemia", Atherosclerosis, vol. 185, 2006, pp. 21-31.

Chernoff, et al., "Cloning of a cDNA for a major human protein-tyrosine-phosphatase", Proc. Natl Acad. Sci, vol. 87, pp. 2735-2739, 1990.

Ciranni, et al. "Vanadium Salts induce Cytogenetic effects in in vivo treated mice", Mutation Research, vol. 343, 1995, pp. 53-60.

Clampit, et al., "Reduction of Protein-tyrosine Phosphatase-1B increases insulin signaling in FAO hepatoma cells", Biochem. Biophys. Res. Commun, Jan. 10, 2003, vol. 300, No. 92, pp. 261-267.

Clark, et al., "Sulfamic Acids As Protein Tyrosine Phosphatase Inhibitors", poster.

Clark, et al., "Synthesis and Antiviral activity of 2'deoxy-2-fluoro-2-C-methyl purine nucleosides as inhibitors of hepatitis C virus RNA replication", Bioorganic & Medicinal Chemistry Letters, vol. 16, 2006, pp. 1712-1715.

Cohen, et al., "Modular Binding Domains in Signal Transduction Proteins" Cell, vol. 80, pp. 234-248, 1995.

Combs et al. "Protein Structure-Based Design of Combinatorial Libraries: Discovery of Non-Peptide Binding Elements to Src SH3 Domain" J. Am. Chem. Soc., vol. 118, pp. 287-288, 1996.

Combs, et al., "Potent Benzimidazole Sulfonamide Protein Tyrosine Phosphatase 1B Inhibitors Containing the Heterocyclic (S)-Isothiazolidinone phosphotyrosine Mimetic" J. Med. Chem, 2006, vol. 49, pp. 3774-3789.

Combs, et al., Supporting Information "Potent Benzimidazole Sulfonamide Protein Tyrosine Phosphatase 1B Inhibitors Containing the Heterocyclic (S)-Isothiazolidinone phosphotyrosine Mimetic", S1-S4.

Combs, et al., "Structure-Based Design and Discovery of Protein Tyrosine Phosphatase Inhibitors Incorporating novel Isothiazolidinone Heterocyclic Phosphotyrosine Mimetics", J. Med. Chem., 2005, vol. 48, pp. 6544-6548.

Combs, et al., Supporting Information "Structure-Based Design and Discovery of Protein Tyrosine Phosphatase Inhibitors Incorporating novel Isothiazolidinone Heterocyclic Phosphotyrosine Mimetics", pp. S1-S22.

Coskun, et al., "Reactivity of Benzylic Acylammonium chlorides. A Novel method for the synthesis of N-Phenacylamides." Synthetic Communications. vol. 27, No. 1, pp. 1-9, 1997.

Crawley, et al., "Concise Approach to Novel Isothiazolidinone Phosphotyrosine Emetics: Microwave-Assisted Addition of Bisulfite to Activated Olefins", Organic Letter, 2005, vol. 7, No. 22, pp. 5067-5069.

Crawley, et al., Supporting Information "Concise Approach to Novel Isothiazolidinone Phosphotyrosine Memetics: Microwave-Assisted Addition of Bisulfite to Activated Olefins", Discovery Chemistry, Incyte Corporation, 2005, pp. S1-S6.

Cromlish, et al., "Development and Validation of an Intact Cell Assay for Protein Tyrosine Phosphatases Using Recombinant Baculoviruses", Biochemical pharmacology, vol. 58, pp. 1539-1546, 1999.

Cui, et al., "Protein tyrosine phosphatase 1B inhibitors from Morus root bark", Bioorganic & Medicinal Chemistry Letters, vol. 16, 2006, pp. 1426-1429.

Darnell, et al., "Jak-Stat Pathways and Transcriptional Activation in Response to IFN's and Other Extracellular Signaling Proteins", Science, vol. 364, pp. 1415-1421, 1994.

Dean, et al., "Chronic Treatment with IDD-3, a Novel PTP1B Inhibitor, Results in Sustained Improvements in Glucose homeostasis in ob/ob an ddb/db Mice", 516-P, pp. A122.

Den Hertog, et al. "Receptor protein tyrosine phosphatase a activates pp60c-src and is involved in neuronal differentiation" EMBO J., vol. 12, pp. 3789-3798.

Ding, et al., "Parallel synthesis of 5-cyano-6-aryl-2-thiouracil derivatives as inhibitors for hepatitis C viral NS5B RNA-dependent RNA polymerase", Bioorganic Chemistry, vol. 34, 2006, pp. 26-38.

Drebin, et al., "Monoclonal antibodies specific for the neuoncogene product directly mediate anti-tumor effects in vivo" Oncogene2, pp. 387-394, 1988.

Dube, et al., "Involvement of the small protein tyrosine phosphatases TC-PTP and PTP1B in signal transduction and diseases: From diabetes, obesity to cell cycle and cancer", Biochimica et Biophysica Acta, vol. 1754, 2005, pp. 108-117.

Dufresne, et al., "The Development of potent non-peptidic PTP-1B inhibitors", Bioorganic & Medicinal Chemistry Letters, vol. 14, 2004, pp. 1039-1042.

Dutta, et al., "Polypeptides. Part XII. The preparation of 2-pyridyl Esters and their Use in Peptide synthesis", J. Chem. Soc., vol. 1971, pp. 2896-2902.

Egawa, et al., "Protein-tyrosine Phosphatase-1B Negatively regulates insulin signaling in L6 Myocytes and Fao Hepatoma Cells", J. of Biological Chemistry, vol. 276, No. 13, pp. 10207-10211, 2001.

Elchebly, et al., "Increased Insulin Sensitivity and Obesity Resistance in Mice Lacking the Protein Tyrosine Phosphastase-1B Gene", Mar. 5, 1999, vol. 283 Science. pp. 1544-1548.

Fang, et al., "Metallothionein antagonized aging-induced cardiac contractile dysfunction: role of PTP1B, insulin receptor tyrosine phosphorylation and Akt", Aging Cell, 2006, pp. 177-185.

Fargion, et al., "Iron and Insulin resistance", Aliment Pharmacol Ter., 2005, vol. 22, Suppl. 2, pp. 61-63.

Ferber, et al., "Vanadate Normalizes hyperglycemia and Phosphoenolpyruvate carboxykinase mRNA levels in ob/ob mice", Metabolism, Nov. 1994, vol. 43, No. 11, pp. 1346-1354.

Ferris, et al., "Nucleosides from Carbohydrate Adducts of Diaminomaleonitrile. A Novel Synthesis of 5-Amino-1-(b-d- ribofuranosyl)imidazole-4-carboxamide and 5-Amino-1-(b-d-ribopyranosyl)imidazole-4-carboxamide", J. Org. Chem., 1985, vol. 50, pp. 747-754.

Fiegel, et al., "Priming of Hepatocytes for Cell Culture by Partial Hepatectomy Prior to cell Isolation", Tissue Engineering, vol. 6, No. 6, 2000, pp. 619-626.

Fiegel, et al. "Influence of Flow Conditions and Matrix Coating on Growth and Differentiation of Three-Dimensionally Cultured Rat Hepatocytes", Tissue Engineering, vol. 10, No. 1/2, 2004, pp. 165-174.

Fleming, et al., "A Synthesis of (+)-Saxitoxin", Communications JACS, 2006, vol. 128, pp. 3926-3927.

Fischer, et al. "Protein Tyrosine Phosphates: A Diverse Family of Intracellular and Transmembrane Enzymes" Science, vol. 253, pp. 401-406, 1991.

Fishwick, et al., "Regio-and Chemoseletive Alkylation of 2, 3-Dialkylindoles. A Convenient Preparation of 2, 3, 3-Trialkyl-3H-Indoles", Heterocycles, vol. 32, No. 4, 1991, pp. 685-692.

Fishwick, et al., "Intramolecular [3+2] Cycloaddition versus 1, 4-hydrogen shift in indolium-N-methylides", Tetrahydron Letters, vol. 30, No. 33, pp. 4447-4448, 1989.

Franco, et al., "Diheterocyclic Compounds from Dithiocarbamates and Derivatives Thereof". VII 1-2(Benzazolylaminophenylsulphonyl)-4-{4-oxo-2-thioxo (oxo)-1, 2, 3, 4-tetrahydro-3quinazolinyl]benzenes, Jul.-Aug. 1995, Depart. Of Organ. Chemistry, pp. 1181-1183.

Friesen, et al. "Methanesulfenylation of 2, 3-Dialkylindoles: Synthesis and Reactions of 3-Methylthioindolenines", Tetrahedron Letters, vol. 26, No. 2, pp. 161-164, 1985.

Gao, et al., "Examination of Novel Non-phosphorus-Containing Phosphotryosyl Mimetics against Protein-Tyrosine Phosphatase-1B and Demonstration of Differential Affinities Toward Grb2 SH2 Domains", Bioorganic & Medicinal Chemistry Letters, vol. 10, 2000, pp. 923-927.

Garin, et al., "Diheterocyclic Compounds from Dithiocarbamates and Derivates Thereof>II [1] 2,2'-Diamino-6,6' Bibenzoazoles", Feb. 1990, pp. 321-326.

Geary, et al. "Lack of Pharmacokinetic Interaction for ISIS 113715, a 2'-0-Methoxyethyl Modified Antisense Oligonucleotide Targeting Protein Tyrosine Phosphatase 1B Messenger RNA, with Oral Antidiabetic Compounds Metformin, Glipizide or Rosiglitazone" Original Research Article, 2006, Clin. Pharm., vol. 45 No. 8, pp. 789-801.

Giernorth, et al., "Enantioselective Hydrogenation of Trimethylindolenine in Ionic Liquids", Adv. Synth. Catal., 2004, vol. 346, pp. 989-992.

Goldfine, et al., "In vivo and in vitro studies of vanadate in human and rodent diabetes mellitus", Molecular and Cellular Biochemistry, vol. 153, pp. 217-231, 1995.

Gonzalez-Rodriguez, "Developmental Switch from Prolonged Insulin Action to Increased Insulin Sensitivity in Protein Tyrosine Phosphatase 1B-Deficient Hepatocytes", Endocrinology, vol. 148, No. 2, pp. 594-608, 2007.

Gonzalez, et al. "Protecting groups for the pyrrole nitrogen atom. The 2-chloroethyl, 2-phenylsulfonylethyl, and related moieties", Can. J. Chem., vol. 61, 1983, pp. 1697-1702.

Guertin, et al., "Identification of a Novel Class of Orally Active Pyrimido[5, 4-3][1,2,3]trizine-5, 7-diamine-Based Hypoglycemic Agents with Protein Tyrosine Phosphatase Inhibitory Activity", Bioorganic & medicinal Chemistry Letters, vol. 13, 2003, pp. 2895-2898.

Gum, et al., "Reduction of Protein Tyrosine Phosphatase 1B increases Insulin-Dependent Signaling in ob/ob Mice", Diabetes, vol. 52, 2003 pp. 21-28.

Gum, et al., "Antisense Protein Tyrosine Phosphatase 1B Reverses Activation of p38 Mitogen-Activated Protein Kinase in Liver of ob/ob Mice", Molecular Endocrinology, vol. 17, No. 6, pp. 1131-1143, 2003.

Haase, et al. "Protein Tyrosine Phosphatases as targets of the combined insulinomimetic effects of zinc and oxidants", BioMetals, 2005, vol. 18, pp. 333-338.

Haj, et al., "Liver Specific Protein-Tyrosine Phosphatase 1B (PTP1B) Re-expression Alters Glucose Homeostasis of PTP1B-/- Mice", JBC Papers in Press, Feb. 7, 2005, M413240200, pp. 1-38.

Haj, et al., "Imaging Sites of receptor Dephophorylation by PTP1B n the surface of the Endoplasmic Reticulum", Science, Mar. 2002, vol. 295, pp. 1708-1712.

Hama, et al., "Palladium-catalyzed Intermolecular x-Arylation of Zinc Amide Enolates under Mild Condition", J. Am. Chem. Soci,. 2006, vol. 128, pp. 4976-4985.

Harley, et al., "Protein Tyrosine Phosphatase 1B inhibitors for the treatment of type 2 diabetes and obesity: Recent advances", Current Opinion in Investigational Drugs, 2003, vol. 4, No. 10, pp. 1179-1189.

Harris, et al. "NMR Nomenclature. Nuclear Spin Properties and Conventions for Chemical Shifts", Pure appl. Chem., vol. 73, No. 11, pp. 1795-1818, 2001.

Heldin, "Dimerization of Cell Surface Receptors in Signal Transduction" Cell, vol. 80, pp. 213-223, 1995.

Hill, et al., "Enantioselective Synthesis of Protected 1-4-[sulfonamido(difluoromety)]phenylalanine and 1-4-[sulfonamido(methyl)phenylalanine and an Examination of Hexa- and Tripeptide Platforms for Evaluating pTyr Mimics for PTP1B Inhibition", J. Org. Chemistry, 2006, vol. 71, pp. 8190-8197.

Hiremath et al. "Synthesis of indolothiazoles and indolothiazolidinones" Indian J. chem. Section B. Org. Chem. Including Med. Chem., vol. 28B, pp. 824-828, 1928.

Hodges, et al., "Synthesis of a Spirocyclic Indoline Lactone", J. Org. Chem., 2004, vol. 69, pp. 2504-2508.

Hoffman, et al., "Protein Tyrosine Phosphatases: Strategies for Distinguishing Proteins in a Family Containing Multiple Drug Targets and Anti-Targets", Current Pharmaceutical Design, 2004, vol. 10, pp. 1161-1181.

Holy, et al., "Synthesis of Ribonucleoside 5-)-Hydroxymethanephosphonates", Collection Czechoslov. Chem. Commun., vol. 36, 1971, pp. 316-317.

Holy, et al., "Nucleic Acid Components and Their analogues. CL. Preparation and Properties of some Nucleoside Hydroxyalkanephophonates", Institute of Organic Chemistry and Biochemistry, Collection Czechoslov. Chem. Commun., vol. 37, 1972, pp. 2066-2076.

Hoppe, et al., "Expression, purification and crystallization of human phosphotyrosine phosphatase 1B", Eur. J. Biochem., vol. 223, pp. 1069-1077, 1994.

Hotchandani, et al. "PTP1B Inhibitors: Capturing Interactions with Arg24", poster. Wyeth Research, pp. 1-2.

Hu, et al., "In Silico modeling of protein tyrosine phosphatase 1B inhibitors with cellular activity", Bioorganic & Med. Chem. Letters, vol. 16, 2006, pp. 6321-6327.

Hudson, et al., "The Reactivity of Esters of Quinquivalent Phosphorus towards anions", Hudson and Harper: The Reactivity of Esters of, 1958, pp. 1356-1360.

Hum, et al., "Cyclic five-membered phosphinate esters as transition state analogues for obtaining phosphohydrolase antibodies", Can. J. Chem., vol. 78, pp. 642-655.

Hum, et al. "Synthesis of [Difluoro-(3-alkenylphenyl)-methyl]phosphonic Acids on Non-Crosslinked Polystyrene and their Evaluation as Inhibitors of PTP1B", Bioorganic & Medicinal Chemistry Letters, vol. 12, 2002, pp. 3471-3474.

Hunter, "Protein-Tyrosine Phosphatases: The Other Side of the Coin" Cell, vol. 58, pp. 1013-1016, 1989.

Huyer, et al., "Mechanism of Inhibition of Protein-tyrosine phosphatases by Vanadate and Pervanadate", The Journal of Biological Chemistry, vol. 272, No. 2, pp. 843-851, 1997.

Huyer, "Affinity Selection from Peptide Libraries to Determine substrate Specificy of Protein Tyrosine Phosphatases", Analytical biochemistry, vol. 258, 1998, pp. 19-30.

Inoue, et al., "N-Alkylation of Imides with O-Alkylisourea under Neutral Conditions", Communications Synthesis, pp. 332-334.

Ishibashi, et al., "C-Alkylations of Indoles and Pyrroles with x-Chloro Sulfides on an alumina Surface: A Short Synthesis of Dithyreanitrile", J. Chem. Soc. Perkin Trans, 1992, pp. 2821-2825.

Ishido, et al., "Partial Protection of Carbohydrate Derivatives. Part 3. Regioselective 2'o-Deacylation of fully Acylated Purine and Pyrimidine Ribonucleosides with Hydrzaine Hydrate", JCS Perkin I, pp. 2088-2098, 1979.

Ishido, et al., "Partial Protection of Carbohydrate Derivatives. Part 4. Regioselective 2'o-Deacylation of fully Acylated Purine and Pyrimidine Ribonucleosides with Hydroxylaminium Acetate", JCS Perkin I, pp. 563-573, 1980.

Itai, et al., "Stereochemistry of N-Methylbenzanilide and Benzanilide", Tetrahedron Letters, vol. 30, No. 45, pp. 6177-6180, 1989.

Ito, et al., "Synthesis of Indole Derivatives by Cu2O-Catalyzed Cyclization of 0-(x-Cyanoalky) phenyl Isocyanides and 0-[a-(Methoxy-carbonyl)alkyl]phenyl Isocyanides", Bulletin of the Chemical Society of Japan, vol. 51, No. 4, pp. 1186-1188, 1978.

Jackson, et al., "Electrophilic Substitution in Indoles. Part 12. Kinetic Studies of the Rearrangement of 3,3-Disubstituted to 2,3-Disubstituted Indoles", J. Chem. Soc. Perkin Trans, vol. 2, 1987, pp. 1215-1219.

Jackson, et al. "Electrophilic Substitution in indoles-I", Tetrahedron, 1965, vol. 21, pp. 989-1000.

Jackson, et al., "Insulin-mimetic effects of vanadate in primary cultures of rat hepatocytes", Diabetes, Sep. 1988, vol. 37, No. 9, pp. 1234-1240.

Jelveh, et al., "Inhibition of cyclic AMP dependent protein kinase by vanadyl sulfate", J. Biol. Inorg. Chem., 2006, vol. 11, pp. 379-388.

Jia, et al. Structural Basis for Phosphotyrosine Peptide Recognition by Protein Tyrosine Phosphatase 1B, Science, vol. 268, pp. 1754-1758, 1995.

Jia, et al., "Structure of Protein Tyrosine Phosphatase 1B in Complex with inhibitors Bearing two Phosphotyrosine Mimetics", J. Med. Chem., 2001, vol. 44, pp. 4584-4594.

Johnson, et al., "Protein Tyrosine Phosphatase1B Inhibitors for Diabetes", Nature Reviews Drug Discovery 1, pp. 696-709, Sep. 2002, vol. 1 No. 9.

Kaboudin, et al. "A convenient and mild procedure for the preparation of x-Keto Phosphonates of 1-Hydroxyphosphonates under solvent-free conditions using microwave", Synthetic Communications, vol. 31, No. 15, pp. 2245-2250, 2001.

Kardos-Balogh, et al., "Synthesis of Vinca Alkaloids and related Compounds. XLIII Unexpected Rearrangement of 3-Acylindolenines", Heterocycles, vol. 28, No. 1, 1989, pp. 303-313.

Kashima, et al. "New peptide Synthesis using the ozonolysate of 2-(1-phthalimido)alkyl-5-phenyloxazoles" J. Het. Chem., vol. 28, pp. 1241-1244, 1991.

Katritzky et al. "1-(Cyanomethyl) benzotriazole as a Convenient Precursor for the Synthesis of 2-Substituted Thiazoles" J. Org. Chem, vol. 60, pp. 5638-5642, 1995.

Katvalyan, et al. "Conformation Analysis of 3-Ketopiperidines, Vicinal N1C(2)-Alkyl Interactions", Jan.-Feb. 1985, pp. 53-55.

Kenner, et al., "Protein-tyrosine Phosphatase 1B is a negative Regulator of Insulin and Insulin-like Growth Factor-I-stimulated Signaling", The Journal of Biological Chemistry, vol. 271, No. 33, 1996, pp. 19810-19816.

Kim, et al., "New Amino-protective Reagents for t-Butoxycarbonylation and Benzyloxcarbonylation of Amines and Amino Acids", Bull. Chem. Soc. Jpn., vol. 58, No. 12, 3570-3575.

Kimura, et al., "Studies on Nucleosides and Nucleotides. IV. Synthesis and reactions of 3,5,-o-(Triphenyl) Phosphoranyladenosine", Chemistry Letters, pp. 1473-1476, 1974.

Kimura, et al., "Studies on Nucleosides and Nucleotides. VIII. Preparation and Reactions of Triphenylphosphoranediylnucleosides", Chemistry Society of Japan. Bull. Chem. Soc. Jpn, vol. 53, pp. 3670-3677, 1980.

Klaman, et al. "Increased Energy Expenditure, Decreased Adiposity, and Tissue-Specific Insulin Sensitivity in Protein-tyrosine phosphatase 1B-Deficient Mice", Molecular and Cellular biology, Aug. 2000, vol. 20, No. 15, pp. 5479-5489.

Klopfenstein, et al., "1, 2, 3, 4-Tetrahydroisoquinolinyl sulfamic acids as phophatase PTP1B inhibitors", Bioorganic & Medicinal Chemistry Letter, vol. 16, 2006, pp. 1574-1578.

Koch, et al., "SH2 and SH3 Domains: Elements That Control Interactions of Cytoplasmic Signaling Proteins", Science, vol. 252, pp. 668-674, 1991.

Kole, et al., "Phosphonate inhibitors of protein-tyrosine and serine/threonine phosphatases", Biochem. J., 1995, vol. 311, pp. 1025-1031.

Kole, et al., "Protein-tyrosine Phosphatase Inhibition by a Peptide Containing the Phosphotyrosyl Mimetic, L-O-Malonytyrosine" Biochemical and Biophysical research communications, vol. 209, No. 3, 1995, pp. 817-822.

Koizumi, et al., "Direct Comparison of In Vivo Antisense Activity of ENA Gligonucleotides Targeting PTP1B mRNA with that of 2'-0-(2-Methoxy)ethyl-Modified Oligonucleotides" Oligonucleotides, vol. 16, pp. 253-262, 2006.

Kwong, et al., "Mild and Efficient Copper-Catalyzed Amination of Aryl Bromides with Primary Alkylamines", Organic Letters, 2003, vol. 5, No. 6, pp. 793-796.

Lam, et al., "Leptin increases hepatic insulin sensitivity and protein tyrosine phosphatase 1B expression", Mol. Endocrinol., Jun. 2004, vol. 18, No. 6, pp. 1333-1345.

Lam, et al., "Leptin resistance following over-expression of protein tyrosine phosphatase 1B liver", Journal of Molecular Endocrinology, 2006, vol. 36, pp. 163-174.

Laronze, et al., "Methylene-Indolines, Indolenines and Indoleniniums, XXI an Indolenine Approach to Morphine related compounds", Tetrahedron Letters, vol. 27, No. 4, pp. 489-492, 1986.

Lau, et al. "Structure based design of a series of potent and selective non peptidic PTP-1B inhibitors" Bioorg. Med. Chem. Lett., vol. 14, pp. 1043-1048, 2004.

Lee, "Convenient Synthesis of Carboxylic Esters Using 2-Pyridyl Carbonates", Korean Chem. Soc., vol. 10, No. 6, 1989, pp. 611-612.

Lee, "Intra and Intermolecular x-Sulfamioalkylation Reactions", J. Org. Chemistry, 1990, vol. 55, pp. 6098-6104.

Leighton, et al., "Small molecule glucokinase activators as novel anti-diabetic agents", Kinases in Diabetes, 2005, Biochemical Society., pp. 371-374.

Letcher, et al. "Oxazolo[3,2-a]indoles, Pyrrolo-and Azepino-[1,2-a]indoles from 3H-Indole 1-Oxides and Acetylenecarboxylic Esters by Skeletal Rearrangements", J. Chem. Soc., 1993, pp. 939-944.

Leung, et al. "The Difluoromethylenesulfonic Acid Group as a Monoanionic Phosphate Surrogate for Obtaining PTP1B Inhibitors", Bioorganic & Medicinal Chemistry, vol. 10, 2002, pp. 2309-2323.

Li, et al., "Solid-Phase synthesis of Potential protein tyrosine phosphatase inhibitors via the UGI four-component condensation", Bioorganic & Medicinal Chemistry Letters, vol. 8, 1998, pp. 2443-2446.

Liu, et al., "Fragment Screening and Assembly: A Highly efficient approach to a Selective and cell active protein tyrosine phophatase 1B inhibitor", J. Med. Chem., 2003, vol. 46, pp. 4232-4235.

Li, et al. "Insulin Receptor Kinases-Associated Phosphotyrosine Phosphatases in hepatic Endosomes: Assessing the Role of phosphotyrosine Phosphatase-1B" Endocrinology, vol. 147, No. 2, pp. 912-918.

Li, et al., "Crystal Structure of a Complex between Protein Tyrosine Phosphatase 1B and the Insulin Receptor Tyrosine Kinase", Structure, vol. 13, pp. 1643-1651, Nov. 2005.

Liu, et al., Supporting Information "Selective Protein Tyrosine Phosphatase 1B Inhibitors: Targeting the Second Phosphotyrosine Binding Site with Non-Carboxylic Acid-Containing Ligands" Abbott Laboratories, pp. 1-38.

Liu, et al., "Selective Protein Tyrosine Phosphatase 1B Inhibitors: Targeting the Second Phosphotyrosine Binding Site with Non-Carboxylic Acid-Containing Ligands" J. Med. Chem., 2003, vol. 46, pp. 3437-3440.

Liu, et al., "Free and Polymer-Bound Tricyclic Azaphosphatranes HP(RNCH2CH@)3N+: Procatalysts in Dehydrohalogenations and Debrominations with NaH", J. Org. Chem., 1999, vol. 64, pp. 4840-4843.

Liu, et al. "Discovery and Structure-Activity Relationship of Oxalylarylaminobenzoic Acids as Inhibitors of Protein Tyrosine Phosphatase 1B", J. Med. Chem., 2003, vol. 46, pp. 2093-2103.

Liu, et al. "Protein Tyrosine Phosphatase 1B Inhibition: Opportunities and Challenges", Current Med. Chem., 2003, vol. 10, pp. 1407-1421.

Liu, et al., "Technology Evaluation: ISIS-113715, Isis", Current Opinion in Molecular Therapeutics, 2004, vol. 6, No. 3, pp. 331-336.

Liu, et al., "Molecular dynamics simulations of interaction between protein-tyrosine phophatase 1B and a bidentate inhibitor", Acta Pharmacologica Sinica, Jan. 2006, vol. 27, No. 1. pp. 100-110.

Liu, et al., "1,1-Disubstituted Methoxyimino Acetic Acid (A-119505), a Novel PTP1B Inhibitor with Anti-Diabetic Effects in ob/ob Mice", 2127-PO, pp. A506.

Lund, et al., "Structure-based design of Selective and potent Inhibitors of protein-tyrosine phosphatase", J. of Biological Chemistry, vol. 279, No. 23, pp. 24226-24235, 2004.

Lund, et al. "Mechanism of protein tyrosine phosphatase 1B-mediated inhibition of leptin signalling" journal of molecular endocrinology, 2005, vol. 34, pp. 339-351.

Mahadev, et al., "Insulin-stimulated hydrogen Peroxide reversibly inhibits protein-tyrosine phosphatase 1B in Vivo and Enhances the Early Insulin", J. of Biological Chemistry, 2001, vol. 276, No. 24, pp. 21938-21942, 2001.

Mahmood, et al., "New Perfluoroalkylphosphonic and Bis (perfluoroalkyl) phosphinic Acids and Their Precursors", Inorg. Chem., 1986, vol. 25, pp. 3128-3131.

Mahmood, et al. "Simple Preparation of Dialky Polyfluoroalkyl phosphonates", Synthetic Communications, vol. 17, No. 1, pp. 71-75, 1987.

Malabu, et al., "Effects of Chronic Vanadate administration in the STZ-induced diabetic rat. The antihyperglycemic action of vandate is attributable entirely to its suppression of feeding", Diabetes, vol. 43, Issue I, pp. 9-15.

Malamas, et al., "Novel Benzofuran and Benzothiophene Biphenyls as Inhibitors of protein Tyrosine Phosphatase 1B with antihyperglycemic Properties", J. Med. Chem., 2000, vol. 43, pp. 1293-1310.

Malamas, et al., "New Azolidinediones as Inhibitors of protein tyrosine phosphatase 1B with Antihyperglycemic Properties", J. Med. Chem., 2000, vol. 43, pp. 995-1010.

Mandal, et al. "Reduction of Lactams and Thiolactams by Sodium Borohydride: Application in the Synthesis of Some Alkaloids", J. Org. Chem., 1988, vol. 53, pp. 4236-4241.

Mauro, et al., "Zip Codes direct intracellular protein tyrosine phosphatases to the correct cellular address" Trends Biochem.Sci., vol. 19, pp. 151-155, 1994.

Markovsku,et al., "Application of Dialkylaminosulfur Trifluorides int eh Synthesis of Fluroroganic Compounds", Communication, Dec. 1973, pp. 787-789.

Maslennikov, et al., "Dialkyl (Trifluoromethyl) phoshonates", translated from Zhurnal Obshchei Khimii, vol. 53, No. 12, 1983, pp. 2417-2419.

Marzban, et al., "Mechanisms by which Bis(Maltolato)Oxovanadium (IV) Normalizes Phosphoenolpyruvate Carboxykinase and Glucose-6-Phosphatase Expression in Streptozotocin-Diabetic Rats In Vitro", Endocrinology, vol. 143, No. 12, pp. 4636-4645.

Masuda, et al. "Regioselective Alkylation of Thiazolylsulfonamides: Direct and Efficient Synthesis of 3-Alkylthiazolidene Derivatives", Synthetic Communications, vol. 35, pp. 2305-2316, 2005.

Mayer, et al. "Studies of Trifluoromethylphosphonamidite Analogues as Building Blocks in Oligonucleotide Synthesis", Tetrahedron Letters, vol. 36 No. 12, pp. 2047-2050, 1995.

McCain, et al. "Suramin Derivatives as Inhibitors and Activators of Protein-tyrosine Phosphatases", J. of Biol. Chem., vol. 279, No. 15, Apr. 9, 2004., pp. 14713-14725.

McClinton, et al. "Trifluoromethylations and Related Reactions in Organic Chemistry", Tetrahedron, vol. 48, No. 32, pp. 6555-6666, 1992.

Mehdi, et al., "Involvement of Insulin-like Growth Factor Type 1 Receptor and Protein Kinase Co in Bio(maltolato)oxovanadium (IV)-Induced Phophorylation of Protein Kinase B in HepG2 Cells", Biochemistry, 2006, vol. 45, pp. 11605-11615.

Meier, et al., "Letter to the Editor: Backbone resonance assignment of the 298 amino acid catalytic domain of protein tyrosine phosphatase 1B (PTP1B)", Journal of Biomolecular, NMR, vol. 24, pp. 165-166, 2002.

Meng, et al "Regulation of Insulin Signaling through Reversible Oxidation of the Protein-tyrosine Phosphatases TC45 and PTP1B", Journal of Biological Chemistry, vol. 279, No. 36, 2004, pp. 37716-37725.

Merchan, et al., "Synthesis of 2-Sulfonylaminobenzimidazols and 4, 5-Dicyano-2sulfonylaminoimidazols from N-Dichloromethylensulfonamides", Communications, Synthesis, pp. 984-986, 1982.

Merchan, et al., "Synthesis of 2-Arlyiminoimidazolidines and 2-Arlyiminoimidazolidines from Methyl N-Arylidithiocarbamates", Communications, Synthesis, pp. 482-484, 1981.

Meyers, et al.,"Synthesis and Biological Activity of Novel 5-fluoro-2'-deoxyuridine phosphoramidate Prodrugs", J. Med. Chem., 2000, vol. 43, pp. 4313-4318.

Meyers, et al., "Activation Mechanisms of Nucleoside Phosphoramidate Prodrugs". J. Med. Chem., 2000, vol. 43, pp. 4319-4327.

Millauer, et al., "Glioblastoma growth inhibited in vivo by a dominant-negative Flk-1 mutant", Nature, pp. 367-577, 1994.

Mitchell, et al. "Prodrugs of Phosphonoformate: Products, Kinetics and Mechanisms of Hydrolysis of Dibenzyl (Methoxycarbonyl) phosphonate", J. Chem. Soc. Perkin Trans., 1991, pp. 1297-1303.

Mohammad, et al., "Bio(Maltolato)oxovanadium(IV) inhibits the activity of PTP1B in Zucker rat skeletal muscle in vivo", Molecular and Cellular Biochemistry, vol. 229, pp. 125-128, 2002.

Montalibet, et al., "Residues Distant from the Active Site influence protein-tyrosine Phosphatase 1B Inhibitor Binding", Journal of biological Chemistry, vol. 281, No. 8, Feb. 24, 2006, pp. 5258-5266.

Moretto, et al., "Bicyclic and tricyclic thiophenes as protein tyrosine phosphatase 1B inhibitors", Bioorganic & Medicinal chemistry, vol. 14, 2006, pp. 2162-2177.

Morimoto, et al. "Efficient Asymmetric Hydrogenating of Imines Catalyzed by a neutral Iridium(I) Complex of (4r,5R)-Mod-Diop)" Chem. Pharm. Bull, vol. 42 No. 9, pp. 1951-1953, 1994.

Morkved, et al., "Potential Acyl-transfer Agents Reactions of N-acyl-2-pyridmecarboxamide with Nucleophiles" Acta Chemica Scandinavica B., 1982, pp. 381-388, vol. 36.

Mukherjee, et al., "Vanadium—an element of atypical biological significance", Toxicology Letters, vol. 150, 2004, pp. 135-143.

Mulliez, et al. "Synthesis of Di- and Tri-Substituted 2, 4-Dioxo-1,3,2-diazzpholidines and 4-Oxo-2-thioxo-1,3,2-diazapholidines", Communications, Synthesis, pp. 478-480.

Munier, et al. "Trifluoromethylation of sugar 1,4-Lactones: Synthesis of 5-Deoxy-5,5,5-Trifluoro-D and L-Ribose and Lyxose Derivatives", Tetrahedron Letters, vol. 34, No. 51, pp. 8241-8244, 1993.

Muniz, et al. "Sulfamide Synthesis via Pd-catalyzed Cross-Coupling", Synlett, 2005, No. 1, pp. 149-151.

Nair, et al., "Facile Synthesis of Fluorinated Phosphonates via Photochemical and Thermal reactions" J. Am. Chem. Soc., 1997, vol. 119, pp. 9137-9143.

Najjar, et al., "Insulin acutely decreases hepatic fatty acid synthase activity", Cell Metabolism, Jul. 2005, vol. 2, pp. 43-53.

Nishikata, et al., "A Phosphotyrosine-containing quenched Fluorogenic peptide as a novel substrate for protein tyrosine phophatases", Biochem. J., Oct. 15, 1999, vol. 343, Pt. 2, pp. 385-391.

Nishino, et al., "Partial Protection of Carbohydrate Derivatives, Part. 18, simple, preparative procedure for 5-'Q-Acylribonucleosides, Highly regioselective Q-Deacylatin at 2' and 3' positions of fully acylated purine and pyrimidine ribonucleoside through sodium methoxide—THF system", Tetradron, vol. 41, No. 23, pp. 5503-5506.

Norlin, et al. "Synthesis of [14C] Sarin", Journal of Labeled Compounds and Radiopharmaceuticals, J. Label Compd Radiopharm, 2003, vol. 46, pp. 599-604.

Norlin, et al."x-Haloenamines as Reagents for the conversion of phosphorus Oxyacids to their Halogenated Analogues", Synthesis, 2005, No. 11, pp. 1765-1770.

Pannifer, et al. "Visualization of the Cysteinyl-phosphate Intermediate of a Protein Tyrosine Phosphatase by X-ray Crystallography" J. Bio. Chem., vol. 273, pp. 10454-10462, 1998.

Pawson, "Protein Modules and signalling Networks", Nature, vol. 373, pp. 573-580, 1995.

Pei, et al., "Inhibition of Protein Tyrosine Phosphatase 1B as a Potential Treatment of Diabetes and Obesity", Current Pharmaceutical Design, 2004, 10, 3481-3504.

Pelchowicz, "Organic Phosphorus Compounds. Part 1, The reaction of Dialkyl Methylphosphonates and Methylphosphonothionates with Inorganic Acid Chlorides", pp. 238-240, 1961.

Piettre, et al. "Easy and General Access to x,x-Dilfuormethylene Phosphonothioic Acids. A new Class of Compounds", Tetrahedron Letters, vol. 37, No. 13, pp. 2229-2232, 1996.

Pot, et al. "A Thousand and two protein tyrosine phosphatases" Biochem Biophys. Acta, vol. 1136, pp. 35-43, 1992.

Poulin, et al. "Phosphoranes. I. Tris(trifluoromethyl)bis(dimethylamino)phosphorane, (CF3)3P[n(ch3)2]2, and related Chlorodimethylaminotrifluoromethylphosphoranes", Inorganic Chemistry, vol. 13, No. 10, 1974, pp. 2324-2333.

Preet, et al., "Restoration of ultrastructural and biochemical changes in alloxan-induced diabetic rat sciatic nerve on treatment with Na3Vo4 and Trigonella—a promising antidiabetic agent", Molecular and Cellular Biochemistry, vol. 278, pp. 21-31, 2005.

Price, et al., "Some Sulfonamide Derivatives of 2-aminobenzimidazole", 1946, pp. 269-274.

Puius, et al., "Identification of a second aryl phosphate-binding site in protein-tyrosine phosphatase 1B: A paradigm for inhibitor design", vol. 94, pp. 13420-13425, 1997.

Purdum, et al. "Synthesis of Monoesters of Aryl-(or alkyl-) phosphonic Acids of Selected Arenols. A Study of the Effect of Dimethylformamide on the preparation of 2-Naphthylphenylphosphonic Acid via Proton and Phosphorus-31 Nuclear Magnetic Resonance Analysis", J. Org. Chem., vol. 41, No. 7, 1976, pp. 1160-1165.

Qabar, "A Facile Solution and solid Phase Synthesis of Phosphotyrosine Mimetic L-4-[DiethylPhosphono(difluoromethyl)]-Phenylalanine (F2Pmp(Eto)2) Derivatives" Tetrahedron, vol. 53, No. 32, pp. 11171-11178, 1997.

Qiu, et al., "Hepatic PTP-1B Expression Regulates the Assembly and Secretion of Apolipoprotein B-Containing Lipoproteins", Diabetes, vol. 53, pp. 3057-3066, 2004.

Qui, et al., "A Facile and General Preparation of x,x-Difluoro Benzyllic Phosphonates by the CuCi Promoted Coupling Reaction of the (Diethylphosphonyl)difluoromethylcadmium Reagent with Aryl Lodides" Tetrahedron Letters, vol. 37, No. 16 pp. 2745-2748, 1996.

Radchenko, et al., "Synthesis of Polycarpine, a Cytotoxic Sulfur-Containing Alkaloid from the Ascidian Polycarpa Aurate, and Related Compounds", Tetrahedron Letters, vol. 38, No. 20, pp. 3581-3584.

Rahil, et al., "Intramolecular participation of the Amide Group in Acid and Base catalyzed Phosphonate Monoester Hydrolysis", J. Chem. Soc. Perkin Trans, 1991, pp. 947-950.

Rajagopalan, S. HCAPLUS Abstract 39:3167, "Bacterial Chemotherapy IV Synthesis of Ni, N4-diacylsulfamlamides", 1945, especially RN 784193-27-2, pp. 1.

Ramachandran, et al. "Protein Tyrosine Phophatase 1B: a novel target for type 2 diabetes and obesity", Curr. Top. Med. Chem., 2003, vol. 3, No. 7, Abstract.

Ramaiah, et al. "1-Trifluoromethyl-1-Cyclohexanol", pp. 232-241.

Rao, et al. "Novel Synthesis of 4(5)-cyclic Amino-5(4)-Ntiroimidazoles", Synthetic Communications, vol. 24, No. 3, pp. 341-351, 1994.

Rao, et al. "In Silico Structure-Based Design of a Potent and Selective Small Peptide Inhibitor of Protein Tyrosine Phosphatase 1B, A Novel Therapeutic target for Obesity and Type 2 Diabetes Melitus: A Computer Modeling Approach", Journal of Biomolecular Structure & Dynamics, vol. 23, No. 4, 2006, pp. 377-384.

Ravichandran, et al., "Phosphorylation of PTP1B at Ser(50) by Akt impairs its ability to dephosphorylate the insulin receptor", Mol. Endocrinol., Oct. 15, 2001, vol. 10, pp. 1768-1780.

Reetz, "A New Class of Chiral Diphosphines Having Planar Chirality", Tetrahedron Letters, vol. 40, 1999, pp. 4977-4980.

Revesz, et al., "Non-peptide Itam Mimics as Zap-70 Antagonist", Bioorganic & Medicinal Chemistry Letters, vol. 7 No. 22, pp. 2875-2878, 1997.

Ritter, H, et al. HCAPLUS Abstract 52:30289, "Piperidine Derivative", 1958, especially RN 860384-66-3, pp. 1.

Rodricks, et al., "Synthesis of Cyclic Guanidines", J.Org. Chem., vol. 36, No. 1, 1971, pp. 46-48.

Rondinone, et al., "Protein Tyrosine Phosphatase 1B Reduction Regulates Adiposity and expression of Genes Involved in Lipogenesis", Diabetes, vol. 51, Aug. 2002, pp. 2405-2411.

Ruff, et al., "Peroxovanadate Induces Tyrosine Phosphorylation of Multiple Signaling proteins in Mouse Liver and kidney", Journal of Biological Chemistry, vol. 272, No. 2, pp. 1263-1267, Jan. 10, 1997.

Rye, et al., "Phosphate Isosteres in Medicinal Chemistry", Current Medicinal Chemistry, 2005, vol. 12, pp. 3127-3141.

Salmeen, et al., "Molecular Basis for the Dephosporylation of the Activation Segment of the Insulin Receptor by Protein Tyrosine Phosphatase 1B", Molecular Cell, vol. 6, pp. 1401-1412, Dec. 2000.

Sangwan, et al., "Protein-tyrosine Phosphatase 1B Deficiency Protects against Fas-induced Hepactic Failure", Journal of Biological Chemistry, vol. 281, No. 1, pp. 221-228.

Saito, et al. "Molecular Characterization of Protein Tyrosine Phosphatases" Cell Growth and Differentiation, vol. 2, pp. 59-65, Jan. 1999.

Sapi, et al., "Indole as a Tool in synthesis. Indolenine Approach to 4, 5-Epoxy-10-normorphinans", Tetrahedron, vol. 52, No. 24, pp. 8209-8222, 1996.

Sarmiento, et al., "Structure-Based Discovery of Small Molecule inhibitors targeted to protein tyrosine Phosphatase", J. Med. Chem, 2000, vol. 43, pp. 146-155.

Scapin, et al. "The Structural Basis for the selectivity of Benzotriazole Inhibitors of PTP1B", Biochem., vol. 42, pp. 11451-11459, 2003.

Schlessinger, et al., "Growth Factor Signaling by Receptor Tyrosine Kinases" Neuron, vol. 9, pp. 383-391, 1992.

Schultz et al., "Acetoxymethyl esters of phosphates, Enhancement of the permeability and Potency of cAMP" J. Bio. Chem., vol. 268, pp. 6316-6322, 1993.

Schwender, et al., "1-Naphthylmethylphosphonic acid derivatives as Osteoclastic acid phophatase inhibitors", Bioorganic & Medicinal Chemistry Letters, vol. 5, No. 16, pp. 1801-1806, 1995.

Sedaghat, et al., "A Mathematical model of metabolic insulin signaling pathways", Am. J. Physiol Encrinal Metab, vol. 283, E1084-E1101, 2002.

Sekine, "Synthesis of Chemically Stabilized Phosmidosine Analogues and the Structure-Activity Relationship of Phosmidosine", J. Org. Chem., 2004, vol. 69, pp. 314-326.

Shafrir, et al., "Treatment of diabetes with Vanadium Salts: General Overview and Amelioration of Nutritionally induced diabetes in the Psammomys obesus gerbil", Diabetes Metabolism Research and Reviews, Diabetes Res. Rev., 2001, vol. 17, pp. 55-66.

Shen, et al., "Acquisition of a Specific and Potent PTP1B Inhibitor from a Novel Combinatorial Library and Screening Procedure", The Journal of Biological Chemistry, vol. 276, No. 50, pp. 47311-47319.

Shimizu, et al., "Protein-tyrosine Phosphatase 1B as New Activator for Hepatic Lipogenesis via Sterol Regulatory Element-binding Protein-1 Gene Expression", J. of Biological Chem., vol. 278, No. 44, pp. 43095-43101, 2003.

Shultz et al. "Mutations at the Murine Motheaten Locus Are within the Hematopoietic Cell Protein-Tyrosine Phosphatase (Heph) Gene" Cell, vol. 73, pp. 1445-1454, 1993.

Skolnik, et al., "Cloning of P13 Kinase-Associated p85 Utilizing a novel Method for Expression/Cloning of Target Proteins for Receptor Tyrosine Kinases" Cell, vol. 65, pp. 83-90, 1991.

Skorey, et al., "Enzyme occupancy measurement of intracellular protein tyrosine phosphatase 1B using photoaffinity probes", Analytical Biochemistry, vol. 349, 2006, pp. 49-61.

Smith, et al., "Tremorgenic Indole Alkaloid Studies. 6. Preparion of an advanced intermediate for the synthesis of penitrem D. Synthesuis of an indole-oxocane", Tetrahedron, vol. 45 No. 8, pp. 2431-2499, 1989.

Sparks, et al., "Benzothiazole-benzimidazole (S)-IZD Derivatives as Protein Tyrosine Phosphatase-1B Inhibitors", Poster, Discovery Chemistry, Incyte Corporation, 2006, pp. 187-193.

Sparks, et al., "Benzothiazole-benzimidazole (S)-IZD Derivatives as Protein Tyrosine Phosphatase-1B Inhibitors", Bioorganic & Medicinal Chemistry Letters, vol. 17, 2007, pp. 736-740.

Srivastava, et al. "Insulino-mimetic and anti-diabetic effects of vanadium compounds", 2004, Diabetes UK, Diabetic Medicine, vol. 22, pp. 2-13.

Stankovic, et al. "The Role of 4-phosphonodifluoromethly-and 4-phosphono-phenylalanine in the selectivity and cellular uptake of SH2 Domain Ligands", Bioorganic & Medicinal Chemistry Letters, vol. 7, No. 14, pp. 1909-1914, 1997.

Steiber et al., "Multistep Solid-Phase Synthesis of an Antibiotic and Receptor Tyrosine Kinase Inhibitors Using the Traceless Phenylhydrzide Linker" Chem Eur. J., vol. 9, pp. 3282-3291, 2003.

Stenlund, et al., "Studies of small molecule interactions with protein phosphatases using biosensor technology", Analytical Biochemistry 353 (2006), 217-225.

Stowell, et al., "The Mild Preparation of Synthetically Useful Phosphonic Dichlorides: Application to the synthesis of Cyclic Phosphonic Diesters and Diamides", Tetrahedron Letters, vol. 31, No. 23, pp. 3261-3262, 1990.

Stuible, et al., "Cellular Inhibition of Protein Tyrosine phosphatase 1B by uncharged Thioxothiazolidinone Derivatives", ChembioChem, 2007, vol. 8, pp. 179-186.

Sun, et al., "Hyrtiosal, a PTP1B Inhibitor from the Marine Sponge Hyrtios erectus, Shows Extensive Cellular Effects on P13K/AKT Activation, Glucose Transport, and TGFB/Smad2 Signaling", ChemBioChem, 2007, vol. 8, pp. 187-193.

Swinney, "Biochemical Mechanisms of drug action: What does it take for success?" Nature Reviews/Drug Discovery, vol. 3, Sep. 2004, pp. 801-808.

Szczepankiewicz, et al., "Discovery of a Potent, Selective Protein Tyrosine Phosphatase 1B Inhibitor using a Linked-Fragment Strategy", J. Am. Chem. Soc., 2003, vol. 125, pp. 4087-4096.

Ta-Shma, et al. "A Kinetic Study of Competing fragmentation and hydrolysis of phenyl hydrogen x-hydroxyiminobenzylphosphonate—a case of acid mediated inhibition of acid catalysis", J. Chem. Soc. Perkin Trans, vol. 2, 2001, pp. 1404-1407.

Taghibiglou, et al., "Hepatic Very Low density Lipoprotein-ApoB Overproduction is associated with attenuated Hepatic Insulin signaling and overexpression of Protein-tyrosine Phosphatase 1B in a Fructose-fed hamster Model of Insulin Resistance", The Journal of Biological Chemistry, vol. 277, No. 1, pp. 793-803, 2002.

Taha, et al., "Effects of Variable Docking Conditions and Scoring Functions on Corresponding Protein-Aligned Comparative Molecular field Analysis Models Constructed from Diverse Human Protein Tyrosine Phosphatase 1B Inhibitors", J. Med. Chem., 2005, vol. 48, pp. 8016-8034.

Taing, et al., "Potent and Highly Selective Inhibitors of the Protein Tyrosine Phosphatase 1B", Biochemistry, 1999, vol. 38, pp. 3793-3803.

Takahashi, et al., "A novel aminosterol reverses diabetes and fatty liver disease in obese mice", Journal of Hepatology, vol. 41, 2004, pp. 391-398.

Takase, et al., "Total Synthesis of Amauromine", Tetrahedron, vol. 42, No. 21, pp. 5887-5894, 1986.

Takayama, et al., "A General Synthetic Route of 3,3-Disubstitued 3H-Indoles and Rearrangement of their acyl Chloride adducts" Tetrahedron Letters, No. 5, pp. 365-368, 1973.

Tang, et al., "Decreased in Situ Insulin Receptor Dephosphorylation in Hyperglycemia-Induced Insulin resistance in Rat Adipocytes", Diabetes, vol. 50, Jan. 2001, pp. 83-90.

Tao, et al., "Insulin Stimulates tyrosine phosphorylation and inactivation of protein tyrosine phosphatase 1B in vivo", J. of Biol. Chemistry, vol. 276, No. 31, pp. 29520-29525, 2001.

Tawfik, et al., "1,8-Diazabicyclo[5.4.0]undecen Mediated transesterification of p-Nitrophenyl Phosphonates: A Novel Route to Phosphono Esters", papers, pp. 968-972, Oct. 1993.

Taylor, et al., "Inhibitors of Protein Tyrosine Phosphatase 1B (PTP1B)" Current Top Med. Chem., 2003, vol. 3, No. 7, Abstract.

Taylor, et al., "Recent Advances in protein tyrosine phosphatase 1B inhibitors", expert opinion investig. Drugs, 2004, vol. 13, No. 3, pp. 2-17.

Taylor, et al., "Potent Non-Peptidyl Inhibitors of Protein Tyrosine Phosphatase 1B", Bioorganic & Medicinal Chemistry, vol. 6, 1998, pp. 1457-1468.

Taylor, et al., "Structural Framework for the Protein Kinase Family," Ann. Rev. Cell Biol., vol. 8, pp. 429-462, 1992.

Taylor, et al., "Synthesis of Aryl(DifluoromethylenePhosphonates) via Electrophilic Fluorination of x-Carbanions of Benzylic Phosphonates with N-Fluorobenzenesulfonimide", Tetrahedron, vol. 54, 1998, pp. 1691-1714.

The Investigational Drugs Database Drug Report, Novo/Ontogen, Apr. 14, 2004, pp. 1-3.

The Investigational Drugs Database Drug Report, National Cancer Institute, Mar. 15, 2002, pp. 1-2.

The Investigational Drugs Database Drug Report, Pharmacia Corp, Mar. 24, 2004, pp. 1-2.

The Investigational Drugs Database Drug Report, Abott Laboratories, Apr. 27, 2004, pp. 1-3.

The Investigational Drugs Database Drug Report, F. Hoffmann-La Roche Ltd, Apr. 16, 2004, pp. 1-2.

The Investigational Drugs Database Drug Report, Morphochem AG, Jul. 8, 2003, pp. 1.

The Investigational Drugs Database Drug Report, Wyeth Research, Aug. 16, 2004, pp. 1.

The Investigational Drugs Database Drug Report, Sunesis Pharmaceuticals, Inc, Aug. 16, 2004, pp. 1.

The Investigational Drugs Database Drug Report, Serono Pharma. Research Institute SA, Jul. 6, 2004, pp. 1.

Tobin, et al. "Recent advances in the development of small molecule inhibitors of PTP1B for the treatment of insulin resistance and type 2 diabetes", Curr. Opin. Drug. Discovery. Devel., Jul. 5, 2002, vol. 4, Abstract.

Tremblay, et al., "Beyond the Metabolic Function of PTP1B", Cell Cycle, May 3, 2004, vol. 5, pp. 550-553.

Ueno, et al., "Inhibition of PDGF Beta Receptor Signal Transduction by Coexpression of a Tuncated Receptor", Science, vol. 252, pp. 844-848.

Umezawa, et al., "Molecular design and biological activities of protein-tyrosine phosphatase inhibitors", Pharmacology & Therapeutics, vol. 99, 2003, pp. 15-24.

Valette, et al., "Decomposition Pathways and in Vitro HIV Inhibitory Effects of IsoddA Pronucleotides: Toward a Rational Approach for Intracellular Delivery of Nucleoside 5'-Monophosphates", J. Med. Chem., 1996, vol. 39, pp. 1981-1990.

Van Huijsduijnen, et al., "Prospects for Inhibitors of Protein Tyrosine Phosphatase 1B as Antidiabetic Drugs", J. Med. Chem., 2004, vol. 47, pp. 4142-4146.

Van Huijsduijnen, et al., "Selecting Protein Tyrosine Phosphatases as drug Targets", Drug Discovery Today, Oct. 1, 2002, vol. 7, No. 19, pp. 1013-1019.

Vedejs, et al., "Oxazolium-Derived Azomethine Ylides, External Oxazole Activation and Internal Dipole Trapping in the Synthesis of an Aziridinomitosene", J. Org. Che., 2006, vol. 65, pp. 5498-5505.

Vercauteren, et al., "Improvement of Peripheral Endothelial Dysfunction by Protein Tyrosine Phophatase Inhibitors in Heart Failure", Circulation, Journal of the American Heart Association, 2006, pp. 2498-2507.

Verma, et al., "Nutritional Factors that can Favorably Influence the Glucose/Insulin System: Vanadium", Review Article, Journal of American College of Nutrition, vol. 17, No. 1, pp. 11-18.

Walchli, et al., "Identification of tyrosine phosphatases that Dephosphorylate the insulin receptor", J. of Biol. Chem., vol. 275, No. 13, pp. 9792-9796, 2000.

Wan, et al., "Monocyclic thiophenes as protein tyrosine phosphatase 1B inhibitors: Capturing interactions with Asp48" Bioorganic & Medicinal Chemistry Letters, vol. 16, 2006, pp. 4941-4945.

Wang, et al., "Naphthalenebis {x-x-Difluoromethylenephosphonates] as potent inhibitors of protein tyrosine phosphatases", Bioorganic & Medicinal Chemistry Letters, vol. 8, 1998, pp. 345-350.

Wang, et al. "Structure-based prediction of free energy changes of binding of PTP1B inhibitors", Journal of Computer-Aided Molecular Design, vol. 17, pp. 495-513, 2003.

Wasserman, et al. "The Oxazole-triamide rearrangement. Application to Peptide Synthesis" Tetrahedron Lett., vol. 23, pp. 3831-3834, 1982.

Waring, et al., "PTP1B antisense-treated mice show regulation of genes involved in lipogenesis in liver and fat", Molecular and Cellular Endocrinology, vol. 203, 2003, pp. 155-168.

Watanabe, et al., "Orthovanadate Stimulates cAMP Phophodiesterase 3 Activity in Isolated Rat Hepatocytes through Mitogen-Activated Protein Kinase Activation Dependent on cAMP-Dependent Protein Kinase", Biol. Pharm. Bull., vol. 27, No. 6, pp. 789-796, 2004.

Whitney, et al. "Cycloaddition Reactions of 1,3-Diacetylimidazolin-2-one", Tetrahedron Letters, vol. 22, No. 22, pp. 2063-2066, 1981.

Wiesmann, et al. "Allosteric inhibition of protein tyrosine phosphatase 1B", Nature Structural & Molecular Biology, vol. 11, No. 8, Aug. 2004, pp. 730-737.

Wilson, et al., "Protein Tyrosine Phosphatase 1B Inhibitors: Potency Optimization and In Vivo Efficacy", Poster.

Worm, et al. "The significance of phosphotyrosine phosphatase (PTPase)1B in insulin signalling", Diabetologia, 1999, vol. 42, pp. 1146-1149.

Wrobel, et al., "PTP1B Inhibition and Antihyperglycemic Activity in the ob/ob Mouse Model of Novel 11-Arylbenzo[b]naphtho[2,3-d]furans and 11-Arylbenzo[b]naphtho[2,3-d]thiophenes", J. Med. Chem., 1999, vol. 42, pp. 3199-3202.

Wrobel, et al., "Synthesis and PTP1B Inhibition of Novel 4-Aryl-1-Oxa-9-Thiacyclopenta[b]fluorens", Bioorganic & Medicinal Chemistry Letters, vol. 10, 2000, pp. 1535-1538.

Xiao, et al., "Syp (SH-PTP2) Is a Positive Mediator of Growth Factor-Stimulated Mitogenic Signal Transduction" J. Biol. Chem., vol. 269, pp. 21244-21248, 1994.

Xie, et al., "A two stage click-based Library of protein tyrosine phosphatase inhibitors", Bioorganic & Medicinal Chemistry, vol. 15, 2007, pp. 458-473.

Xie, et al., "Cellular Effects of Small Molecule PTP1B Inhibitors on Insulin Signaling", Biochemistry, 2003, vol. 42, pp. 12792-12804.

Xin, et al., "Identification of a Monoacid-Based, Cell Permeable, Selective Inhibitor of Protein Tyrosine Phosphatase 1B", Bioorganic & Medicinal Chemistry Letters, vol. 13, 2003, pp. 3947-3950.

Xu, et al., "Effects of small interference RNA against PTP1B and TCPTP on insulin signaling pathway in mouse liver: Evidence for non-synergetic cooperation", Cell Biology International, vol. 31, 2007, pp. 88-91.

Xu, et al., "Discovery of potent and selective phenylalanine based dipeptidyl peptidase IV inhibitors", Bioorganic & Medicinal Chemistry Letters, 2005, pp. 2533-2536.

Yamane, et al. HCAPLUS Abstract 133: 112412 "Reversible Thermal Recording Material Containing Aromatic Compound Color Developer", 2000, especially RN 283600-94-2, pp. 1.

Yao, et al., "Structure-Based Design and Synthesis of Small Molecule Protein-Tyrosine Phosphatase 1B Inhibitors", Bioorganic & Medicinal Chemistry, vol. 6, 1998, pp. 1799-1810.

Ye, "Synthesis of a Difluorophosphonomethyl-Containing Phosphatase Inhibitor Designed from the X-ray Structure of a PTP1B-Bound Ligand", Tetrahedron, vol. 52, No. 30, 1996, pp. 9963-9970.

Yeh, et al., "Systematic Review of herbs and Dietary supplements for Glycemic Control in Diabetes", Diabetes Care, vol. 26, No. 4, 2003, pp. 1277-1294.

Yinglin, et al., "A Convenient Synthesis of Primary Amines Using Sodium Diformylamide as A modified Gabriel Reagent", Paper, Synthesis, pp. 122-124, Feb. 1990.

Yokomatsu, "Synthesis and Biological evaluation of x-x-Difuorobenzylphosphonic acid derivatives as small molecular inhibitors of protein-tyrosine phosphatase 1B", Bioorganic & Medicinal Chemistry Letters, vol. 9, 1999, pp. 529-532.

Yudushkin, et al., "Live-Cell Imaging of Enzyme-Substrate Interaction Reveals Spatial Regulation of PTP1B", Science, vol. 315, Jan. 2007, pp. 115-119.

Yu, et al. "A General strategy for the synthesis of Vincamajine-Related Indole Alkaloids: Stereocontrolled Total Synthesis of (+)-Dehydrovoachalotine, (−)-Vincamajinine, and (−)-11-Methoxy-17-epivincamajine as Well as the Related Quebrachidine Diol, Vincamajine Diol, and Vincarinol" J. Org. Chem., 2005, vol. 70, pp. 3963-3979.

Yue, et al., "Isothiazolidinone heterocycles as inhibitors of protein tyrosine phosphatases: Synthesis and Structure-activity relationships of a peptide scaffold", Bioorganic & Medicinal Chemistry, vol. 14, 2006, pp. 5833-5849.

Zasloff, "A Spermine-coupled cholesterol metabolite from the shark with potent appetite suppressant and antidiabetic properties", International Journal of Obesity, 2001, vol. 25, pp. 689-697.

Zerrouki, et al. "Selective Deprotection of Fully Benzoylated Nucleoside Derivatives", Journal of Carbohydrate Chemistry, vol. 23, No. 5, pp. 299-303, 2004.

Zhang, "Protein Tyrosine Phosphatases: Structure and function, substrate specificity, an inhibitor development", Annu Rev. Pharmacol Toxicol, 2002, vol. 42, pp. 209-234, 2001.

Zhang, "Protein Tyrosine Phosphatases: Prospects for Therapeutics", Current Opinion Chem. Bio., Aug. 5, 2001, vol. 4, pp. 416-423.

Zhang, et al., "Ursolice acid and its derivative inhibit protein tyrosine phosphatase 1B, enhancing insulin receptor phosphorlation and stimulating glucose uptake", Biochimica et Biophysica Acta, vol. 1760, 2006, pp. 1505-1512.

Zhang, et al. "Functional studies of protein tyrosine phosphatases with chemical approaches", Biochimica et Biophysica Acta, vol. 1754, 2005, pp. 100-107.

Zhao, et al., "Indoline and Piperazine Containing Derivatives as a Novel Class of Mixed D2/D4 Receptor Antagonist. Part 1: Identification and Structure -Activity Relationships", Bioorganic & Medicinal Chemistry Letters, vol. 12, 2002, pp. 3105-3109.

Zheng, et al., "Cell Transformation and activation of pp60c-src by overexpression of a protein tyrosine phosphatase", Nature, vol. 359, pp. 336-399, Sep. 24, 1992.

Zinker, et al., "PTP1B antisense oligonucleotide lowers PTP1B protein, normalizes blood glucose, and improves insulin sensitivity in diabetic mice", PNAS, Aug. 20, 2002, vol. 99, No. 17, pp. 11357-11362.

Registry No. 186139-09-03 Scifinder, pp. 1-3, Jan. 8, 2007.

* cited by examiner

US 7,381,736 B2

THIAZOLE AND THIADIAZOLE INHIBITORS OF TYROSINE PHOSPHATASES

RELATED APPLICATIONS

Priority is claimed herein under 35 USC 119(e) to U.S. provisional patent application Nos. 60/607,034, filed Sep. 2, 2004; 60/638,447, filed Dec. 22, 2004; and 60/642,292, filed Jan. 6, 2005. The disclosures of the above-referenced applications are incorporated herein by reference in their entirety.

FIELD

Provided herein are thiazole and thiadiazole inhibitors of tyrosine phosphatases. In one embodiment, thiazole, thiadiazole, thiazolidene and thiadiazolidene compounds are provided that are inhibitors of PTP-1B. In another embodiment, provided herein are methods of treatment, prevention, or amelioration of one or more symptoms of diabetes using the compounds and compositions provided herein.

BACKGROUND

Cellular signal transduction is a fundamental mechanism whereby external stimuli that regulate cellular processes are relayed to the interior of cells. The biochemical pathways through which signals are transmitted within cells comprise a circuitry of directly or functionally connected interactive proteins. One of the key biochemical mechanisms of signal transduction involves the reversible phosphorylation of tyrosine residues on proteins. The phosphorylation state of a protein may affect its conformation and/or enzymatic activity as well as its cellular location. The phosphorylation state of a protein is modified through the reciprocal actions of protein tyrosine kinases (PTKs) and protein tyrosine phosphatases (PTPs) at various specific tyrosine residues.

A common mechanism by which receptors regulate cell function is through an inducible tyrosine kinase activity which is either endogenous to the receptor or is imparted by other proteins that become associated with the receptor (Darnell et al., 1994, Science 264:1415-1421; Heldin, 1995, Cell 80:213-223; Pawson, 1995, Nature 373:573-580).

Protein tyrosine kinases comprise a large family of transmembrane receptor and intracellular enzymes with multiple functional domains (Taylor et al., 1992, Ann. Rev. Cell Biol. 8:429-62). The binding of ligand allosterically transduces a signal across the cell membrane where the cytoplasmic portion of the PTKs initiates a cascade of molecular interactions that disseminate the signal throughout the cell and into the nucleus.

Like the PTKs, the protein tyrosine phosphatases (PTPs) comprise a family of transmembrane and cytoplasmic enzymes, possessing at least an approximately 230 amino acid catalytic domain containing a highly conserved active site with the consensus motif >I/V!HCXAGXXR>S/T!G. The substrates of PTPs may be PTKs which possess phosphotyrosine residues or the substrates of PTKs (Hunter, 1989, Cell 58:1013-16; Fischer et al., 1991, Science 253: 401-6; Saito & Streuli, 1991, Cell Growth and Differentiation 2:59-65; Pot and Dixon, 1992, Biochem. Biophys. Acta 1136:35-43).

Transmembrane or receptor-like PTPs (RPTPs) possess an extracellular domain, a single transmembrane domain, and one or two catalytic domains followed by a short cytoplasmic tail. The extracellular domains of these RPTPs are highly divergent, with small glycosylated segments (e.g., RPTPa, RPTPe), tandem repeats of immunoglobulin-like and/or fibronectin type III domains (e.g., LAR) or carbonic anhydrase like domains (e.g., RPTPg, RPTPb). These extracellular features might suggest that these RPTPs function as a receptor on the cell surface, and their enzymatic activity might be modulated by ligands. Intracellular or cytoplasmic PTPs (CPTPs), such as PTP1C, PTP1D, typically contain a single catalytic domain flanked by several types of modular conserved domains. For example, PTP1C, a hemopoietic cell CPTP, is characterized by two Src-homology homology 2 (SH2) domains that recognize short peptide motifs bearing phosphotyrosine (pTyr).

In general, these modular conserved domains influence the intracellular localization of the protein. SH2-containing proteins are able to bind pTyr sites in activated receptors and cytoplasmic phosphoproteins. Another conserved domain known as SH3 binds to proteins with proline-rich regions. A third type known as pleckstrin-homology (PH) domain has also been identified. These modular domains have been found in both CPTKs and CPTPs as well as in non-catalytic adapter molecules, such as Grbs (Growth factor Receptor Bound), which mediate protein-protein interactions between components of the signal transduction pathway (Skolnik et al., 1991, Cell 65:83-90; Pawson, 1995, Nature 373:573-580).

Multiprotein signaling complexes comprising receptor subunits, kinases, phosphatases and adapter molecules are assembled in subcellular compartments through the specific and dynamic interactions between these domains with their binding motifs. Such signaling complexes integrate the extracellular signal from the ligand-bound receptor and relay the signal to other downstream signaling proteins or complexes in other locations inside the cell or in the nucleus (Koch et al., 1991, Science 252:668-674; Pawson, 1994, Nature 373:573-580; Mauro et al., 1994, Trends Biochem Sci 19:151-155; Cohen et al., 1995, Cell 80:237-248).

The levels of tyrosine phosphorylation required for normal cell growth and differentiation at any time are achieved through the coordinated action of PTKs and PTPS. Depending on the cellular context, these two types of enzymes may either antagonize or cooperate with each other during signal transduction. An imbalance between these enzymes may impair normal cell functions leading to metabolic disorders and cellular transformation.

For example, insulin binding to the insulin receptor, which is a PTK, triggers a variety of metabolic and growth promoting effects such as glucose transport, biosynthesis of glycogen and fats, DNA synthesis, cell division and differentiation. Diabetes mellitus, which is characterized by insufficient or a lack of insulin signal transduction, can be caused by any abnormality at any step along the insulin signaling pathway (Olefsky, 1988, in "Cecil Textbook of Medicine," 18th Ed., 2:1360-81).

Relatively less is known with respect to the direct role of tyrosine phosphatases in signal transduction; PTPs may play a role in human diseases. For example, ectopic expression of RPTPa produces a transformed phenotype in embryonic fibroblasts (Zheng et al., Nature 359:336-339), and overexpression of RPTPa in embryonal carcinoma cells causes the cells to differentiate into a cell type with neuronal phenotype (den Hertog et al., EMBO J 12:3789-3798). The gene for human RPTPg has been localized to chromosome 3p21 which is a segment frequently altered in renal and small lung carcinoma. Mutations may occur in the extracellular segment of RPTPg which result in RPTPs that no longer respond to external signals (LaForgia et al., Wary et al., 1993, Cancer Res 52:478-482). Mutations in the gene encoding PTP1C (also known as HCP, SHP) are the cause of the motheaten phenotype in mice which suffer severe immunodeficiency, and systemic autoimmune disease accompanied by hyperproliferation of macrophages (Schultz et al., 1993, Cell 73:1445-1454). PTP1D (also known as Syp or PTP2C) has been shown to bind through SH2 domains to sites of phosphorylation in PDGFR, EGFR and insulin receptor substrate 1 (IRS-1). Reducing the activity of PTP1D by microinjection of anti-PTP1D antibody has been shown to block insulin or EGF-induced mitogenesis (Xiao et al., 1994, *J Biol Chem* 269:21244-21248).

Thus, there is a need for compounds and compositions that modulate the activity of tyrosine phosphatases, including PTP-1B.

SUMMARY

Provided herein are compounds and compositions for modulation of tyrosine phosphatase activity. In one embodiment, compounds and compositions for inhibiting protein tyrosine phosphatase activity are provided. In another embodiment, provided herein are compounds and compositions that are useful in the treatment, prevention, or amelioration of one or more symptoms of diseases caused by dysfunctional signal transduction, or in which dysfunctional signal transduction is implicated. In another embodiment, provided herein are compounds and compositions for treatment, prevention, or amelioration of one or more symptoms of diabetes. In certain embodiments, the compounds provided herein are more active in in vitro and in vivo assays as compared to similar compounds previously disclosed.

In one embodiment, the compounds for use in the compositions and methods provided herein have formula I:

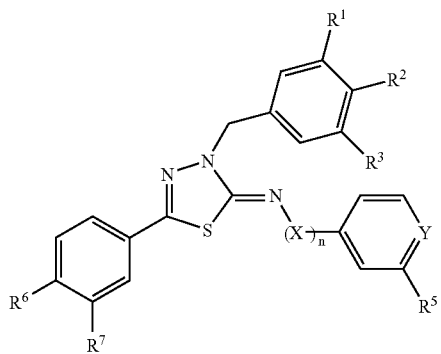

where X is C=O, SO$_2$ or CH$_2$, in one embodiment C=O or CH$_2$;
n is 0 or 1;
R$^1$ is H or halo;
R$^2$ is CF$_2$PO$_3$H$_2$, CF$_2$COOH, OCH(Me)COOH, COOH, CH=CHCOOH, OCH$_2$COOH, cyclopropylene-COOH, tetrazolyl, OC(Me$_2$)COOH or OCF$_2$COOH;
R$^3$ is H, halo or pseudohalo;
Y is N or CR$^4$, where R$^4$ is H, halo or CF$_2$PO$_3$H$_2$;
R$^5$ is H, halo or perhaloalkyl;
R$^6$ is H or alkylsulfonyl; and
R$^7$ is phenoxy which is optionally substituted with COOH or COO-alkyl, or R$^7$ is H, alkylsulfonyl or tetrazolyl.

In another embodiment, the compounds for use in the compositions and methods provided herein have formula II:

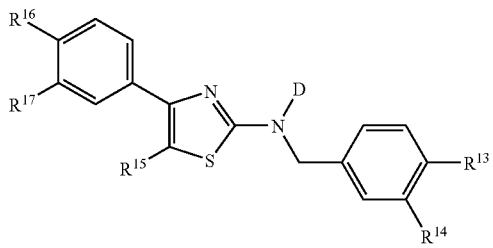

where D is H, alkyl or

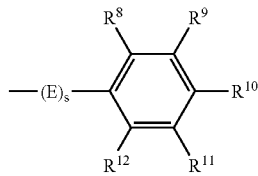

in another embodiment, D is alkyl or

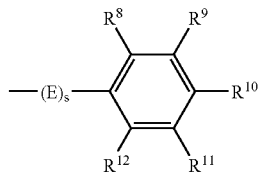

E is CH$_2$ or SO$_2$, in one embodiment CH$_2$;
s is 0 or 1;
R$^8$ and R$^9$ are H, or together form CH=CH—CH=CH;
R$^{10}$ is H, halo, haloalkyl, COOH, alkylsulfonyl, SO$_2$NH$_2$ or COO-alkyl;
R$^{11}$ is H, COOH or halo;
R$^{12}$ is H;
R$^{13}$ is CF$_2$PO$_3$H$_2$, NHC(O)COOH, OCH$_2$COOH, CH=CHCOOH, CF$_2$COOH, COOH, C(O)COOH or 3-COOH-5-isoxazolyl;
R$^{14}$ is halo or COOH;
R$^{15}$ is H, alkyl or CH$_2$CONH$_2$;
R$^{16}$ is NHC(O)COOH, COOH, alkylsulfonyl, NHC(O)COO-alkyl, CH=CH—COOH, H, O(CH$_2$)$_t$COOH, COOMe, O(CH$_2$)$_t$COO-alkyl, 3-COOH-phenyl, OCMe$_2$COOH, S(CH$_2$)$_t$COO-alkyl, S(CH$_2$)$_t$COOH, (CH$_2$)$_t$COOH, SO$_2$(CH$_2$)$_t$COO-alkyl, SO$_2$(CH$_2$)$_t$COOH, OH, C(O)(OCH(H/Me)OC(=O)OiPr, C(O)(OCH(H/Me)OC(=O)tBu or ROCH$_2$CHR'CH$_2$O—C(O), where R is C$_{14-20}$-n-alkyl and R' is H, OH or OMe;
each t is independently 1, 2 or 3; and
R$^{17}$ is H, COO-alkyl, 3-COOH-phenyl, 2-COOH-phenoxy or OCH(Ph)COOH.

In another embodiment, the compounds for use in the compositions and methods provided herein have formula III:

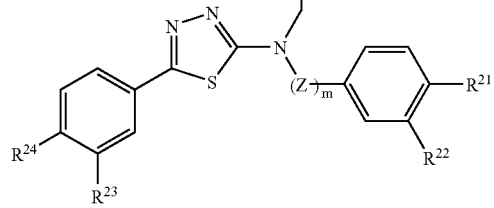

where Z is SO$_2$, CH$_2$ or CO, in another embodiment, Z is CH$_2$;

m is 0 or 1;

$R^{18}$ is H or halo;

$R^{19}$ is $CF_2PO_3H_2$, COOH, NHCOCOOH, $CF_2P(OH)OCH_2OCO$-t-butyl, CH=CH—COOH or 3-COOH-5-isoxazolyl;

$R^{20}$ is H, halo, pseudohalo or COOH;

$R^{21}$ is H, halo, $CF_2PO_3H_2$ or $SO_2$-heterocyclyl;

$R^{22}$ is H or halo;

$R^{23}$ is H or phenoxy optionally substituted with COOH, tetrazolyl, COO-alkyl or alkylsulfonyl; and $R^{24}$ is H or alkylsulfonyl.

In another embodiment, the compounds for use in the compositions and methods provided herein have formula IV:

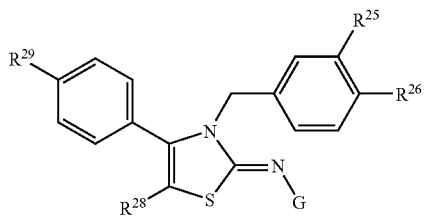

where G is H or

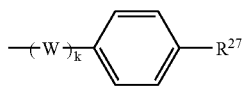

W is CO or $SO_2$, in another embodiment, W is CO;

k is 0 or 1;

$R^{25}$ is H or halo;

$R^{26}$ is $CF_2PO_3H_2$ or $SO_2NH_2$;

$R^{27}$ is H or $SO_2$-heterocyclyl;

$R^{28}$ is H or alkyl; and $R^{29}$ is COO-alkyl, COOH, $COOCH_2OC(O)$-t-Bu or $OCH_2COOH$.

Also provided are pharmaceutically-acceptable derivatives, including salts, esters, enol ethers, enol esters, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-yl-methylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Further provided are pharmaceutical compositions containing the compounds provided herein and a pharmaceutically acceptable carrier. In one embodiment, the pharmaceutical compositions are formulated for single dosage administration.

Methods of modulating protein tyrosine phosphatase, including PTP-1B, using the compounds and compositions provided herein are provided. Further provided are methods of inhibiting protein tyrosine phosphatase, including PTP-1B, using the compounds and compositions provided herein. Also provided are methods of increasing insulin sensitivity using the compounds and compositions provided herein. Methods of treating, preventing, or ameliorating one or more symptoms of protein tyrosine phosphatase, including PTP-1B, mediated diseases are also provided.

Protein tyrosine phosphatase, including PTP-1B, mediated diseases and disorders include, but are not limited to, diabetes including Type 1 and Type 2 diabetes (and associated complications such as hypertension, ischemic diseases of the large and small blood vessels, blindness, circulatory problems, kidney failure and atherosclerosis), syndrome X, metabolic syndrome, glucose intolerance, insulin resistance, leptin resistance, obesity, cancer, neurodegenerative diseases, and other diseases in which the activity of a tyrosine phosphatase or multiple tyrosine phosphatases contributes to the symptoms or pathology thereof.

In practicing the methods, effective amounts of the compounds or compositions containing therapeutically effective concentrations of the compounds are administered.

Articles of manufacture are provided containing packaging material, a compound or composition provided herein which is useful for treating, preventing, or ameliorating one or more symptoms of protein tyrosine phosphatase, including PTP-1B, mediated diseases or disorders, and a label that indicates that the compound or composition is useful for treating, preventing, or ameliorating one or more symptoms of protein tyrosine phosphatase, including PTP-1B, mediated diseases or disorders.

DETAILED DESCRIPTION

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, protein tyrosine phosphatase (PTP) refers to an enzyme of the PTP class, including enzymes that are both tyrosine-specific and dual-specific in their phoshpatase activity. In one embodiment, such phosphatases encompass both transmembrane receptor-like PTPs (RPTPs) as well as soluble cytosolic proteins. RPTPs include small glycosylated segments (e.g., RPTPa, RPTPe), tandem repeats of immunoglobulin-like and/or fibronectin type III domains (e.g., LAR) or carbonic anhydrase like domains (e.g., RPTPg, RPTPb). Intracellular or cytoplasmic PTPs (CPTPs), include PTP1B or PTP-1B, PTP1C and PTP1D, and typically contain a single catalytic domain flanked by several types of modular conserved domains.

As used herein, protein tyrosine phosphatase 1B (PTP-1B) refers to a 37-kD protein comprised of a single domain, is topologically organized into 8 alpha helices and 12 beta sheets. See, e.g., Jia, Z., Barford, D., Flint, A. J., and N. K. Tonks (1995) *Science* 268:1754-1758; Pannifer A., Flint A., Tonks N., and Barford D. (1998) *The Journal of Biological Chemistry* 273:10454-10462.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating diseases or disorders in which α-synuclein fibril formation is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response, such as modulation of α-synuclein fibril formation, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392). Other prodrugs for use herein are described elsewhere herein.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, "alkyl," "alkenyl" and "alkynyl" carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl(propenyl) and propargyl(propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—. As used herein, "sulfonyl" or "sulfuryl" refers to —S(O)$_2$—. As used herein, "sulfo" refers to —S(O)$_2$O—.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "diarylaminocarbonyl" refers to —C(O)NRR' in which R and R' are independently selected from aryl, including lower aryl, such as phenyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(=O) and S(=O)$_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)$_n$—NR—(CRR)$_m$—, where n and m are each independently an integer from 0 to 4. As used herein, "oxaalkylene" refers to —(CRR)$_n$—O—(CRR)$_m$—, where n and m are each independently an integer from 0 to 4. As used herein, "thiaalkylene" refers to —(CRR)$_n$—S—(CRR)$_m$—, —(CRR)$_n$—S (=O)—(CRR)$_m$—, and —(CRR)$_n$—S(=O)$_2$—(CRR)$_m$—, where n and m are each independently an interger from 0 to 4.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH—CH=CH— and —CH=CH—CH$_2$—. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and —C≡C—CH$_2$—. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulfur or substituted or unsubstituted nitrogen atoms, where the nitrogen substituent is alkyl. Alk(en)(yn)ylene groups include, but are not limited to, —C=C—(CH$_2$)$_n$—C≡C—, where n is 1 or 2. The term "lower alk(en)(yn)ylene" refers to alk(en)(yn)ylene groups having up to 6 carbons. In certain embodiments, alk(en)(yn) ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn) ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from Q1.

As used herein, "alkylidene" refers to a divalent group, such as =CR'R", which is attached to one atom of another group, forming a double bond. Alkylidene groups include, but are not limited to, methylidene (=CH$_2$) and ethylidene (=CHCH$_3$). As used herein, "arylalkylidene" refers to an alkylidene group in which either R' or R" is an aryl group. "Cycloalkylidene" groups are those where R' and R" are linked to form a carbocyclic ring. "Heterocyclylid-ene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "semicarbazide" refers to —NHC(O) NHNH—. "Carbazate" refers to the divalent group —OC (O)NHNH—. "Isothiocarbazate" refers to the divalent group —SC(O)NHNH—. "Thiocarbazate" refers to the divalent group —OC(S)NHNH—. "Sulfonylhydrazide" refers to the divalent group —SO$_2$NHNH—. "Hydrazide" refers to the divalent group —C(O)NHNH—. "Azo" refers to the divalent group —N=N—. "Hydrazinyl" refers to the divalent group —NH—NH—.

Where the number of any given substituent is not specified (e.g., haloalkyl), there may be one or more substituents present. For example, "haloalkyl" may include one or more of the same or different halogens.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Compounds

The compounds provided herein exhibit activity in assays that measure protein tyrosine phosphatase activity, in particular PTP-1B activity. In certain embodiments, the compounds provided herein are more active in in vitro and in vivo assays as compared to similar compounds previously disclosed. In other embodiments, the compounds provided herein exhibit improved pharmacokinetic properties, stability, and/or tolerability (e.g., toxicity) as compared to similar compounds previously disclosed.

In one embodiment, the compounds for use in the compositions and methods provided herein have formula I:

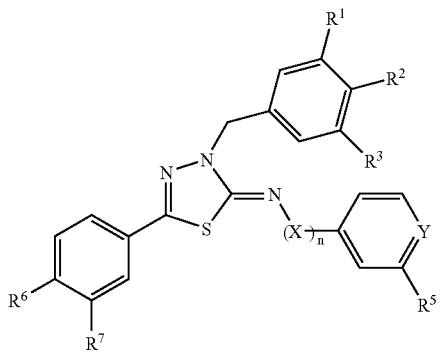

where X is C=O, SO$_2$ or CH$_2$, in another embodiment, X is C=O or CH$_2$;
n is 0 or 1;
R$^1$ is H or Br;
R$^2$ is CF$_2$PO$_3$H$_2$, CF$_2$COOH, OCH(Me)COOH, COOH, CH=CHCOOH, OCH$_2$COOH, cyclopropylene-COOH, tetrazolyl, OC(Me$_2$)COOH or OCF$_2$COOH;
R$^3$ is H, F, Cl, Br or CN;
Y is N or CR$^4$, where R$^4$ is H, Cl or CF$_2$PO$_3$H$_2$;
R$^5$ is H, Cl or CF$_3$;
R$^6$ is H or methanesulfonyl; and
R$^7$ is phenoxy which is optionally substituted with COOH or COOMe, or R$^7$ is H, methanesulfonyl or tetrazolyl.
In another embodiment, R$^1$ is H or Br.
In another embodiment, R$^2$ is CF$_2$PO$_3$H$_2$.
In another embodiment, R$^3$ is Br, CN or Cl.
In another embodiment, R$^4$ is H, Cl or CF$_2$PO$_3$H$_2$.
In another embodiment, R$^5$ is H, Cl or CF$_3$.
In another embodiment, R$^6$ is H or methanesulfonyl.
In another embodiment, R$^7$ is phenoxy which is optionally substituted with COOH, or R$^7$ is H or methanesulfonyl.
In another embodiment, the compounds of formula I are:
3-(3-{5-Benzoylimino-4-[3-bromo-4-(difluoro-phosphono-methyl)-benzyl]-4,5-dihydro-[1,3,4]thiadiazol-2-yl}-phenoxy)-benzoic acid;

3-{3-[4-[3-Bromo-4-(difluoro-phosphono-methyl)-benzyl]-5-(3,4-dichloro-benzoylimino)-4,5-dihydro-[1,3,4]thiadiazol-2-yl]-phenoxy}-benzoic acid;
3-{3-[4-[3-Bromo-4-(difluoro-phosphono-methyl)-benzyl]-5-(3-trifluoromethyl-benzoylimino)-4,5-dihydro-[1,3,4]thiadiazol-2-yl]-phenoxy}-benzoic acid;
3-{3-[4-[3-Bromo-4-(difluoro-phosphono-methyl)-benzyl]-5-(3-chloro-phenylimino)-4,5-dihydro-[1,3,4]thiadiazol-2-yl]-phenoxy}-benzoic acid;
3-(3-{4-[3-Bromo-4-(difluoro-phosphono-methyl)-benzyl]-5-phenylimino-4,5-dihydro-[1,3,4]thiadiazol-2-yl}-phenoxy)-benzoic acid;
3-{3-[4-[3-Bromo-4-(difluoro-phosphono-methyl)-benzyl]-5-(3,4-dichloro-phenylimino)-4,5-dihydro-[1,3,4]thiadiazol-2-yl]-phenoxy}-benzoic acid;
3-{3-[4-[3-Bromo-4-(difluoro-phosphono-methyl)-benzyl]-5-(4-chloro-phenylimino)-4,5-dihydro-[1,3,4]thiadiazol-2-yl]-phenoxy}-benzoic acid;
3-{3-[4-[3-Chloro-4-(difluoro-phosphono-methyl)-benzyl]-5-(3,4-dichloro-phenylimino)-4,5-dihydro-[1,3,4]thiadiazol-2-yl]-phenoxy}-benzoic acid;
3-{3-[4-[3-Chloro-4-(difluoro-phosphono-methyl)-benzyl]-5-(3,4-dichloro-phenylimino)-4,5-dihydro-[1,3,4]thiadiazol-2-yl]-phenoxy}-benzoic acid methyl ester;
3-(3-{5-(3,4-Dichloro-phenylimino)-4-[4-(difluoro-phosphono-methyl)-3-fluoro-benzyl]-4,5-dihydro-[1,3,4]thiadiazol-2-yl}-phenoxy)-benzoic acid;
3-(3-{5-(3,4-Dichloro-phenylimino)-4-[4-(difluoro-phosphono-methyl)-3-fluoro-benzyl]-4,5-dihydro-[1,3,4]thiadiazol-2-yl}-phenoxy)-benzoic acid methyl ester;
3-{3-[4-[3-Bromo-4-(difluoro-phosphono-methyl)-benzyl]-5-(3,4-dichloro-phenylimino)-4,5-dihydro-[1,3,4]thiadiazol-2-yl]-phenoxy}-benzoic acid methyl ester;
3-{3-[4-[3-Cyano-4-(difluoro-phosphono-methyl)-benzyl]-5-(3,4-dichloro-phenylimino)-4,5-dihydro-[1,3,4]thiadiazol-2-yl]-phenoxy}-benzoic acid;
({2-Bromo-4-[2-[4-(difluoro-phosphono-methyl)-benzylimino]-5-(3-phenoxy-phenyl)-[1,3,4]thiadiazol-3-ylmethyl]-phenyl}-difluoro-methyl)-phosphonic acid;
({2-Bromo-4-[2-(3,4-dichloro-phenylimino)-5-(4-methanesulfonyl-phenyl)-[1,3,4]thiadiazol-3-ylmethyl]-phenyl}-difluoro-methyl)-phosphonic acid;
[(2-Bromo-4-{2-(3,4-dichloro-phenylimino)-5-[3-(3-methanesulfonyl-phenoxy)-phenyl]-[1,3,4]thiadiazol-3-ylmethyl}-phenyl)-difluoro-methyl]-phosphonic acid;
3-{3-[4-[3,5-Dibromo-4-(difluoro-phosphono-methyl)-benzyl]-5-(3,4-dichloro-phenylimino)-4,5-dihydro-[1,3,4]thiadiazol-2-yl]-phenoxy}-benzoic acid;
3-(3-{5-(3,4-Dichloro-phenylimino)-4-[4-(difluoro-phosphono-methyl)-benzyl]-4,5-dihydro-[1,3,4]thiadiazol-2-yl}-phenoxy)-benzoic acid;
3-{3-[4-[4-(Carboxy-difluoro-methyl)-benzyl]-5-(3,4-dichloro-phenylimino)-4,5-dihydro-[1,3,4]thiadiazol-2-yl]-phenoxy}-benzoic acid;
3-{3-[4-[3-Bromo-4-(1-carboxy-ethoxy)-benzyl]-5-(3,4-dichloro-phenylimino)-4,5-dihydro-[1,3,4]thiadiazol-2-yl]-phenoxy}-benzoic acid;
2-Bromo-4-[5-[3-(3-carboxy-phenoxy)-phenyl]-2-(3,4-dichloro-phenylimino)-[1,3,4]thiadiazol-3-ylmethyl]-benzoic acid;
3-(3-{5-Benzoylimino-4-[3-bromo-4-(2-carboxy-vinyl)-benzyl]-4,5-dihydro-[1,3,4]thiadiazol-2-yl}-phenoxy)-benzoic acid;
3-{3-[4-(3-Bromo-4-carboxymethoxy-benzyl)-5-(pyridine-4-carbonylimino)-4,5-dihydro-[1,3,4]thiadiazol-2-yl]-phenoxy}-benzoic acid;

3-{3-[4-[3-Bromo-4-(carboxy-difluoro-methyl)-benzyl]-5-(3,4-dichloro-phenylimino)-4,5-dihydro-[1,3,4]thiadiazol-2-yl]-phenoxy}-benzoic acid;

3-{3-[4-[3-Bromo-4-(2-carboxy-cyclopropyl)-benzyl]-5-(3,4-dichloro-phenylimino)-4,5-dihydro-[1,3,4]thiadiazol-2-yl]-phenoxy}-benzoic acid;

(3-[3-Bromo-4-(1H-tetrazol-5-yl)-benzyl]-5-{3-[3-(1H-tetrazol-5-yl)-phenoxy]-phenyl}-3H-[1,3,4]thiadiazol-2-ylidene)-(3,4-dichloro-phenyl)-amine;

({4-[2-(3,4-Dichloro-phenylimino)-5-(3-m-tolyloxy-phenyl)-[1,3,4]thiadiazol-3-ylmethyl]-phenyl}-difluoro-methyl)-phosphonic acid;

3-{3-[4-[3-Bromo-4-(1-carboxy-1-methyl-ethoxy)-benzyl]-5-(3,4-dichloro-phenylimino)-4,5-dihydro-[1,3,4]thiadiazol-2-yl]-phenoxy}-benzoic acid;

3-{3-[4-[3-Bromo-4-(carboxy-difluoro-methoxy)-benzyl]-5-(3,4-dichloro-phenylimino)-4,5-dihydro-[1,3,4]thiadiazol-2-yl]-phenoxy}-benzoic acid;

3-{3-[4-[3-Bromo-4-(1H-tetrazol-5-yl)-benzyl]-5-(3,4-dichloro-phenylimino)-4,5-dihydro-[1,3,4]thiadiazol-2-yl]-phenoxy}-benzoic acid;

3-(3-{5-Benzoylimino-4-[3-bromo-4-(difluoro-phosphono-methyl)-benzyl]-4,5-dihydro-[1,3,4]thiadiazol-2-yl}-phenoxy)-benzoic acid methyl ester;

3-{3-[4-[3-Bromo-4-(difluoro-phosphono-methyl)-benzyl]-5-(pyridine-4-carbonylimino)-4,5-dihydro-[1,3,4]thiadiazol-2-yl]-phenoxy}-benzoic acid methyl ester; or 3-{3-[4-[3-Bromo-4-(difluoro-phosphono-methyl)-benzyl]-5-(pyridine-4-carbonylimino)-4,5-dihydro-[1,3,4]thiadiazol-2-yl]-phenoxy}-benzoic acid.

In another embodiment, the compounds for use in the compositions and methods provided herein have formula II:

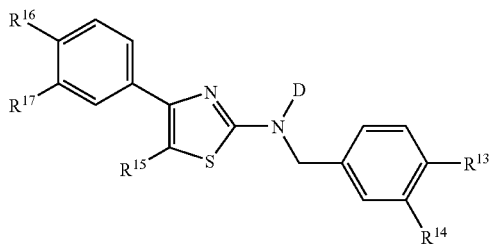

where D is H, methyl or

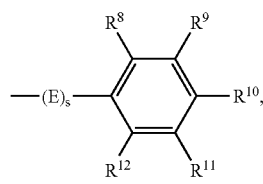

in another embodiment, D is methyl or

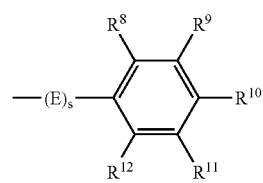

E is $CH_2$ or $SO_2$, in another embodiment E is $CH_2$;
s is 0 or 1;
$R^8$ and $R^9$ are H, or together form $CH=CH-CH=CH$;
$R^{10}$ is H, Cl, $CF_3$, COOH, $SO_2Me$, $SO_2NH_2$ or COOEt;
$R^{11}$ is H, COOH or Cl;
$R^{12}$ is H;
$R^{13}$ is $CF_2PO_3H_2$, NHC(O)COOH, $OCH_2COOH$, $CH=CHCOOH$, $CF_2COOH$, COOH, C(O)COOH or 3-COOH-5-isoxazolyl;
$R^{14}$ is Cl, Br or COOH;
$R^{15}$ is H, $CH_2CONH_2$ or Me;
$R^{16}$ is NHC(O)COOH, COOH, methanesulfonyl, NHC(O)COOEt, $CH=CH-COOH$, H, $OCH_2COOH$, COOMe, $OCH_2COOEt$, 3-COOH-phenyl, $OCMe_2COOH$, $SCH_2COOMe$, $SCH_2COOH$, $CH_2CH_2COOH$, $SO_2CH_2COOMe$, $SO_2CH_2COOH$, OH or C(O)OCH(Me)OCOO-i-Pr; and
$R^{17}$ is H, COOMe, 3-COOH-phenyl, 2-COOH-phenoxy or OCH(Ph)COOH.

In another embodiment, $R^8$ and $R^9$ are H, or together form $CH=CH-CH=CH$.

In another embodiment, $R^{10}$ is H, Cl, $CF_3$, COOH, $SO_2Me$, $SO_2NH_2$ or COOEt.

In another embodiment, $R^{11}$ is H, COOH or Cl.

In another embodiment, $R^{13}$ is $CF_2PO_3H_2$.

In another embodiment, $R^{14}$ is Br.

In another embodiment, $R^{15}$ is H, $CH_2CONH_2$ or Me.

In another embodiment, $R^{16}$ is NHC(O)COOH, COOH, methanesulfonyl, NHC(O)COOEt, $CH=CH-COOH$, H, $OCH_2COOH$, COOMe, $OCH_2COOEt$, 3-COOH-phenyl, $OCMe_2COOH$, $SCH_2COOMe$, $SCH_2COOH$, $CH_2CH_2COOH$, $SO_2CH_2COOMe$, $SO_2CH_2COOH$, OH or C(O)OCH(Me)OCOO-i-Pr.

In another embodiment, $R^{17}$ is H, COOMe, 3-COOH-phenyl, 2-COOH-phenoxy or OCH(Ph)COOH.

In another embodiment, the compounds of formula II are:

N-(4-{2-[[3-Bromo-4-(difluoro-phosphono-methyl)-benzyl]-(3,4-dichloro-phenyl)-amino]-thiazol-4-yl}-phenyl)-oxalamic acid;

(3-{2-[[3-Bromo-4-(difluoro-phosphono-methyl)-benzyl]-(3,4-dichloro-phenyl)-amino]-thiazol-4-yl}-phenoxy)-phenyl-acetic acid;

4-{2-[[3-Bromo-4-(difluoro-phosphono-methyl)-benzyl]-(4'-carboxyphenyl amino]-thiazol-4-yl}-benzoic acid;

4-{2-[[3-Bromo-4-(difluoro-phosphono-methyl)-benzyl]-(4-trifluoromethyl-phenyl)-amino]-thiazol-4-yl}-benzoic acid;

4-{2-[[3-Bromo-4-(difluoro-phosphono-methyl)-benzyl]-(3,4-dichloro-phenyl)-amino]-thiazol-4-yl}-benzoic acid;

{[2-Bromo-4-({[4-(4-methanesulfonyl-phenyl)-thiazol-2-yl]-phenyl-amino}-methyl)-phenyl]-difluoro-methyl}-phosphonic acid;

N-[4-(2-{[3-Bromo-4-(difluoro-phosphono-methyl)-benzyl]-phenyl-amino}-thiazol-4-yl)-phenyl]-oxalamic acid ethyl ester;

{[2-Bromo-4-({(3,4-dichloro-phenyl)-[4-(4-methanesulfonyl-phenyl)-thiazol-2-yl]-amino}-methyl)-phenyl]-difluoro-methyl}-phosphonic acid;

N-(4-{2-[[3-Bromo-4-(difluoro-phosphono-methyl)-benzyl]-(3,4-dichloro-phenyl)-amino]-thiazol-4-yl}-phenyl)-oxalamic acid ethyl ester;

4-(2-{[3-Bromo-4-(difluoro-phosphono-methyl)-benzyl]-naphthalen-1-yl-amino}-thiazol-4-yl)-benzoic acid;

3-(4-{2-[[3-Bromo-4-(difluoro-phosphono-methyl)-benzyl]-(3,4-dichloro-phenyl)-amino]-thiazol-4-yl}-phenyl)-acrylic acid;

(4-{2-[[3-Bromo-4-(difluoro-phosphono-methyl)-benzyl]-(3,4-dichloro-phenyl)-amino]-5-methyl-thiazol-4-yl}-phenoxy)-acetic acid;

4-{2-[[3-Bromo-4-(difluoro-phosphono-methyl)-benzyl]-(4'-ethoxycarbonylphenyl amino]-thiazol-4-yl}-benzoic acid methyl ester;

4-{2-[[3-Bromo-4-(difluoro-phosphono-methyl)-benzyl]-(4-trifluoromethyl-phenyl)amino]-thiazol-4-yl}-benzoic acid methyl ester;

4-(2-{[3-Bromo-4-(difluoro-phosphono-methyl)-benzyl]-naphthalen-1-yl-amino}-thiazol-4-yl)-benzoic acid methyl ester;

5-{2-[[3-Bromo-4-(difluoro-phosphono-methyl)-benzyl]-(3,4-dichloro-phenyl)-amino]-thiazol-4-yl}-2-hydroxy-benzoic acid methyl ester;

[(2-Bromo-4-{[(3,4-dichloro-phenyl)-(4-phenyl-thiazol-2-yl)-amino]-methyl}-phenyl)-difluoro-methyl]-phosphonic acid;

(4-{2-[[3-Bromo-4-(difluoro-phosphono-methyl)-benzyl]-(3,4-dichloro-phenyl)-amino]-5-methyl-thiazol-4-yl}-phenoxy)-acetic acid ethyl ester;

4-{2-[[3-Bromo-4-(difluoro-phosphono-methyl)-benzyl]-(3,4-dichloro-phenyl)-amino]-thiazol-4-yl}-benzoic acid methyl ester;

[(2-Bromo-4-{[(3,4-dichloro-phenyl)-(4-naphthalen-2-yl-thiazol-2-yl)-amino]methyl}-phenyl)-difluoro-methyl]-phosphonic acid;

[2-Bromo-4-({(3,4-dichloro-phenyl)-[4-(4-methanesulfonyl-phenyl)-thiazol-2-yl]-amino}-methyl)-phenoxy]-acetic acid;

3-[2-Bromo-4-({(3,4-dichloro-phenyl)-[4-(4-methanesulfonyl-phenyl)-thiazol-2-yl]-amino}-methyl)-phenyl]-acrylic acid;

4-({(3,4-Dichloro-phenyl)-[4-(4-methanesulfonyl-phenyl)-thiazol-2-yl]-amino}-methyl)-phenyl]-difluoro-acetic acid;

3-{3-[4-[3-Bromo-4-(difluoro-phosphono-methyl)-benzyl]-5-(3-trifluoromethyl-benzoylimino)-4,5-dihydro-[1,3,4]thiadiazol-2-yl]-phenoxy}-benzoic acid;

4-{2-[(3-Bromo-4-carboxymethoxy-benzyl)-(3,4-dichloro-phenyl)-amino]-thiazol-4-yl}-benzoic acid;

2-Bromo-4-{[[4-(4-carboxy-phenyl)-thiazol-2-yl]-(3,4-dichloro-phenyl)-amino]-methyl}-benzoic acid;

N-[4-(2-{[3-Bromo-4-(difluoro-phosphono-methyl)-benzyl]-phenyl-amino}-thiazol-4-yl)-phenyl]-oxalamic acid;

[(4-{[(3,4-Dichloro-phenyl)-(4-phenyl-thiazol-2-yl)-amino]-methyl}-phenyl)-difluoro-methyl]-phosphonic acid;

5-({(3,4-Dichloro-phenyl)-[4-(4-methanesulfonyl-phenyl)-thiazol-2-yl]-amino}-methyl)-2-(oxalyl-amino)-benzoic acid;

5-(4-{[[4-(4-Carboxy-phenyl)-thiazol-2-yl]-(3,4-dichloro-phenyl)-amino]-methyl}-phenyl)-isoxazole-3-carboxylic acid;

4-{2-[(3,4-Dichloro-phenyl)-(4-oxalyl-benzyl)-amino]-thiazol-4-yl}-benzoic acid;

4-(2-{[3-Bromo-4-(difluoro-phosphono-methyl)-benzyl]-methyl-amino}-thiazol-4-yl)-benzoic acid;

4'-{2-[[3-Bromo-4-(difluoro-phosphono-methyl)-benzyl]-(3,4-dichloro-phenyl)-amino]-thiazol-4-yl}-biphenyl-3-carboxylic acid;

3'-{2-[[3-Bromo-4-(difluoro-phosphono-methyl)-benzyl]-(3,4-dichloro-phenyl)-amino]-thiazol-4-yl}-biphenyl-3-carboxylic acid;

2-(3-{2-[[3-Bromo-4-(difluoro-phosphono-methyl)-benzyl]-(3,4-dichloro-phenyl)-amino]-thiazol-4-yl}-phenoxy)-benzoic acid;

4-({[3-Bromo-4-(difluoro-phosphono-methyl)-benzyl]-[4-(4-methanesulfonyl-phenyl)-thiazol-2-yl]-amino}-methyl)-benzoic acid methyl ester;

4-({[3-Bromo-4-(difluoro-phosphono-methyl)-benzyl]-[4-(4-methanesulfonyl-phenyl)-thiazol-2-yl]-amino}-methyl)-benzoic acid;

(3-{2-[[3-Bromo-4-(difluoro-phosphono-methyl)-benzyl]-(3,4-dichloro-phenyl)-amino]-thiazol-4-yl}-phenoxy)-acetic acid;

2-(3-{2-[[3-Bromo-4-(difluoro-phosphono-methyl)-benzyl]-(3,4-dichloro-phenyl)-amino]-thiazol-4-yl}-phenoxy)-2-methyl-propionic acid;

4-(2-{Benzenesulfonyl-[3-bromo-4-(difluoro-phosphono-methyl)-benzyl]-amino}-thiazol-4-yl)-benzoic acid methyl ester;

4-(2-{Benzenesulfonyl-[3-bromo-4-(difluoro-phosphono-methyl)-benzyl]-amino}-thiazol-4-yl)-benzoic acid;

(4-{2-[[3-Bromo-4-(difluoro-phosphono-methyl)-benzyl]-(3,4-dichloro-phenyl)-amino]-thiazol-4-yl}-phenylsulfanyl)-acetic acid methyl ester;

(4-{2-[[3-Bromo-4-(difluoro-phosphono-methyl)-benzyl]-(3,4-dichloro-phenyl)-amino]-thiazol-4-yl}-phenylsulfanyl)-acetic acid;

[(2-Bromo-4-{[[5-carbamoylmethyl-4-(4-methanesulfonyl-phenyl)-thiazol-2-yl]-(3,4-dichloro-phenyl)-amino]-methyl}-phenyl)-difluoro-methyl]-phosphonic acid;

[(2-Bromo-4-{[[4-(4-methanesulfonyl-phenyl)-thiazol-2-yl]-(4-sulfamoyl-benzyl)-amino]-methyl}-phenyl)-difluoro-methyl]-phosphonic acid;

3-(4-{2-[[3-Bromo-4-(difluoro-phosphono-methyl)-benzyl]-(3,4-dichloro-phenyl)-amino]-thiazol-4-yl}-phenyl)-propionic acid;

{[2-Chloro-4-({(3,4-dichloro-phenyl)-[4-(4-methanesulfonyl-phenyl)-thiazol-2-yl]-amino}-methyl)-phenyl]-difluoro-methyl}-phosphonic acid;

(4-{2-[[3-Bromo-4-(difluoro-phosphono-methyl)-benzyl]-(3,4-dichloro-phenyl)-amino]-thiazol-4-yl}-benzenesulfonyl)-acetic acid methyl ester;

(4-{2-[[3-Bromo-4-(difluoro-phosphono-methyl)-benzyl]-(3,4-dichloro-phenyl)-amino]-thiazol-4-yl}-benzenesulfonyl)-acetic acid;

(4-{2-[[3-Bromo-4-(difluoro-phosphono-methyl)-benzyl]-(3,4-dichloro-phenyl)-amino]-thiazol-4-yl}-phenoxy)-acetic acid;

(4-{2-[[3-Bromo-4-(difluoro-phosphono-methyl)-benzyl]-(3,4-dichloro-phenyl)-amino]-thiazol-4-yl}-phenoxy)-acetic acid;

(4-{2-[[3-Bromo-4-(difluoro-phosphono-methyl)-benzyl]-(3,4-dichloro-phenyl)-amino]-thiazol-4-yl}-phenoxy)-acetic acid;

4-{3-[3-Bromo-4-(difluoro-phosphono-methyl)-benzyl]-2-imino-2,3-dihydro-thiazol-4-yl}-benzoic acid 2,2-dimethyl-propionyloxymethyl ester; or 4-[3-(3-Bromo-4-{[(2,2-dimethyl-propionyloxymethoxy)-hydroxy-phosphoryl]-difluoro-methyl}-benzyl)-2-imino-2,3-dihydro-thiazol-4-yl]-benzoic acid.

In another embodiment, the compounds for use in the compositions and methods provided herein have formula III:

where Z is SO$_2$, CH$_2$ or CO, in another embodiment Z is CH$_2$;

m is 0 or 1;

R$^{18}$ is H or Br;

R$^{19}$ is CF$_2$PO$_3$H$_2$, COOH, NHCOCOOH, CF$_2$P(OH)OCH$_2$OCO-t-butyl, CH=CH—COOH or 3-COOH-5-isoxazolyl;

R$^{20}$ is H, Br, CN, Cl or COOH;

R$^{21}$ is H, Cl, CF$_2$PO$_3$H$_2$ or SO$_2$-1-piperidinyl;

R$^{22}$ is H or Cl;

R$^{23}$ is H or phenoxy optionally substituted with COOH, tetrazolyl, COOMe or methanesulfonyl; and R$^{24}$ is H or methanesulfonyl.

In another embodiment, Z is SO$_2$ or CH$_2$. In another embodiment, Z is CH$_2$.

In another embodiment, R$^{18}$ is H or Br.

In another embodiment, R$^{19}$ is CF$_2$PO$_3$H$_2$.

In another embodiment, R$^{20}$ is Br, CN or Cl.

In another embodiment, R$^{21}$ is H, Cl, CF$_2$PO$_3$H$_2$ or SO$_2$-1-piperidinyl.

In another embodiment, R$^{22}$ is H or Cl.

In another embodiment, R$^{23}$ is H or phenoxy optionally substituted with COOH, tetrazolyl, COOMe or methanesulfonyl.

In another embodiment, R$^{24}$ is H or methanesulfonyl.

In another embodiment, the compounds of formula III are:

[(2-Bromo-4-{[(3,4-dichloro-phenyl)-(5-{3-[3-(1H-tetrazol-5-yl)-phenoxy]-phenyl}-[1,3,4]thiadiazol-2-yl)-amino]-methyl}-phenyl)-difluoro-methyl]-phosphonic acid;

3-(3-{5-[[3-Bromo-4-(difluoro-phosphono-methyl)-benzyl]-(3,4-dichloro-phenyl)-amino]-[1,3,4]thiadiazol-2-yl}-phenoxy)-benzoic acid;

3-(3-{5-[[3-Bromo-4-(difluoro-phosphono-methyl)-benzyl]-(4-chloro-phenyl)-amino]-[1,3,4]thiadiazol-2-yl}-phenoxy)-benzoic acid;

3-[3-(5-{[3-Bromo-4-(difluoro-phosphono-methyl)-benzyl]-phenyl-amino}-[1,3,4]thiadiazol-2-yl)-phenoxy]-benzoic acid;

3-(3-{5-[[3-Bromo-4-(difluoro-phosphono-methyl)-benzyl]-(3-chloro-phenyl)-amino]-[1,3,4]thiadiazol-2-yl}-phenoxy)-benzoic acid;

3-(3-{5-[[3-Chloro-4-(difluoro-phosphono-methyl)-benzyl]-(3,4-dichloro-phenyl)-amino]-[1,3,4]thiadiazol-2-yl}-phenoxy)-benzoic acid;

3-(3-{5-[[3-Bromo-4-(difluoro-phosphono-methyl)-benzyl]-(3,4-dichloro-phenyl)-amino]-[1,3,4]thiadiazol-2-yl}-phenoxy)-benzoic acid methyl ester;

3-(3-{5-[[3-Chloro-4-(difluoro-phosphono-methyl)-benzyl]-(3,4-dichloro-phenyl)-amino]-[1,3,4]thiadiazol-2-yl}-phenoxy)-benzoic acid methyl ester;

3-[3-(5-{[3-Bromo-4-(difluoro-phosphono-methyl)-benzyl]-[4-(piperidine-1-sulfonyl)-phenyl]-amino}-[1,3,4]thiadiazol-2-yl)-phenoxy]-benzoic acid;

3-{3-[4-[3-Chloro-4-(difluoro-phosphono-methyl)-benzyl]-5-(3,4-dichloro-phenylimino)-4,5-dihydro-[1,3,4]thiadiazol-2-yl]-phenoxy}-benzoic acid;

3-(3-{5-[[3-Cyano-4-(difluoro-phosphono-methyl)-benzyl]-(3,4-dichloro-phenyl)-amino]-[1,3,4]thiadiazol-2-yl}-phenoxy)-benzoic acid;

3-[3-(5-{Benzyl-[3-bromo-4-(difluoro-phosphono-methyl)-benzyl]-amino}-[1,3,4]thiadiazol-2-yl)-phenoxy]-benzoic acid;

3-(3-{5-[{3-Bromo-4-[difluoro-(hydroxy-methoxy-phosphoryl)-methyl]-benzyl}-(3,4-dichloro-phenyl)-amino]-[1,3,4]thiadiazol-2-yl}-phenoxy)-benzoic acid;

{[2-Bromo-4-({(3,4-dichloro-phenyl)-[5-(4-methanesulfonyl-phenyl)-[1,3,4]thiadiazol-2-yl]-amino}-methyl)-phenyl]-difluoro-methyl}-phosphonic acid;

({2-Bromo-4-[((3,4-dichloro-phenyl)-{5-[3-(3-methanesulfonyl-phenoxy)-phenyl]-[1,3,4]thiadiazol-2-yl}-amino)-methyl]-phenyl}-difluoro-methyl)-phosphonic acid;

3-(3-{5-[[3,5-Dibromo-4-(difluoro-phosphono-methyl)-benzyl]-(3,4-dichloro-phenyl)-amino]-[1,3,4]thiadiazol-2-yl}-phenoxy)-benzoic acid;

5-{[{5-[3-(3-Carboxy-phenoxy)-phenyl]-[1,3,4]thiadiazol-2-yl}-(3,4-dichloro-phenyl)-amino]-methyl}-2-(oxalyl-amino)-benzoic acid;

3-(3-{5-[(3-Bromo-4-{[(2,2-dimethyl-propionyloxymethoxy)-hydroxy-phosphoryl]-difluoro-methyl}-benzyl)-(3,4-dichloro-phenyl)-amino]-[1,3,4]thiadiazol-2-yl}-phenoxy)-benzoic acid 2,2-dimethyl-propionyloxymethyl ester;

{[4-({[4-(Difluoro-phosphono-methyl)-benzyl]-[5-(3-phenoxy-phenyl)-[1,3,4]thiadiazol-2-yl]-amino}-methyl)-phenyl]-difluoro-methyl}-phosphonic acid;

3-(3-{5-[[3-Bromo-4-(2-carboxy-vinyl)-benzyl]-(3,4-dichloro-phenyl)-amino]-[1,3,4]thiadiazol-2-yl}-phenoxy)-benzoic acid;

4-({Benzoyl-[5-(3-phenoxy-phenyl)-[1,3,4]thiadiazol-2-yl]-amino}-methyl)-benzoic acid; or 5-(4-{[{5-[3-(3-Carboxy-phenoxy)-phenyl]-[1,3,4]thiadiazol-2-yl}-(3,4-dichloro-phenyl)-amino]-methyl}-phenyl)-isoxazole-3-carboxylic acid.

In another embodiment, the compounds for use in the compositions and methods provided herein have formula IV:

where G is H or

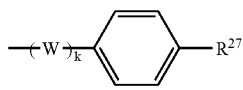

W is CO or SO$_2$, in another embodiment, W is CO;
k is 0 or 1;
R$^{25}$ is H or Br;
R$^{26}$ is CF$_2$PO$_3$H$_2$ or SO$_2$NH$_2$;
R$^{27}$ is H or SO$_2$-1-piperidinyl;
R$^{28}$ is H or Me; and
R$^{29}$ is COOH, COOMe, COOCH$_2$OC(O)-t-Bu or OCH$_2$COOH.

In another embodiment, the compounds of formula IV are:

4-{2-Benzoylimino-3-[3-bromo-4-(difluoro-phosphono-methyl)-benzyl]-2,3-dihydro-thiazol-4-yl}-benzoic acid methyl ester;

4-{3-[3-Bromo-4-(difluoro-phosphono-methyl)-benzyl]-2-imino-2,3-dihydro-thiazol-4-yl}-benzoic acid;

4-{2-Benzoylimino-3-[3-bromo-4-(difluoro-phosphono-methyl)-benzyl]-2,3-dihydro-thiazol-4-yl}-benzoic acid;

4-{3-[3-Bromo-4-(difluoro-phosphono-methyl)-benzyl]-2-imino-2,3-dihydro-thiazol-4-yl}-benzoic acid 2,2-dimethyl-propionyloxymethyl ester; or 4-[3-(3-Bromo-4-{[(2,2-dimethyl-propionyloxymethoxy)-hydroxy-phosphoryl]-difluoro-methyl}-benzyl)-2-imino-2,3-dihydro-thiazol-4-yl]-benzoic acid.

C. Preparation of the Compounds

The compounds for use in the compositions and methods provided herein may be obtained from commercial sources (e.g., Aldrich Chemical Company, Milwaukee, Wis.), may be prepared by methods well known to those of skill in the art, or by the methods shown herein. One of skill in the art would be able to prepar all of the compounds for use herein by routine modification of these methods using the appropriate starting materials.

Scheme-1

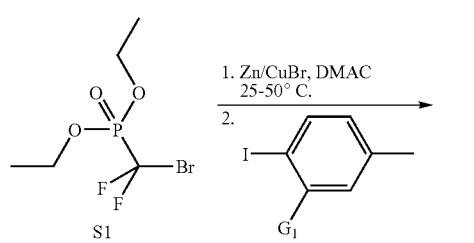

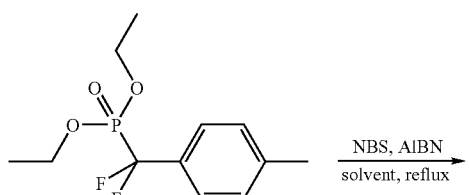

G$_1$ = H, F, Cl, Br
Yields: 40-80%
S2

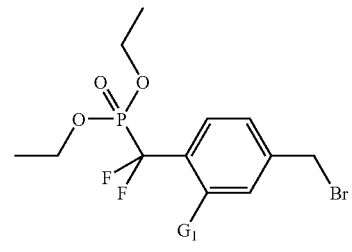

G$_1$ = H, F, Cl, Br
Yields: 50-60%
S3

Scheme-2

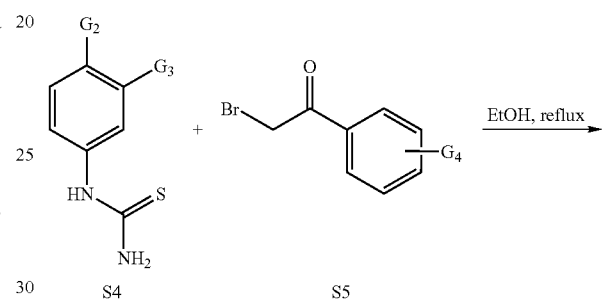

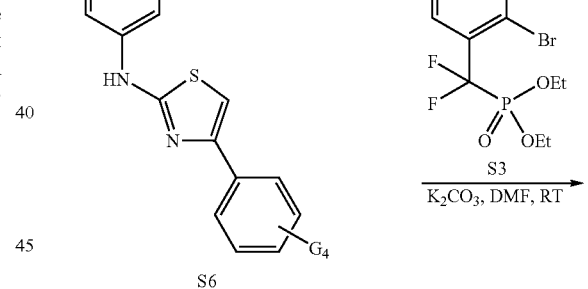

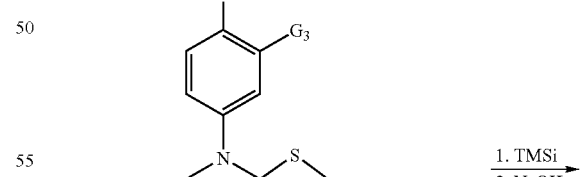

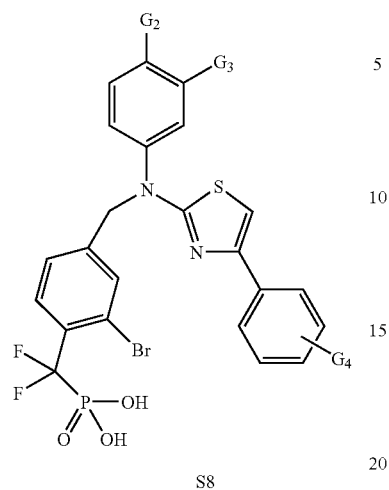
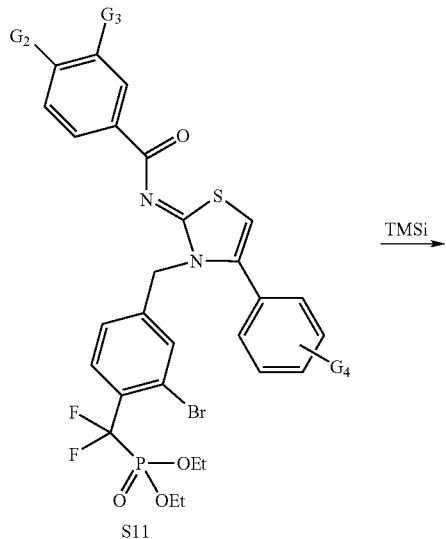
Scheme-3
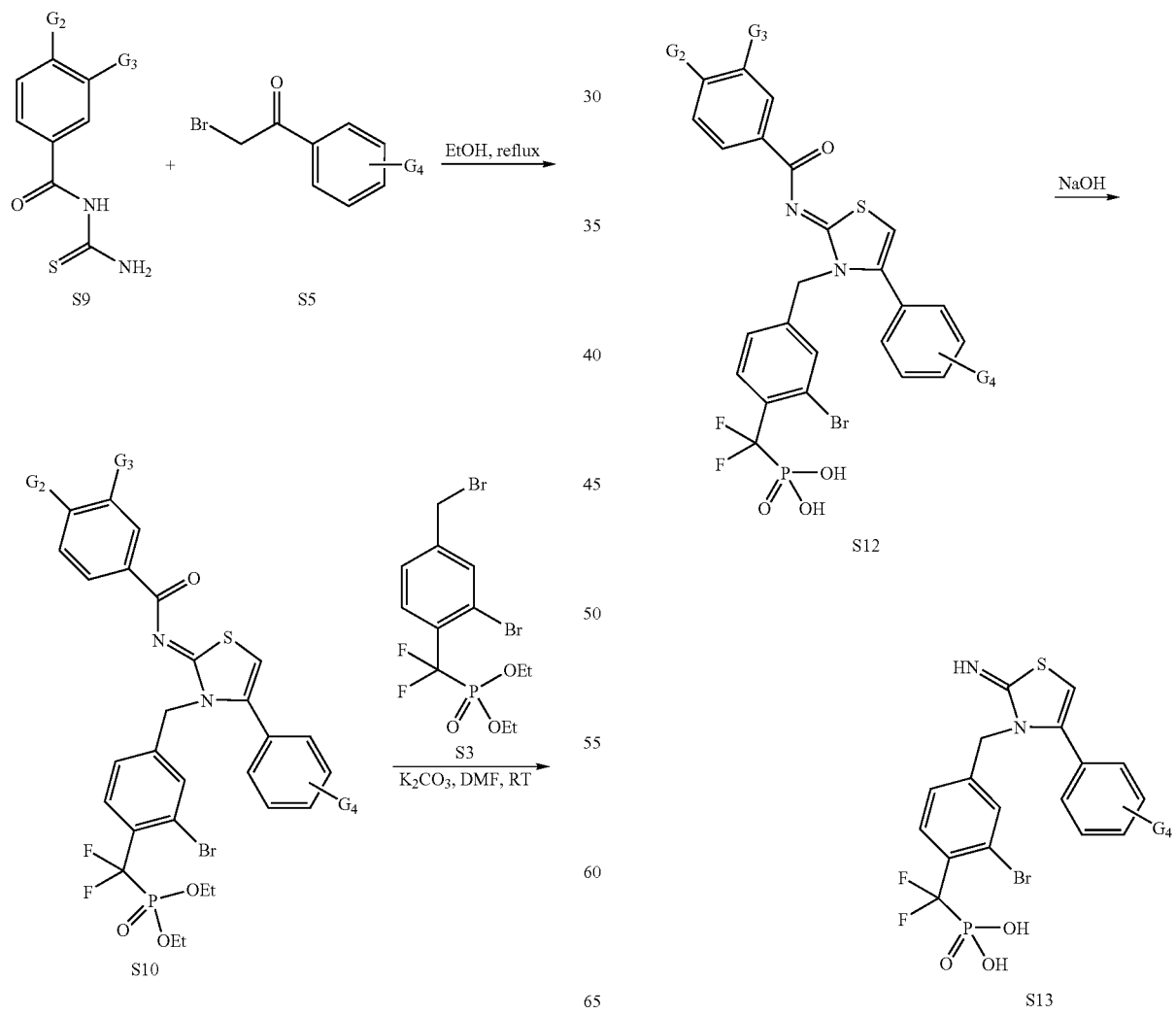

Scheme-4
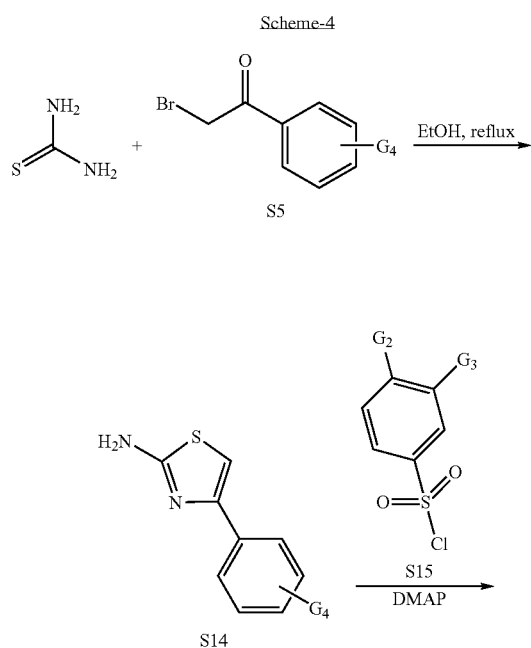
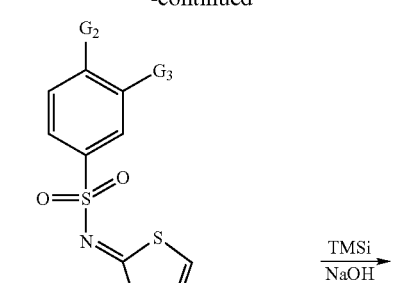
-continued
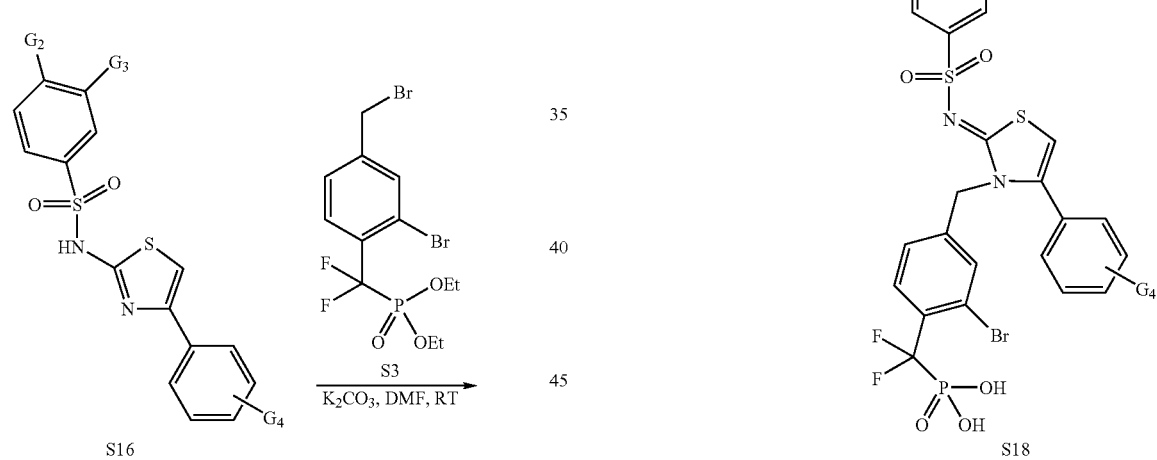
Scheme-5
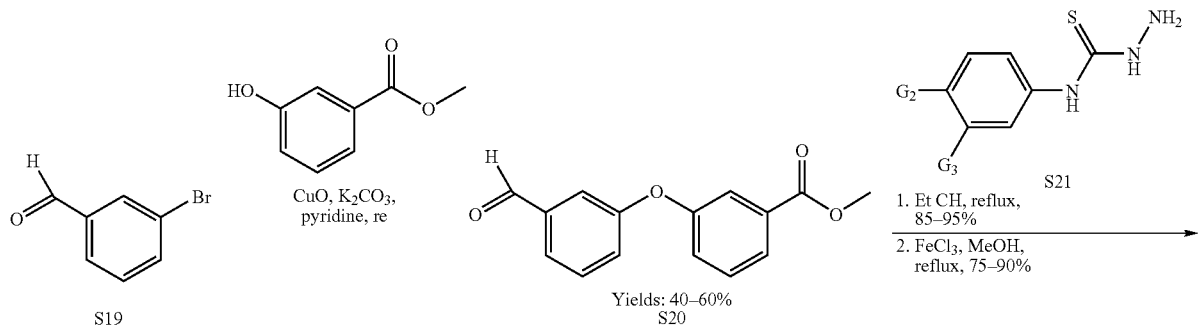

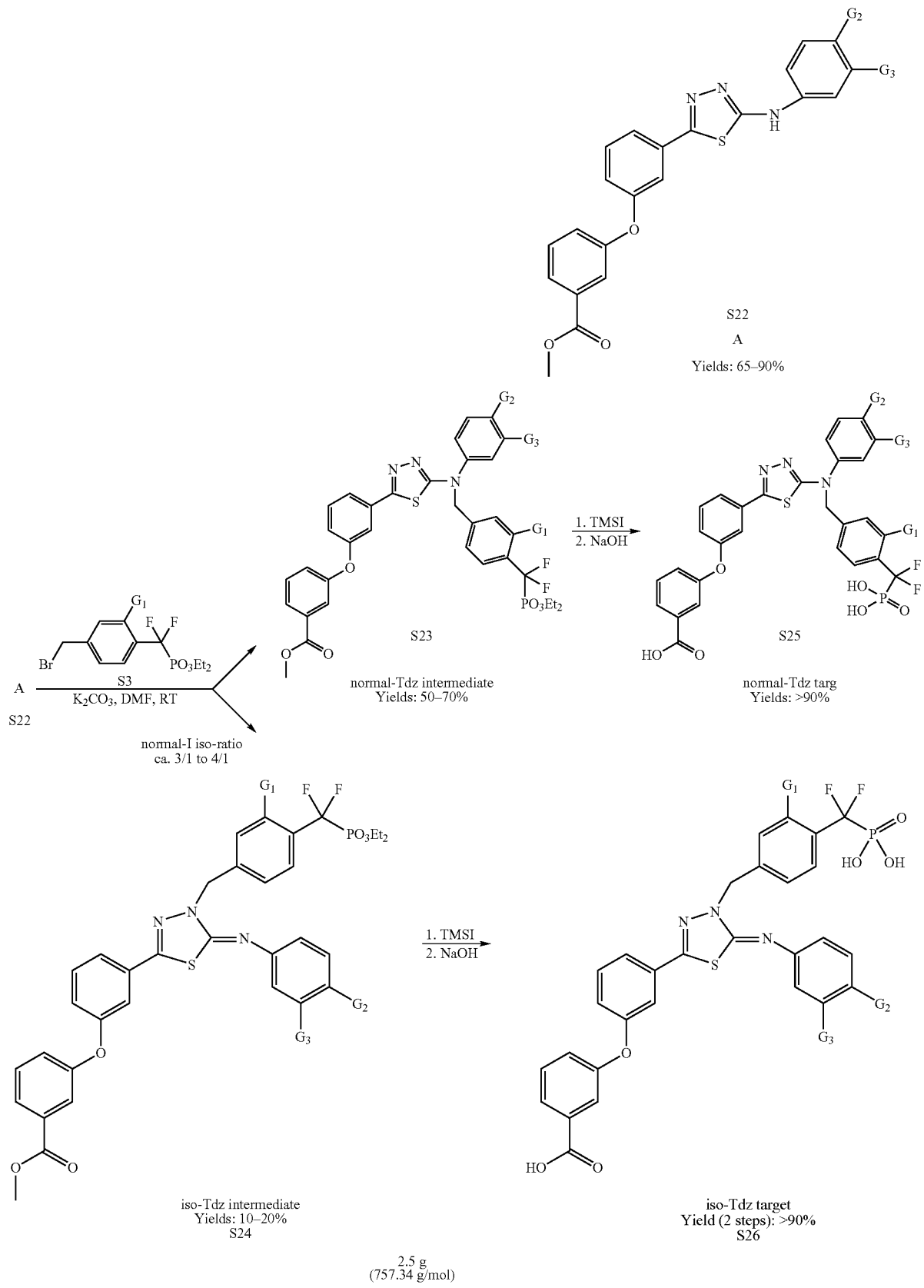

Schemes 1 through Scheme 5 depict generic synthetic routes to compounds of the present invention. All generic schemes feature a key shown below that provides a range of reaction conditions, reagents, solvents, catalysts and conditions that would be useful for preparing depicted intermediates and final target molecules to those skilled in the art of organic synthesis. More details concerning the preparation of these targets are provided in the experimental section. For comprehensive reviews and numerous relevant references to the generic synthetic pathways and reaction conditions presented herein below, the following authoritative works are cited: R. C. Larock, *Comprehensive Organic Transformations*, 2nd ed., Wiley-VCH, New York, N.Y., 1999; *Comprehensive Organic Chemistry*, ed. D. H. R. Barton and W. D. Ollis, Pergamon Press, Oxford, 1979; *Comprehensive Organic Synthesis*, ed. B. M. Trost and I. Fleming, Pergamon Press, Oxford, 1991. For relevant comprehensive reviews and references on protection/deprotection strategies used herein, see: *Protective Groups in Organic Synthesis*, 3rd ed., ed. T. W. Greene and P. G. M. Wuts, John Wiley and Sons, New York, N.Y., 1999; cf Ch. 5 (carboxyl), Ch. 3 (phenols), Ch. 7 (amino groups), Ch. 9 (phosphate).

Scheme 1 describes a generic protocol to the intermediate difluoromethylphosphonate ester, which is obtained from the requisite iodotoluene via displacement of the iodo-group with a suitable dialkyl α,α-dibromo-α-fluoromethyl phosphonate in the presence of metallic reagents such as Zn and CuBr in a dipolar aprotic solvent such as DMF or DMAC at around −20° C. to about 70° C. Bromination of S2 proceeds under free radical-generating conditions utilizing N-bromosuccinimide, 1,3-dibromo-5,5-dimethylhydantoin and similar reagents and provides the bromoalkyl intermediate S3. The bromination reaction is conducted in suitable inert solvents including $CCl_4$, $CHCl_3$, DCE, and benzene and is catalyzed by the addition of radical initiators including benzoyl peroxide, 2,2'-azobisisobutyronitrile (AIBN) and related AIBN derivatives, optionally in the presence of a incandescent or ultraviolet light source. Temperature range for the bromination reaction is around 20° C. to 85° C.

Scheme 2 depicts a generic protocol to the synthesis of N,N-disubstituted 2-amino thiazoles. Thiourea S4 is treated with a α-halo ketone S5 to afford thiazole S6. This reaction can be done in a solvent chosen from ethanol, methanol, DCM, DCE, DMF, THF, diethyl ether, dioxane, toluene, xylene, acetonitrile or mixtures thereof, optionally in the presence of a base such as a tertiary amine like $Et_3N$, DIPEA, NMM, NMP, DBU, DBN, DABCO, tertiary amine base derivatives attached to resin supports, aromatic bases including pyridine, collidine, or lutidine. These reactions may be performed in the temperature range of about room temperature to 150° C. The α-halo ketone S5 can be prepared from the appropriate acetophenone by several methods. (Kimpe, N. D.; Verhe, R. The Chemistry of α-halo ketones, α-halo aldehydes and α-haloimines. In *The Chemistry of Functional Groups*; Patai, S.; Rappoport, Z. Eds.; John Wiley & Sons: Chichester, 1988; pp. 1-119. The intermediate S6 is treated with a base such as sodium hydride, potassium hydride, lithium bis(trimethylsilyl) amide, sodium bis(trimethylsilyl)amide, potassium bis(trimethylsilyl)amide, potassium tert-butoxide, sodium ethoxide, sodium methoxide, sodium hydroxide, potassium hydroxide, sodium carbonate or potassium carbonate in suitably compatible solvents such as DCM, DCE, DMF, THF, diethyl ether, dioxane, toluene, xylene, acetonitrile or mixtures thereof and is then alkylated with the bromo intermediate S3 or similar alkylating agent to provide S7. Temperature range for the alkylation reaction is about −20° C. to 100° C. Cleavage of the dialkylphosphonate ester moiety is achieved by limited exposure of S7 to ($Me_3SiI$/ TFA, $H_2O$). If G4 in S7 has a protected carboxylate group, conditions for the hydrolysis of the carboxylate ester moiety depend upon the nature of the protecting group. In cases where methyl, ethyl and related primary esters are used as carboxylate protecting groups, hydrolysis of ester intermediate S7 to the final inhibitors S8 is preferably accomplished by treatment of S7 with a base such as lithium hydroxide, lithium hydroperoxide (generated from LiOH and hydrogen peroxide in situ), sodium hydroxide, potassium hydroxide or tetrabutylammonium hydroxide in a solvent such as methanol, ethanol, isopropanol, tert-butanol, THF, dioxane, acetonitrile, water and mixtures thereof. The hydrolysis reaction can be performed in the temperature range of about −10° C. to 100° C. Ester hydrolysis can also be affected by use of appropriate enzymes including any of the commercially available lipases and esterases, typically in an aqueous solvent system at around 0° C. to 50° C. Alternate hydrolysis methods include treatment of S7 with trimethylsilyl iodide in solvents including DCM, $CHCl_3$, $CCl_4$ or DCE at about 0° C. to 100° C., followed by proteolysis of the resultant trimethyl silyl ester intermediate; treatment of S7 with sodium chloride, calcium chloride and related alkaline earth halides in DMSO at about 80° C. to 150° C.; reaction of S7 with a alkali metal thioalkoxide (e.g. sodium thiomethoxide, lithium thioethoxide, lithium thiopropoxide) in a suitable solvent such as DMF, DMAC or DMSO at about 25° C. to 150° C.; cleavage with lithium iodide in pyridine, lutidine or collidine at about 80° C. to 170° C. and cleavage with potassium-, sodium- or lithium trimethylsilanoate in DCM, THF or toluene at about 20° C. to 120° C., followed by acidification of the resultant salt.

In cases where the ester R group=t-butyl, intermediate S7 is treated with a hydrogen chloride or hydrogen bromide source, usually in anhydrous media at around −20° to about 30° C. In cases where the ester R group=(substituted)-benzyl or (substituted)-heteroarylmethyl, intermediate S7 is hydrogenated at ambient room temperature at around 15-70 PSI hydrogen pressure in a suitable inert solvent like ethanol, methanol, THF, ethyl acetate, acetic acid, or mixtures thereof in the presence of a catalyst such as palladium on carbon, palladium hydroxide, and related palladium derivatives. Alternate ester hydrogenolysis conditions include palladium on carbon catalysts with hydrogen transfer reagents selected from formic acid and formate salts, cyclohexene, sodium- or potassium hypophosphite. Suitable solvents include those listed above. Suitable temperature range is about 0° C. to 100° C.

In cases where the ester R group=(substituted)allyl or (substituted)phenylpropenyl(cinnamyl), intermediate S7 is treated with a catalytic amount of an organopalladium reagent such as $(Ph_3P)_4Pd$ in the presence of appropriate allylic group acceptors such as diethyl amine, piperidine, morpholine and dimedone. Suitable solvents include DCM, DCE, THF, DMSO, acetonitrile, water, and mixtures thereof. Addition of catalytic amounts of hydrochloric acid or water may facilitate this deprotection process.

Scheme 3 depicts a generic protocol to the synthesis of N-Benzoyl-2-amino thiazoles and 2-imino thiazoles. Substituted Benzoyl thiourea S9 is treated with a α-halo ketone S5 to afford thiazole S10. The conditions for formation of the thiazole S10 are the same as detailed in scheme 2. The intermediate S10 is treated with a base such as sodium hydride, potassium hydride, lithium bis(trimethylsilyl) amide, sodium bis(trimethylsilyl)amide, potassium bis(trimethylsilyl)amide, potassium tert-butoxide, sodium ethoxide, sodium methoxide, sodium hydroxide, potassium hydroxide, sodium carbonate or potassium carbonate in suitably compatible solvents such as DCM, DCE, DMF, THF, diethyl ether, dioxane, toluene, xylene, acetonitrile, or mixtures thereof and is then alkylated with the bromo intermediate S3 or similar alkylating agent to provide S11. Cleavage of the dialkylphosphonate ester moiety is achieved by limited exposure of S11 to ($Me_3SiI/TFA$, $H_2O$) to obtain the N-Benzoyl thiazole S12.). If G4 in S12 has a protected carboxylate group, conditions for the hydrolysis of the carboxylate ester moiety depend upon the nature of the protecting group. In cases where methyl, ethyl and related primary esters are used as carboxylate protecting groups, hydrolysis of ester intermediate S12 to the final inhibitors S13 is preferably accomplished by treatment of S12 with a base such as lithium hydroxide, lithium hydroperoxide (generated from LiOH and hydrogen peroxide in situ), sodium hydroxide, potassium hydroxide or tetrabutylammonium hydroxide in a solvent such as methanol, ethanol, isopropanol, tert-butanol, THF, dioxane, acetonitrile, water and mixtures thereof. The hydrolysis reaction can be performed in the temperature range of about $-10°$ C. to $100°$ C. Also the N-benzoyl group in S12 is deprotected under the conditions mentioned above for the deprotection of the methyl, ethyl and related esters. However if the carboxylate-protecting group is not methyl, ethyl or related ester, then it is deprotected as shown in details of scheme-2.

Scheme 4 depicts a generic protocol to the synthesis of N-Sulfonyl-2-amino thiazoles. Thiourea is treated with a α-halo ketone S5 to afford the 2-amino thiazole S13. The conditions for formation of the thiazole S15 are the same as detailed in scheme 2. Treatment of S13 with an appropriately substituted sulfonyl chlorides S14 optionally in the presence of a base such as a tertiary amine like $Et_3N$, DIPEA, NMM, NMP, DBU, DBN, DABCO, tertiary amine base derivatives attached to resin supports, aromatic bases including pyridine, collidine, lutidine, or inorganic bases including sodium carbonate, potassium carbonate, sodium hydrogen carbonate and potassium hydrogen carbonate to afford sulfonamide S15. The sulfonylation reaction is performed in a solvent chosen from DCM, DCE, DMF, DMAC, THF, diethyl ether, dioxane, toluene, xylene, acetonitrile or mixtures thereof. Temperature range for the coupling reaction is about $-20°$ C. to $100°$ C. Alkylation of S15 to S16 is done under the same conditions as shown above in the details of scheme-3. Cleavage of the dialkylphosphonate ester moiety is achieved by limited exposure of S16 to ($Me_3SiI/TFA$, $H_2O$). If G4 in S16 has a protected carboxylate group, the hydrolysis of the carboxylate ester moiety depend upon the nature of the protecting group and is done as shown above in scheme 2.

Scheme 5 depicts a generic protocol to the synthesis of N,N-disubstituted-2-amino thiadiazoles. Ullman reaction of S19 with 3-hydroxy methyl benzoate gives S20. Treatment of S20 with the appropriately substituted S21 in the presence of FeCl3 gave S22. Alkylation of S22 with S4 is done under the same conditions as shown in details of scheme 2. Alkylation of S22 gives an approximate 1:3 mixture to 1:4 mixture of S23 and S24. Deprotection of the phosphate group and the carboxylate group is done under the same conditions as described in scheme 2 above to obtain S25 and S26.

D. Formulation of Pharmaceutical Compositions

The pharmaceutical compositions provided herein contain therapeutically effective amounts of one or more of the compounds provided herein that are useful in the prevention, treatment, or amelioration of one or more of the symptoms of diseases or disorders associated with protein tyrosine phosphatase, including PTP-1B, activity, or in which protein tyrosine phosphatase, including PTP-1B, activity is implicated, and a pharmaceutically acceptable carrier. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with protein tyrosine phosphatase, including PTP-1B, activity or in which protein tyrosine phosphatase, including PTP-1B, activity is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems well known to those of skill in the art and described herein (see, e.g., EXAMPLES 56 and 57) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with protein tyrosine phosphatase, including PTP-1B, activity or in which protein tyrosine phosphatase, including PTP-1B, activity is implicated, as described herein.

In one embodiment, a therapeutically effective dosage should produce a serum concentration of active ingredient of from about 0.1 ng/ml to about 50-100 µg/ml. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

2. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEENâ 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture containing packaging material, a compound or pharmaceutically acceptable derivative thereof provided herein, which is effective for modulating protein tyrosine phosphatase, including PTP-1B, activity, or for treatment, prevention or amelioration of one or more symptoms of diseases or disorders in which protein tyrosine phosphatase, including PTP-1B, activity, is implicated, within the packaging material, and a label that indicates that the compound or composition, or pharmaceutically acceptable derivative thereof, is used for modulating protein tyrosine phosphatase, including PTP-1B, activity, or for treatment, prevention or amelioration of one or more symptoms of diseases or disorders in which protein tyrosine phosphatase, including PTP-1B, activity is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which protein tyrosine phosphatase, including PTP-1B, activity is implicated as a mediator or contributor to the symptoms or cause.

8. Prodrugs

One form of prodrug is to prepare acetoxymethyl esters of the compounds provided herein, which may be prepared by the general procedure reported by C. Schultz et al., J. Biol. Chem. 1993, 268:6316-6322:

A carboxylic acid (1 eq) is suspended in dry acetonitrile (2 mL/0.1 mmol). Diisopropyl amine (3.0 eq) is added followed by bromomethyl acetate (1.5 eq). The mixture is stirred under nitrogen overnight at room temperature. Acetonitrile is removed under reduced pressure to yield an oil, which is diluted in ethylacetate and washed with water (3×). The organic layer is dried over anhydrous magnesium sulfate. Filtration, followed by solvent removal under reduced pressure, affords a crude oil. The product is purified by column chromatography on silica gel, using an appropriate solvent system.

Other prodrugs can routinely be prepared from compounds provided herein by the procedures outlined in the following, the disclosures of which are incorporated herein by reference in their entirety:

Stankovic C J et al., "The Role of 4-Phosphonodifluoromethyl- and 4-Phosphono-phenylalanine in the Selectivity and Cellular Uptake of SH2 Domain Ligands." *Bioorg. Med. Chem. Lett.* 1997; 7(14):1909-14.

Ortmann R et al., "Acyloxyalkyl ester prodrugs of FR900098 with improved in vivo anti-malarial activity." *Bioorg. Med. Chem. Lett.* 2003; 13(13):2163-6.

Hughes W T et al., "Single-dose pharmacokinetics and safety of the oral antiviral compound adefovir dipivoxil in children infected with human immunodeficiency virus type 1." *Antimicrob Agents Chemother.* 2000; 44(4):1041-6.

Starrett J E Jr et al., "Synthesis and in vitro evaluation of a phosphonate prodrug: bis(pivaloyloxymethyl)9-(2-phosphonylmethoxyethyl)adenine." *Antiviral Res.* 1992; 19(3):267-73.

Such prodrug preparations are routinely prepared, once a novel drug compound is identified, such as the novel PTP-1B inhibitors disclosed herein.

Other prodrugs of the compounds provided herein are prodrugs of difluoromethylphosphonic acids and have the formulae $ArCF_2P(O)(OH)(OCH(H/Me)OC(=O)OiPr$, $ArCF_2P(O)[(OCH(H/Me)OC(=O)OiPr]_2$, $ArCF_2P(O)(OH)(OCH(H/Me)OC(=O)tBu$, or $ArCF2P(O)[(OCH(H/Me)OC(=O)tBu]_2$. Other prodrugs of the compounds provided herein have the formulae $ROCH_2CHR'CH_2O—P(O)(OH)CF_2Ar$ or $(ROCH_2CHR'CH_2O)_2—P(O)CF_2Ar$, where R is $C_{14-20}$-n-alkyl and R' is H, OH or OMe. Further prodrugs of the compounds provided herein are prodrugs as described in EP 0 350 287; EP 0 674 646; U.S. Pat. No. 6,599,887; U.S. Pat. No. 6,448,392; U.S. Pat. No. 6,752,981; U.S. Pat. No. 6,312,662; U.S. 2002/0173490; Friis et al. *Eur. J. Pharm. Sci.* 4:49-59 (1996); Erion et al. *J. Am. Chem. Soc.* 126: 5154-5163 (2004); WO 03/095665; Krise et al. *Adv. Drug. Deliv. Rev.* 19:287-310 (1996); and Ettmayer et al. *J. Med. Chem.* 47:2393-2404 (2004). The disclosures of these patents and publications are incorporated by reference herein in their entirety.

Examples of these prodrugs are shown in the table below.

| Structure | Example | Chemical Name |
|---|---|---|
| 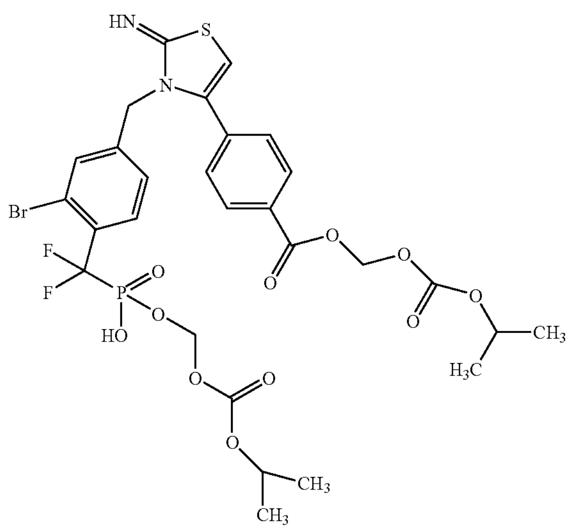 | 51 | 4-(3-{3-Bromo-4-[difluoro-(hydroxy-isopropoxycarbonyl oxymethoxy-phosphoryl)-methyl]-benzyl}-2-imino-2,3-dihydro-thiazol-4-yl)-benzoic acid isopropoxycarbonyloxymethyl ester |
| 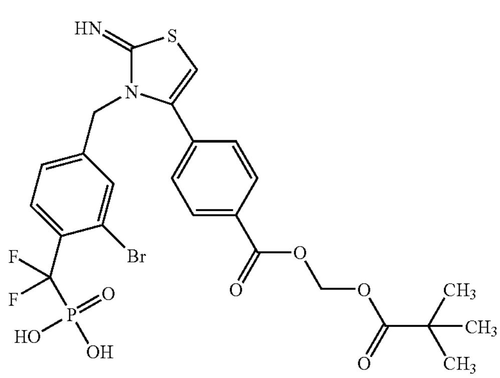 | 54 | 4-{3-[3-Bromo-4-(difluoro-phosphono-methyl)-benzyl]-2-imino-2,3-dihydro-thiazol-4-yl}-benzoic acid 2,2-dimethyl-propionyloxymethyl ester |

-continued

| Structure | Example | Chemical Name |
|---|---|---|
| 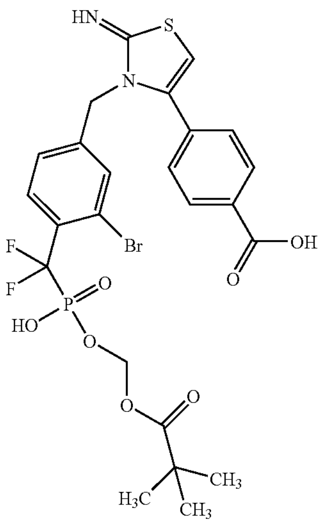 | 55 | 4-[3-(3-Bromo-4-{[(2,2-dimethyl-propionyloxymethoxy)-hydroxy-phosphoryl]-difluoro-methyl}-benzyl)-2-imino-2,3-dihydro-thiazol-4-yl]-benzoic acid |
| | | 4-[2-(3-Bromo-4-{difluoro-[hydroxy-(1-isopropoxycarbonyl-oxy-ethoxy)-phosphoryl]-methyl}-benzylamino)-thiazol-4-yl]-benzoic acid 1-isopropoxy-carbonyloxy-ethyl ester |
| | | 4-[2-(3-Bromo-4-{[(2,2-dimethyl-propionyloxymethoxy)-hydroxy-phosphoryl]-difluoro-methyl}-benzylamino)-thiazol-4-yl]-benzoic acid 2,2-dimethyl-propionyloxymethyl ester |

In certain embodiments, the prodrugs provided herein exhibit improved activity in cell-based assays (e.g., EXAMPLE 57) as compared to the parent compounds. For example, 4-[2-(3-Bromo-4-{[(2,2-dimethyl-propionyloxymethoxy)-hydroxy-phosphoryl]-difluoro-methyl}-benzylamino)-thiazol-4-yl]-benzoic acid 2,2-dimethyl-propionyloxymethyl ester exhibits approximately a 10-fold increase in activity in a cell-based assay as compared to the parent carboxylic-phosphonic acid.

E. Evaluation of the Activity of the Compounds

The activity of the compounds as modulators of protein tyrosine phosphatase, including PTP-1B, may be measured in standard assays (see, e.g., Examples 56 and 57). Briefly, an assay described herein employes human recombinant PTP-1B and a pNPP substrate in a rescue assay.

F. Methods of Use of the Compounds and Compositions

Methods of modulating the activity of a protein tyrosine phosphatase, including PTP-1B, by contacting the protein tyrosine phosphatase with a compound or composition provided herein are provided. In one embodiment, the PTP, including PTP-1B, is inhibited by the compound or composition.

Methods of increasing insulin sensitivity by administering a compound or composition provided herein are provided.

Methods of treating, preventing, or ameliorating one or more symptoms of a protein tyrosine phosphatase mediated disease, including PTP-1B mediated diseases, by administering a compound or composition provided herein are provided. Such diseases include, but are not limited to, diabetes including Type 1 and Type 2 diabetes (and associated complications such as hypertension, ischemic diseases of the large and small blood vessels, blindness, circulatory problems, kidney failure and atherosclerosis), syndrome X, metabolic syndrome, glucose intolerance, insulin resistance, leptin resistance, obesity, cancer, neurodegenerative diseases, and other diseases in which the activity of a tyrosine phosphatase or multiple tyrosine phosphatases contributes to the symptoms or pathology thereof.

G. Combination Therapy

The compounds and compositions provided herein may also be used in combination with other active ingredients. In another embodiment, the compounds may be administered in combination, or sequentially, with another therapeutic agent. Such other therapeutic agents include those known for treatment, prevention, or amelioration of one or more symptoms of protein tyrosine phosphatase, including PTP-1B, mediated diseases. Such therapeutic agents include, but are not limited to, antiobesity agents, antidiabetics, antihypertensive agents, agents for the treatment and/or prevention of complications resulting from or associated with diabetes and agents for the treatment and/or prevention of complications and disorders resulting from or associated with obesity.

In another embodiment, the compounds provided herein may be administered in combination with one or more antiobesity agents or appetite regulating agents. Such agents include, but are not limited to, CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, B3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator activated receptor) modulators, RXR (retinoid X receptor) modulators or TR B agonists.

In one embodiment the antiobesity agent is leptin. In other embodiments, the antiobesity agent is dexamphetamine or amphetamine, fenfluramine or dexfenfluramine, sibutramine, orlistat, mazindol or phentermine.

In another embodiment, the antidiabetic is insulin, GLP-1 (glucagons like peptide-1) derivatives such as those disclosed in WO 98/08871, which is incorporated herein by reference, as well as orally active hypoglycemic agents. The orally active hypoglycemic agents include, but are not limited to, sulfonylureas, biguanides, meglitinides, oxadiazolidinediones, thizolidinediones, glucosidase inhibitors, glucagons antagonists such as those disclosed in WO 99/01423, GLP-1 agonists, potassium channel openers such as those disclosed in WO 98/26265 and WO 99/03861, insulin sensitizers, DPP-IV (dipeptidyl peptidase-IV) inhibitors, inhibitors of hepatic enzymes involved in stimulation of gluconeogensis and/or glycogenolysis, glucose uptake modulators, compounds modifying the lipid metabolism such as antihyperlipidemic agents and antilipedimic agents as HMG CoA inhibitors (statins), compounds lowering food intake, PPAR and RXR agonists and agents acting on the ATP-dependent potassium channel of the B-cells.

In one embodiment the present compounds are administered in combination with insulin. In further embodiments, the present compounds are administered in combination with a sulphonylurea e.g., tolbutamide, glibenclamide, glipizide or glicazide, a biguanide e.g. metformin, a meglitinide e.g., repaglinide, a thiazolidinedione e.g., troglitazone, ciglitazone, pioglitazone, rosiglitazone or compounds disclosed in WO 97/41097 such as 5-[[4-[3-Methyl-4-oxo-3,4-dihydro-2-quinazolinyl]methoxy]phenyl-methyl]thiazolidine-2, 4-dione or a pharmaceutically acceptable salt thereof.

In another embodiment, the present compounds may be administered in combination with the insulin sensitizers disclosed in WO 99/19313 such as (−)3-[4-[2-phenoxazin-10-yl]ethoxy]phenyl]-2-ethoxypropanoic acid or a pharmaceutically acceptable salts thereof, preferably the arginine salt.

In further embodiments, the present compounds are administered in combination with an α-glucosidase inhibitor e.g. miglitol or acarbose, an agent acting on the ATP-dependent potassium channel of the B-cells e.g. tolbutamide, glibenclamide, glipizide, glicazide or repaglinide, nateglinide, an antihyperlipidemic agent or antilipidemic agent e.g., cholestyramine, colestipol, clofibrate, gemfibrozil, lovastatin, pravastatin, simvastatin, probucol or dextrothyroxine, In still further embodiments, the present compounds are administered in combination with more than one of the above-mentioned compounds e.g., in combination with a sulphonylurea and metformin, a sulphonylurea and acarbose, repaglinide and metformin, insulin and a sulphonylurea, insulin and metformin, insulin and lovastatin, CART agonist and a CCK agonist, etc.

In another embodiment, the present compounds may be administered in combination with one or more antihypertensive agents. Examples of antihypertensive agents are B-blockers such as alprenolol, atenolol, timolot, pindolol, propranolol and metoprolol, ACE (angiotensin converting enzyme) inhibitors such as benazepril, captopril, analapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

It should be understood that any suitable combination of the compounds provided herein with one or more of the above-mentioned compounds and optionally one or more further pharmacologically active substances are considered to be within the scope of the present disclosure. In another embodiment, the compound provided herein is administered prior to or subsequent to the one or more additional active ingredients.

The following examples are provided for illustrative purposes only and are not intended to limit the scope of the invention.

General Procedures

Procedure A (3-[(2-Phenylphenyl)methylthio]phenylamine): 2-phenyl benzylbromide (2.47 g; 10 mmol) is added slowly to a stirred solution of 3-aminothiophenol (1.25 g; 10 mmol) in the mixture of ethanol (20 mL) and 1M NaOH (10 mL). The mixture is stirred for 30 minutes, the solvent evaporated and the residue is purified using a Biotage column. The product is eluted with EtoAc/Hexanes (4/1). Yield: 1.8 g (62%).

$^1$H NMR: (300 MHz, CDCl$_3$) 7.39 δ(7H, m); 7.31 δ(3H, m); 7.00 δ(1H, t); 6.49 δ(1H, s); 6.48δ(1H, d); 4.07δ (2H, s).

Procedure B

A mixture of 3-bromobenzaldehyde (1.000 g; 5.4 mmol), methyl 3-hydroxybenzoate (987 mg; 6.5 mmol) and potassium carbonate (1.494 g; 10.8 mmol) in dry pyridine (8 mL) is stirred under argon at RT. Copper (II) oxide (860 mg; 10.8 mmol) is added and the reaction mixture is refluxed for 12 hours. After cooling to RT, CH$_2$Cl$_2$ (50 mL) is added and the mixture is filtered through celite. The filter cake is washed with fresh CH$_2$Cl$_2$ (50 mL). The combined organics are concentrated in vacuo. The residue is purified by flash chromatography (ethyl acetate/hexanes, 1:10 to 1:4) to yield methyl 3-(3-carbonylphenoxy)benzoate (776 mg; 56%) as a yellow oil.

$^1$H NMR (300 MHz, CDCl$_3$): δ 9.97 (1H, s), 7.85 (1H, d, J=6.9 Hz), 7.69-7.24 (7H, m), 3.91 (3H, s).

Procedure C

3-[(2-phenylphenyl)methylthio]benzeneisothiocyanate: Thiophosgene (1.37 g; 12 mmol) is slowly added to a solution of 3-[(2-Phenylphenyl) methylthio]phenyl amine in a mixture of water (60 mL) and Methylenechloride (45 mL). The mixture is stirred under nitrogen at RT for two hours. The aqueous layer is separated, and the methylenechloride is washed with water. The organic layers are dried over anhydrous sodium sulfate and rotovaped to provide a brown oil which is used for the next step without further purification. Yield: 2.2 g (70%).

Procedure D

The hydrazine hydrate (7.12 mL; 147 mmol) is dissolved in 220 mL of ethanol. This solution is stirred at 0° C. and 3,4-dichlorobenzenisothiocyanate (20.00 g; 98 mmol) is added dropwise, and the reaction mixture is warmed to RT and stirred for two hours. After being cooled to 0° C., the mixture is filtered and the solid washed by cold ethanol (40 mL). The solid is crystallized from ethanol to yield ([(3,4-dichlorophenyl)-amino]hydrazinomethane-1-thione) (12.702 g; 55%) as a white solid.

$^1$H NMR (300 MHz, d$_6$-DMSO): δ 9.40 (1H, s), 8.19 (1H, s), 7.69 (1H, d), 7.53 (1H, d), 5.30 (3H, br s).

Procedure E (3-(1,3-Dioxolan-2-yl)phenyl)[3-(trifluoromethyl) phenyl]methan-1-ol)

A 1.0 mL aliquot of 2-(3-bromophenyl)-1,3-dioxolane is added into magnesium (610 mg; 25 mmol) and THF (5 mL) under Argon. After the reaction is started, the residue of 2-(3-bromophenyl)-1,3-dioxolane (total: 5.73 g; 25 mmol) in THF (20 mL) is added dropwise into the reaction mixture. The resulting solution is stirred at room temp for six hours, and then at 50-60° C. for 20 hours. After the mixture is cooled, a solution of 3-(trifluoromethyl)-benzaldehyde (4.35 g; 25 mmol) in THF (20 mL) is added dropwise and the reaction is stirred at room temp for 24 hours. A saturated solution of NH$_4$Cl (50 mL) is added and stirred for 30 minutes. The organic layer is separated and the aqueous layer is extracted with ethyl acetate (2×100 mL). The organic layers are combined and dried over anhydrous Na$_2$SO$_4$. The solvent is removed and the residue is purified by column chromatography on silica gel. Eluting with ethyl acetate/hexanes (20:80) provide a colorless oil (3.23 g; 40%) as (3-(1,3-dioxolan-2-yl)phenyl)[3-(trifluoromethyl)phenyl]-methan-1-ol: MS 307.0 (M−17).

Procedure F (Methyl-4-[(hydrazinylthioxomethyl)amino]benzoate: A mixture of methyl 4-isothiocyanato benzoate (193 mg; 1 mmol) and hydrazine (100 mg; 2 mmol) are stirred in toluene (7.5 mL) at RT for two hours. The solid is filtered, washed with a small volume of ethanol and hexanes and dried in vacuum. Yield: 192 mg (85%).

$^1$H NMR: (300 MHz, DMSO-d$_6$) 9.66δ (1H, s); 7.86δ (5H, m); 3.83δ (3H, s).

Procedure G

N-(3-bromophenyl)-2-[(3-nitrophenyl)carbonylamino] acetamide 3-nitrohippuric acid (250 mg; 1.116 mmol) is dissolved in methylene chloride (5 mL) containing a catalytic amount of DMAP, 1-ethyl-3-(3-dimethylaminopropyl) carbodiimide hydrochloride (640 mg; 3.34 mmol) and 3-bromoaniline (290 mg; 1.685 mmol). The solution is stirred for 18 hours at 25° C., diluted with enough methylene chloride to dissolve the resulting precipitate, and washed three times with 2N hydrochloric acid (aqueous) and saturated aqueous sodium chloride. The organic layer is dried with sodium sulfate, filtered, and stripped of solvent in vacuo. The resulting yellow solid is washed with 1:1 acetone/methylene chloride, then with 1:1 acetone/methanol to yield the title compound as a gray solid.

Procedure H

Iron powder (5.03 g; 56 mmol), water (5 mL) and hydrochloric acid (0.1 mL; 36 mmol) are added consecutively to a solution of methyl 2-[4-(3-nitrophenoxy)phenyl] acetate (1.3 g; 4.5 mmol) in ethanol (20 mL). After stirring at 95° C. for four hours, the solid is filtered while still hot and the filtrate is stripped of solvent in vacuo to yield methyl 2-[4-(3-aminophenoxy)phenyl]acetate as an oil. Yield: 1.1 g (95%).

$^1$H NMR: (300 MHz, DMSO-d$_6$) 7.24δ (2H, d); 6.96δ (3H, m); 6.31δ (1H, d); 6.13δ (1H, s); 6.10δ (1H, d); 5.23δ(2H, d); 3.65δ (2H, s); 3.62δ (3H, s).

Procedure I (3,4-Dichloro-phenyl)-(4-phenyl-thiazol-2-yl)-amine: To (3,4-Dichloro-phenyl)-thiourea (2 g, 9.04 mmol) in ethanol (35 mL) was added 2-Bromo-1-phenyl-ethanone and the solution was refluxed overnight. The reaction mixture was allowed to cool to room temperature and the resulting solid was filtered and washed with cold ethyl acetate to yield 2.45 g (85%) of an off-white solid. $^1$H NMR (300 MHz, DMSO-d$_6$) δ 8.16 (d, J=1.8 Hz, 1H), 7.87 (d, J=7.5 Hz, 2 H), 7.61-7.29 (m, 6H); LCMS m/z 319 [M−1]

Procedure J

[(2-Bromo-4-{[(3,4-dichloro-phenyl)-(4-phenyl-thiazol-2-yl)-amino]-methyl}-phenyl)-difluoro-methyl]-phosphonic acid diethyl ester: To (3,4-Dichloro-phenyl)-(4-phenyl-thiazol-2-yl)-amine (0.34 g, 1.04 mmol) in DMF (5 mL) was added K$_2$CO$_3$ (0.23 g, 1.71 mmol). After 0.1 hour, [(2-Bromo-4-bromomethyl-phenyl)-difluoro-methyl]-phosphonic acid diethyl ester (0.15 g, 0.34 mmol) was added and the resulting mixture was stirred at room temperature overnight. The reaction was partitioned between ethyl acetate and H$_2$O, after which the organic layer was dried over NaSO$_4$ and concentrated in vacuo. The resulting material was purified via column chromatography (1/1 hexanes/ethyl acetate) to yield 0.176 g (76%) of a clear, colorless oil; $^1$H NMR (300 MHz, CDCl$_3$) δ 7.84-7.22 (m, 11 H), 6.81 (s, 1 H), 5.23 (s, 2 H), 4.23 (m, 4 H), 1.31 (t, J=7.5 Hz, 6 H).

Procedure K

[(2-Bromo-4-{[(3,4-dichloro-phenyl)-(4-phenyl-thiazol-2-yl)-amino]-methyl}-phenyl)-difluoro-methyl]-phosphonic acid: To [(2-bromo-4-{[(3,4-dichloro-phenyl)-(4-phenyl-thiazol-2-yl)-amino]-methyl}-phenyl)-difluoro-methyl]-phosphonic acid diethyl ester (0.176 g, 0.25 mmol) in $CH_2Cl_2$ (3 mL) was added bistrimethylsilyltrifluoroacetamide (0.66 g, 2.59 mmol) and reaction mixture was stirred at room temperature for 1 h after which the reaction mixture is cooled to 20° C. and iodotrimethylsilane (0.51 g, 2.59 mmol) is added drop wise. The resulting mixture was stirred at room temperature for 1.5 hours, after which it was concentrated in vacuo. The resulting material was stirred in $CH_3CN$ (4 mL), $H_2O$ (0.5 mL), and TFA (0.5 mL) for 0.5 hours, after which it was concentrated in vacuo and partitioned between ethyl acetate and acidic $Na_2S_2O_4$. The organic layer was dried over $MgSO_4$ and concentrated in vacuo to yield 0.31 g (99%) of a white foam; $^1H$ NMR (300 MHz, DMSO-$d_6$) δ 7.99-7.28 (m, 12 H), 5.33 (s, 2 H); LCMS m/z 619 [M$^-$]

Procedure L (4-{2-[[3-Bromo-4-(difluoro-phosphono-methyl)-benzyl]-(3,4-dichloro-phenyl)-amino]-thiazol-4-yl}-benzoic acid: To 4-{2-[[3-Bromo-4-(difluoro-phosphono-methyl)-benzyl]-(3,4-dichloro-phenyl)-amino]-thiazol-4-yl}-methyl benzoate (0.99 g, 0.146 mmol) in 3 mL each of THF and methanol was added a 2.5 N solution of NaOH (5 equiv) and the reaction was stirred at room temperature overnight and concentrated in vacuo. The residue was washed with ethyl acetate, and then 15% HCl aqueous solution was added until the pH was 2. The water layer was extracted with ethyl acetate and washed with brine. Concentration in vacuo gave the title compound, (4-{2-[[3-Bromo-4-(difluoro-phosphono-methyl)-benzyl]-(3,4-dichloro-phenyl)-amino]-thiazol-4-yl}-benzoic acid in 90% yield.

Procedure M

[(2-Bromo-4-methyl-phenyl)-difluoro-methyl]-phosphonic acid diethyl ester: A solution of (bromo-difluoro-methyl)-phosphonic acid diethyl ester (25.00 g, 93.6 mmol) in N,N-dimethylacetamide (50 mL) was added drop wise into a suspension of activated zinc (6.12 g, 93.6 mmol) under Argon. The reaction was initiated by heating and kept under 50° C. After the mixture was stirred for 3 h, copper (I) bromide (13.43 g, 93.6 mmol) was added and stirred for 1 h. A solution of 2-bromo-1-iodo-4-methyl-benzene (11.88 g, 40.0 mmol) in N,N-dimethylacetamide (25 mL) was added slowly to the reaction mixture. The resulting suspension was then stirred at room temp for 18 h. Water (100 mL) was added to the reaction mixture and the solution filtered through celite. The filtrate was diluted with EtOAc (250 mL) and organic layer was washed with $H_2O$ (50 mL), $NaHCO_3$ (5%, 50 mL) and $H_2O$ (50 mL). The solvent was removed and the residue was purified by column chromatography on silica gel, eluting with hexanes/EtOAc (4:1) to provide a colorless oil (11.75 g, 82%): $^1H$ NMR (300 MHz, $CDCl_3$) δ 7.51 (d, 1H), 7.49 (s, 1H), 7.19 (d, 1H), 4.26 (m, 4H), 2.36 (s, 3H), 1.48 (s, 9H), 137 (m, 6 H).

Procedure N

[(2-Bromo-4-bromomethyl-phenyl)-difluoro-methyl]-phosphonic acid diethyl ester: A solution of [(2-bromo-4-methyl-phenyl)-difluoro-methyl]-phosphonic acid diethyl ester (10.93 g, 30.6 mmol), N-bromosuccinimide (5.45 g, 30.6 mmol) and AIBN (100 mg) in benzene (300 mL) was refluxed for 18 h. The reaction mixture was concentrated in vacuo and redissolved in Ethyl acetate (200 mL). The solution was washed with $H_2O$ (50 mL), HCl (1 N, 50 mL), $NaHCO_3$ (5%, 50 mL) and $H_2O$ (50 mL). The solvent was removed and the residue was purified by column chromatography on silica gel, eluting with hexanes/EtOAc (4:1) to provide a colorless oil (9.6 g, 80% purity with starting material as byproduct), which was taken on to the next step without further purification.

Procedure O 3-(3-{5-[{3-Chloro-4-[(diethoxy-phosphoryl)-difluoro-methyl]-benzyl}-(3,4-dichloro-phenyl)-amino]-[1,3,4]thiadiazol-2-yl}-phenoxy)-benzoic acid methyl ester and 3-{3-[4-{3-chloro-4-[(diethoxy-phosphoryl)-difluoro-methyl]-benzyl}-5-(3,4-dichloro-phenylimino)-4,5-dihydro-[1,3,4]thiadiazol-2-yl]-phenoxy}-benzoic acid methyl ester: A solution of 3-{3-[5-(3,4-dichloro-phenylamino)-[1,3,4]thiadiazol-2-yl]-phenoxy}-benzoic acid methyl ester (1.42 g, 3.0 mmol) and NaH (60%, 0.14 g, 3.6 mmol) in DMF (20 mL) was stirred at room temp for 1 h. A solution of [(2-chloro-4-bromomethyl-phenyl)-difluoro-methyl]-phosphonic acid diethyl ester (1.41 g, 3.6 mmol) in DMF (10 mL) was added and the reaction mixture was stirred at room temp for 16 h. The NaH was carefully quenched with water (20 mL) and reaction mixture concentrated in vacuo. The residue was dissolved in EtOAc (150 mL) and organic layer was washed with $H_2O$ (50 mL), $NaHCO_3$ (5%, 50 mL) and $H_2O$ (50 mL). The solvent was removed to provide a residue, which was purified by column chromatography on silica gel, eluting with hexanes/EtOAc (7:3) to provide 3-{3-[4-{3-chloro-4-[(diethoxy-phosphoryl)-difluoro-methyl]-benzyl}-5-(3,4-dichloro-phenylimino)-4,5-dihydro-[1,3,4]thiadiazol-2-yl]-phenoxy}-benzoic acid methyl ester (0.50 g, 21%) as a sticky oil. This compound is the iso version of the thiadiazole. Further elution with hexanes/EtOAc (1:1) to provide a white solid as 3-(3-{5-[{3-chloro-4-[(diethoxy-phosphoryl)-difluoro-methyl]-benzyl}-(3,4-dichloro-phenyl)-amino]-[1,3,4]thiadiazol-2-yl}-phenoxy)-benzoic acid methyl ester (0.95 g, 40%). This compound is the normal version of the thiadiazole. All the thiadiazole compounds during alkylation gave an approx. 1:3 ratio of the iso: normal form of the alkylated product.

EXAMPLE 1

3-(3-{5-Benzoylimino-4-[3-bromo-4-(difluoro-phosphono-methyl)-benzyl]-4,5-dihydro-[1,3,4]thiadiazol-2-yl}-phenoxy)-benzoic acid A solution of 3-[3-(5-amino-[1,3,4]thiadiazol-2-yl)-phenoxy]-benzoic acid methyl ester (5.69 g, 17.4 mmol), benzoyl chloride (2.93 g, 20.9 mmol) and DMAP (6.37 g, 52.1 mmol) in $CH_2Cl_2$ (100 mL) was stirred at room temp for 15 h. Another 100 mL of $CH_2Cl_2$ was added. The $CH_2Cl_2$ solution was washed with $H_2O$ (50 mL), HCl (1N, 50 mL), $NaHCO_3$ (5%, 50 mL) and $H_2O$ (50 mL). The solvent was removed to provide a white solid (6.16 g, 82%) as 3-[3-(5-benzoylamino-[1,3,4]thiadiazol-2-yl)-phenoxy]-benzoic acid methyl ester.

As described in procedure J, only 3-[3-(5-benzoylimino-4-{3-bromo-4-[(diethoxy-phosphoryl)-difluoro-methyl]-benzyl}-4,5-dihydro-[1,3,4]thiadiazol-2-yl)-phenoxy]-benzoic acid methyl ester was prepared by alkylation.

As described in procedure K and L, the title compound was prepared: $^1H$ NMR (300 MHz, DMSO-$d_6$) δ 8.27 (d, 2H), 7.88 (s, 1H), 7.77-7.52 (overlapping, 11H), 7.38 (dd, 1H), 7.26 (dd, 1H), 5.78 (s, 2H).

EXAMPLE 2

3-{3-[4-[3-Bromo-4-(difluoro-phosphono-methyl)-benzyl]-5-(3,4-dichloro-benzoylimino)-4,5-dihydro-[1,3,4]thiadiazol-2-yl]-phenoxy}-benzoic acid The title compound was prepared as described for example 1: $^1H$ NMR (300 MHz, DMSO-$d_6$) δ 8.38 (s, 1H), 8.20 (d, 1H), 7.87 (s, 1H), 7.78-7.49 (overlapping, 9H), 7.38 (d, 1H), 7.286 (d, 1H), 5.81 (s, 2H); Mass: 391.5, 392.5 (M/2−1)

EXAMPLE 3

3-{3-[4-[3-Bromo-4-(difluoro-phosphono-methyl)-benzyl]-5-(3-trifluoromethyl-benzoylimino)-4,5-dihydro-[1,3,4]thiadiazol-2-yl]-phenoxy}-benzoic acid The title compound was prepared as as described for example 1: $^1$H NMR (300 MHz, DMSO-$d_6$) δ 8.55 (d, 1H), 8.48 (s, 1H), 7.97 (d, 1H), 7.85-7.51 (overlapping, 9H), 7.38 (d, 1H), 7.28 (d, 1H), 5.80 (s, 2H); Mass: 390.5, 391.2 (M/2−1).

EXAMPLE 4

3-{3-[4-[3-Bromo-4-(difluoro-phosphono-methyl)-benzyl]-5-(3-chloro-phenylimino)-4,5-dihydro-[1,3,4]thiadiazol-2-yl]-phenoxy}-benzoic acid The title compound was prepared as described for example 6. $^1$H NMR (300 MHz, DMSO-$d_6$) δ 7.77-7.00 (m, 15 H), 5.36 (s, 2 H); LCMS m/z 360 [M/2−1].

EXAMPLE 5

3-(3-{4-[3-Bromo-4-(difluoro-phosphono-methyl)-benzyl]-5-phenylimino-4,5-dihydro-[1,3,4]thiadiazol-2-yl}-phenoxy)-benzoic acid The title compound was prepared as described for example 6. $^1$H NMR (300 MHz, DMSO-$d_6$) δ 7.78-7.02 (m, 16 H), 5.36 (s, 2 H); LCMS m/z 343 [M/2−1].

EXAMPLE 6

3-{3-[4-[3-Bromo-4-(difluoro-phosphono-methyl)-benzyl]-5-(3,4-dichloro-phenylimino)-4,5-dihydro-[1,3,4]thiadiazol-2-yl]-phenoxy}-benzoic acid As described in procedure L, the title compound was prepared: mp: 210-215° C.; $^1$H NMR (300 MHz, DMSO-$d_6$) δ 7.81 (s, 1H), 7.77 (d, 1H), 7.67-7.37 (overlapping, 10H), 7.24 (m, 1H), 7.11 (dd, 1H), 5.42 (s, 2H); Mass: 377.5, 378.5 (M/2−1).

EXAMPLE 7

3-{3-[4-[3-Bromo-4-(difluoro-phosphono-methyl)-benzyl]-5-(4-chloro-phenylimino)-4,5-dihydro-[1,3,4]thiadiazol-2-yl]-phenoxy}-benzoic acid The title compound was prepared as described for example 6. $^1$H NMR (300 MHz, DMSO-$d_6$) δ 7.76-7.04 (m, 15 H), 5.35 (s, 2 H); LCMS m/z 360 [M/2−1].

EXAMPLE 8

3-{3-[4-[3-Chloro-4-(difluoro-phosphono-methyl)-benzyl]-5-(3,4-dichloro-phenylimino)-4,5-dihydro-[1,3,4]thiadiazol-2-yl]-phenoxy}-benzoic acid The title compound was prepared using procedure L: mp: 212-215° C.; $^1$H NMR (300 MHz, DMSO-$d_6$) δ 7.72 (d, 1H), 7.60-7.31 (overlapping, 11H), 7.18 (dd, 1H), 7.06 (dd, 1H), 5.37 (s, 2H); Mass: 710, 712 (M−1), 354.5, 355.5 (M/2−1).

EXAMPLE 9

3-{3-[4-[3-Chloro-4-(difluoro-phosphono-methyl)-benzyl]-5-(3,4-dichloro-phenylimino)-4,5-dihydro-[1,3,4]thiadiazol-2-yl]-phenoxy}-benzoic acid methyl ester The title compound was prepared using procedure M, N, O and K: mp: 137-139° C.; $^1$H NMR (300 MHz, DMSO-$d_6$) δ 7.73 (d, 1H), 7.61-7.27 (overlapping, 11H), 705 (d, 1H), 7.02 (d, 1H), 5.35 (s, 2H), 3.79 (s, 3H); Mass: 724, 726, 728 (M−1), 362.5 (M/2−1).

EXAMPLE 10

3-(3-{5-(3,4-Dichloro-phenylimino)-4-[4-(difluoro-phosphono-methyl)-3-fluoro-benzyl]-4,5-dihydro-[1,3,4]thiadiazol-2-yl}-phenoxy)-benzoic acid The title compound was prepared as as described for example 41: mp: 153-156° C.; $^1$H NMR (300 MHz, DMSO-$d_6$) δ 7.74 (d, 1H), 7.62-7.33 (overlapping, 11H), 7.19 (dd, 1H), 7.08 (dd, 1H), 5.40 (s, 2H); Mass: 696 (M+1), 694 (M−1), 347.3 (M/2−1).

EXAMPLE 11

3-(3-{5-(3,4-Dichloro-phenylimino)-4-[4-(difluoro-phosphono-methyl)-3-fluoro-benzyl]-4,5-dihydro-[1,3,4]thiadiazol-2-yl}-phenoxy)-benzoic acid methyl ester The title compound was prepared as as described for example 46: mp: 137-139° C.; $^1$H NMR (300 MHz, DMSO-$d_6$) δ 7.74 (d, 1H), 7.60-7.49 (overlapping, 5H), 7.40-7.17 (overlapping, 7H), 7.08 (dd, 1H), 5.35 (s, 2H), 3.83 (s, 3H).

EXAMPLE 12

3-{3-[4-[3-Bromo-4-(difluoro-phosphono-methyl)-benzyl]-5-(3,4-dichloro-phenylimino)-4,5-dihydro-[1,3,4]thiadiazol-2-yl]-phenoxy}-benzoic acid methyl ester As described in procedure K, the title compound was prepared from 3-{3-[4-{3-bromo-4-[(diethoxy-phosphoryl)-difluoro-methyl]-benzyl}-5-(3,4-dichloro-phenylimino)-4,5-dihydro-[1,3,4]-thiadiazol-2-yl]-phenoxy}-benzoic acid methyl ester: $^1$H NMR (300 MHz, DMSO-$d_6$) δ 7.73 (s, 1H), 7.71 (d, 1H), 7.59-7.29 (overlapping, 10H), 7.16 (m, 1H), 7.03 (dd, 1H), 5.34 (s, 2H), 3.79 (s, 3H); Mass: 384.3, 384.9 (M/2−1).

EXAMPLE 13

N-(4-{2-[[3-Bromo-4-(difluoro-phosphono-methyl)-benzyl]-(3,4-dichloro-phenyl)-amino]-thiazol-4-yl}-phenyl)-oxalamic acid The title compound was prepared as per procedure L using the compound of example 21. $^1$H NMR (600 MHz, D$_2$O) δ 7.4-6.4 (m, 11 H), 4.70 (s, 2H); LCMS m/z 708 [M+1].

EXAMPLE 14

(3-{2-[[3-Bromo-4-(difluoro-phosphono-methyl)-benzyl]-(3,4-dichloro-phenyl)-amino]-thiazol-4-yl}-phenoxy)-phenyl-acetic acid To 3-hydroxy acetophenone (5 g, 36.72 mmol) in 100 ml of acetone was added $K_2CO_3$ (6.09 g, 44.06 mmol) followed by the addition of methyl α-bromo phenyl acetate (10 g, 44.06 mmol) and the reaction was stirred at room temperature overnight. The reaction mixture was filtered, concentrated and purified via column chromatography (5/1 hexanes/ethyl acetate) to yield 8.15 g (84%) of (3-acetyl-phenoxy)-phenyl-acetic acid methyl ester as a clear, colorless oil; $^1$H NMR (600 MHz, $CDCl_3$) δ δ 7.60-7.17 (m, 9 H), 5.74 (s, 1 H), 3.76 (s, 3H), 2.59 (s, 3 H).

[3-(2-Bromo-acetyl)-phenoxy]-phenyl-acetic acid methyl ester was synthesized from (3-acetyl-phenoxy)-phenyl-acetic acid methyl ester and bromine as described in example 31.

{3-[2-(3,4-Dichloro-phenylamino)-thiazol-4-yl]-phenoxy}-phenyl-acetic acid methyl ester was prepared as per procedure I using (3,4-dichloro-phenyl)-thiourea and [3-(2-Bromo-acetyl)-phenoxy]-phenyl-acetic acid methyl ester using Procedure I.

(3-{2-[{3-Bromo-4-[(diethoxy-phosphoryl)-difluoro-methyl]-benzyl}-(3,4-dichloro-phenyl)-amino]-thiazol-4-yl}-phenoxy)-phenyl-acetic acid methyl ester was synthesized as per procedure J.

The title compound (3-{2-[[3-Bromo-4-(difluoro-phosphono-methyl)-benzyl]-(3,4-dichloro-phenyl)-amino]-thiazol-4-yl}-phenoxy)-phenyl-acetic acid was synthesized using procedure K and L. $^1$H NMR (600 MHz, DMSO-$d_6$) δ 7.95-7.29 (m, 15 H), 6.89 (d, 1 H), 5.86 (s, 1 H), 5.32 (s, 2 H); LCMS m/z 768 [M+1].

EXAMPLE 15

4-{2-[[3-Bromo-4-(difluoro-phosphono-methyl)-benzyl]-(4'-carboxyphenyl amino]-thiazol-4-yl}-benzoic acid The title compound was prepared as described for example 17. $^1$H NMR (300 MHz, DMSO-$d_6$) δ 7.99-7.42 (m, 12H), 5.40 (s, 2 H); LCMS m/z 638 [M−1].

EXAMPLE 16

4-{2-[[3-Bromo-4-(difluoro-phosphono-methyl)-benzyl]-(4-trifluoromethyl-phenyl)-amino]-thiazol-4-yl}-benzoic acid The title compound was prepared as described for example 17. $^1$H NMR (300 MHz, DMSO-$d_6$) δ 7.98-7.42 (m, 12H), 5.40 (s, 2 H); LCMS m/z 664 [M+1].

EXAMPLE 17

4-{2-[[3-Bromo-4-(difluoro-phosphono-methyl)-benzyl]-(3,4-dichloro-phenyl)-amino]-thiazol-4-yl}-benzoic acid The reaction described in Procedure L was repeated to synthesize the title compound, 4-{2-[[3-Bromo-4-(difluoro-phosphono-methyl)-benzyl]-(3,4-dichloro-phenyl)-amino]-thiazol-4-yl}-benzoic acid. $^1$H NMR (300 MHz, DMSO-$d_6$) δ 7.97-7.44 (m, 11H), 5.33 (s, 2 H); LCMS m/z 663 [M−1].

EXAMPLE 18

{[2-Bromo-4-({[4-(4-methanesulfonyl-phenyl)-thiazol-2-yl]-phenyl-amino}-methyl)-phenyl]-difluoro-methyl}-phosphonic acid The title compound was prepared as described for example 20. $^1$H NMR (300 MHz, DMSO-$d_6$) δ 8.11(d, J=3.9 Hz, 2 H), 7.93 (d, J=3.9 Hz, 2 H), 7.71-7.32 (m, 9 H), 5.31 (s, 2 H), 3.59 (s, 3 H); LCMS m/z 631 [M+1].

EXAMPLE 19

N-[4-(2-{[3-Bromo-4-(difluoro-phosphono-methyl)-benzyl]-phenyl-amino}-thiazol-4-yl)-phenyl]-oxalamic acid ethyl ester The title compound was prepared as described for example 21. $^1$H NMR (600 MHz, DMSO-$d_6$) δ 7.85-7.18 (m, 13 H), 5.30 (s, 2 H), 4.31 (q, 2 H), 1.31 (t, 3 H); LCMS m/z 667 [M+1].

EXAMPLE 20

{[2-Bromo-4-({(3,4-dichloro-phenyl)-[4-(4-methanesulfonyl-phenyl)-thiazol-2-yl]-amino}-methyl)-phenyl]-difluoro-methyl}-phosphonic acid (3,4-Dichloro-phenyl)-[4-(4-methanesulfonyl-phenyl)-thiazol-2-yl]-amine was prepared in 78% yield using the procedure described in example 31 from 2-Bromo-1-(4-methanesulfonyl-phenyl)-ethanone and (3,4-Dichloro-phenyl)-thiourea. $^1$H NMR (300 MHz, DMSO-$d_6$) δ 8.16-7.56 (m, 8H), 3.24 (s, 3H).

{[2-Bromo-4-({(3,4-dichloro-phenyl)-[4-(4-methanesulfonyl-phenyl)-thiazol-2-yl]amino}-methyl)-phenyl]-difluoro-methyl}-phosphonic acid diethyl ester was synthesized using procedure J in 65% yield.

The title compound {[2-Bromo-4-({(3,4-dichloro-phenyl)-[4-(4-methanesulfonyl-phenyl)-thiazol-2-yl]-amino}-methyl)-phenyl]-difluoro-methyl}-phosphonic acid was prepared as described in procedure K. $^1$H NMR (300 MHz, DMSO-$d_6$) δ 8.11-7.46 (m, 11H), 5.34 (s, 2 H; LCMS m/z 696 [M−1].

EXAMPLE 21

N-(4-{2-[[3-Bromo-4-(difluoro-phosphono-methyl)-benzyl]-(3,4-dichloro-phenyl)-amino]-thiazol-4-yl}-phenyl)-oxalamic acid ethyl ester N-(4-Acetyl-phenyl)-ethyl oxalate was synthesized from p-amino acetophenone by treatment with ethyl oxalyl chloride in THF at room temperature.

N-[4-(2-Bromo-acetyl)-phenyl]-ethyl oxalate was synthesized from N-(4-Acetyl-phenyl)-ethyl oxalate and bromine as described in example 31.

N-{4-[2-(3,4-Dichloro-phenylamino)-thiazol-4-yl]-phenyl}-ethyl oxalate was synthesized as per procedure I from (3,4-dichloro-phenyl)-thiourea and N-[4-(2-Bromo-acetyl)-phenyl]-ethyl oxalate.

The title compound was prepared as described for example 17. $^1$H NMR (300 MHz, DMSO-$d_6$) δ 7.97-7.31 (m, 11 H), 5.32 (s, 2 H), 4.26 (q, 2 H), 1.27 (t, 3 H); LCMS m/z 736 [M+1].

EXAMPLE 22

4-(2-{[3-Bromo-4-(difluoro-phosphono-methyl)-benzyl]-naphthalen-1-yl-amino}-thiazol-4-yl)-benzoic acid The title compound was prepared as described for example 17. $^1$H NMR (300 MHz, DMSO-d$_6$) δ 8.06-7.33 (m, 15 H), 5.58 (s, 1 H), 4.97 (s, 1 H); LCMS m/z 646 [M+1].

EXAMPLE 23

3-(4-{2-[[3-Bromo-4-(difluoro-phosphono-methyl)-benzyl]-(3,4-dichloro-phenyl)-amino]-thiazol-4-yl}-phenyl)-acrylic acid The title compound was prepared as described for example 17. $^1$H NMR (300 MHz, DMSO-d$_6$) δ 7.98-7.45 (m, 12 H), 6.53 (d, 1 H), 5.33 (s, 2 H); LCMS m/z 345 [M/2−1].

EXAMPLE 24

(4-{2-[[3-Bromo-4-(difluoro-phosphono-methyl)-benzyl]-(3,4-dichloro-phenyl)-amino]-5-methyl-thiazol-4-yl}-phenoxy)-acetic acid The reaction described in Procedure L was repeated to synthesize the title compound, 4-{2-[[3-Bromo-4-(difluoro-phosphono-methyl)-benzyl]-(3,4-dichloro-phenyl)-amino]-thiazol-4-yl}-benzoic acid. $^1$H NMR (300 MHz, DMSO-d$_6$) δ 7.90-7.40 (m, 8H), 6.94 (d, J=9.0 Hz, 2H), 5.24 (s, 2 H); 4.69 (s, 2H), 2.34 (s, 3H); LCMS m/z 706 [M−1].

EXAMPLE 25

4-{2-[[3-Bromo-4-(difluoro-phosphono-methyl)-benzyl]-(4'-ethoxycarbonylphenyl amino]-thiazol-4-yl}-benzoic acid methyl ester As described in Procedure I, 4-[2-(4'-ethoxycarbonylphenyl amino)-thiazol-4-phenyl]-methyl benzoate was prepared from 1-(4-ethoxycarbonylphenyl)-2-thiourea and 4-(2-bromoacetyl)-methyl benzoate in 85% yield.

The title compound was prepared as described for example 31 from 4-[2-(4'-ethoxycarbonylphenyl amino)-thiazol-4-phenyl]-methyl benzoate and [(2-Bromo-4-bromomethyl-phenyl)-difluoro-methyl]-phosphonic acid diethyl ester. $^1$H NMR (300 MHz, DMSO-d$_6$) δ 8.04-7.40 (m, 12H), 5.39 (s, 2 H), 4.29 (q, J=7.2 Hz, 2H), 3.84 (s, 3H), 1.29 (t, J=7.5 Hz, 3H); LCMS m/z 682 [M+1].

EXAMPLE 26

4-{2-[[3-Bromo-4-(difluoro-phosphono-methyl)-benzyl]-(4-trifluoromethyl-phenyl) amino]-thiazol-4-yl}-benzoic acid methyl ester The title compound was prepared as described for example 31. $^1$H NMR (300 MHz, DMSO-d$_6$) δ 7.98-7.42 (m, 12H), 5.40 (s, 2 H), 3.84 (s, 3 H); LCMS m/z 678 [M+1].

EXAMPLE 27

4-(2-{([3-Bromo-4-(difluoro-phosphono-methyl)-benzyl]-naphthalen-1-yl-amino}-thiazol-4-yl)-benzoic acid methyl ester The title compound was prepared as described for example 31. $^1$H NMR (300 MHz, DMSO-d$_6$) δ 8.05-7.34 (m, 15 H), 5.62 (s, 1 H), 4.98 (s, 1 H), 3.82 (s, 3 H); LCMS m/z 660 [M+1].

EXAMPLE 28

5-{2-[[3-Bromo-4-(difluoro-phosphono-methyl)-benzyl]-(3,4-dichloro-phenyl)-amino]-thiazol-4-yl}-2-hydroxy-benzoic acid methyl ester 5-(2-Bromo-acetyl)-2-hydroxy-methyl benzoate is prepared from 5-Acetyl-2-hydroxy-methylbenzoate using the procedure described in example 31.

5-[2-(3,4-Dichloro-phenylamino)-thiazol-4-yl]-2-hydroxy-methyl benzoate was prepared using procedure described in example 31 from 5-(2-Bromo-acetyl)-2-hydroxy-methyl benzoate and (3,4-Dichloro-phenyl)-thiourea. $^1$H NMR (300 MHz, DMSO-d$_6$) δ 8.37-7.36 (m, 6H), 7.06 (d, 1H), 3.93 (s, 3H).

To 5-[2-(3,4-Dichloro-phenylamino)-thiazol-4-yl]-2-hydroxy-methyl benzoate (3 g, 7.59 mmol) in DCM was added t-butyldimethylsilyl chloride (1.37 g, 9.11 mmol) and triethylamine (0.92 g, 9.1 mmol) and reaction stirred overnight at room temperature. When the reaction was complete the organic layer was washed with sat. sat. NaHCO$_3$, and brine, and the organic layer was dried over NaSO$_4$, and concentrated in vacuo. The resulting material was purified via column chromatography (4/1 hexanes/ethyl acetate) to yield 2.50 g (65%) of a clear, colorless oil; $^1$H NMR (300 MHz, CDCl$_3$) δ δ 8.22-6.79 (m, 7H), 3.89 (s, 3H), 1.01 (s, 9H), 0.23 (s, 6H).

5-{2-[{3-Bromo-4-[(diethoxy-phosphoryl)-difluoro-methyl]-benzyl}-(3,4-dichloro-phenyl)-amino]-thiazol-4-yl}-2-hydroxy-benzoic acid methyl ester was synthesized using procedure J in 50% yield.

The title compound 5-{2-[[3-Bromo-4-(difluoro-phosphono-methyl)-benzyl)]-(3,4-dichloro-phenyl)-amino]-thiazol-4-yl}-2-hydroxy-benzoic acid methyl ester was prepared as described in procedure K. $^1$H NMR (300 MHz, DMSO-d$_6$) δ 8.25-7.02 (m, 10H), 5.31 (s, 2 H); 3.91 (s, 3 H); LCMS m/z 345 [M/2−1].

EXAMPLE 29

[(2-Bromo-4-{[(3,4-dichloro-phenyl)-(4-phenyl-thiazol-2-yl)-amino]-methyl}-phenyl)-difluoro-methyl]-phosphonic acid As described in Procedure I, (3,4-Dichloro-phenyl)-(4-phenyl-thiazol-2-yl)-amine was prepared in 85% yield.

As described in Procedure J, [(2-Bromo-4-{[(3,4-dichloro-phenyl)-(4-phenyl-thiazol-2-yl)-amino]-methyl}-phenyl)-difluoro-methyl]-phosphonic acid diethyl ester was prepared in 76% yield as a clear, colorless oil; $^1$H NMR (300 MHz, CDCl$_3$) δ 7.84-7.22 (m, 11 H), 6.81 (s, 1 H), 5.23 (s, 2 H), 4.23 (m, 4 H), 1.31 (t, J=7.5 Hz, 6 H).

The reaction described in Procedure K was repeated to synthesize the title compound in 99% yield as a white foam. $^1$H NMR (300 MHz, DMSO-d$_6$) δ 7.99-7.28 (m, 12 H), 5.33 (s, 2 H); LCMS m/z 619 [M−1].

EXAMPLE 30

(4-{2-[[3-Bromo-4-(difluoro-phosphono-methyl)-benzyl]-(3,4-dichloro-phenyl)-amino]-5-methyl-thiazol-4-yl}-phenoxy)-acetic acid ethyl ester As described in Procedure I, 4-[2-(3,4-Dichloro-phenylamino)-5-methyl-thiazol-4-yl]-phenoxy}-acetic acid ethyl ester was prepared from (3,4-Dichloro-phenyl)-thiourea and [4-(2-Bromo-acetyl)-phenoxy]-acetic acid in 90% yield. $^1$H NMR (300 MHz, DMSO-d$_6$) δ 7.52-6.94 (m, 7H), 4.62 (s, 2H), 4.28 (q, J=6.9 Hz, 2 H), 2.38 (s, 3H), 1.32 (t, J=7.2 Hz, 3 H); LCMS m/z 437 [M+1]

As described in Procedure J, (4-{2-[{3-Bromo-4-[(diethoxy-phosphoryl)-difluoro-methyl]-benzyl}-(3,4-dichloro-phenyl)-amino]-5-methyl-thiazol-4-yl}-phenoxy)-acetic acid ethyl ester was prepared in 76% yield as a clear, colorless oil; $^1$H NMR (300 MHz, CDCl$_3$) δ 7.70-7.26 (m, 8 H), 6.94 (d, 2 H), 5.14 (s, 2 H), 4.64 (s, 2H), 4.31-4.20 (m, 4 H), 2.37 (s, 3H), 1.31 (m, 6 H).

The reaction described in Procedure K was repeated to synthesize the title compound in 99% yield as a white foam. $^1$H NMR (300 MHz, CDCl$_3$) δ 7.92-7.41 (m, 8 H), 6.97 (d, 2 H), 5.25 (s, 2 H), 4.80 (s, 2H), 4.18 (q, J=7.2 Hz, 4 H), 2.35 (s, 3H), 1.22 (t, J=7.2 Hz, 6 H).

EXAMPLE 31

4-{2-[[3-Bromo-4-(difluoro-phosphono-methyl)-benzyl]-(3,4-dichloro-phenyl)-amino]-thiazol-4-yl}-benzoic acid methyl ester To a solution of methyl-4-acetyl benzoate (5 g, 28 mmol) in 50 mL of CHCl$_3$ was added bromine (4.48 g, 28 mmol) in 15 mL of CHCl$_3$. When the reaction was complete, water was added carefully to the reaction mixture and the organic layer was washed with sat. NaHCO$_3$ and brine. The organic layer was dried over MgSO4, and concentrated in vacuo to yield 4-(2-Bromo-acetyl)-methyl benzoate, which was used in the next step without purification. $^1$H NMR (300 MHz, CDCl$_3$) δ 8.40 (s, 1H), 8.13 (d, J=8.0 Hz, 2H), 8.02 (d, J=7.8 Hz, 2H), 4.46 (s, 2 H); 3.95 (s, 3 H).

As described in Procedure I, 4-[2-(3,4-Dichloro-phenylamino)-thiazol-4-yl]-methyl benzoate was prepared from (3,4-Dichloro-phenyl)-thiourea and 4-(2-Bromo-acetyl)-methyl benzoate in 85% yield. $^1$H NMR (300 MHz, DMSO-d$_6$) δ 10.7 (s, 1H), 8.13-7.56 (m, 8H), 3.86 (s, 3H); LCMS m/z 380 [M+1]

As described in Procedure J, 4-{2-[{3-Bromo-4-[(diethoxy-phosphoryl)-difluoro-methyl]-benzyl}-(3,4-dichloro-phenyl)-amino]-thiazol-4-yl}-methyl benzoate was prepared in 65% yield as a clear, colorless oil; $^1$H NMR (300 MHz, CDCl$_3$) δ 8.07-7.21 (m, 10 H), 6.93 (s, 1 H), 5.22 (s, 2 H), 4.25-4.18 (m, 4 H), 3.93 (s, 3H), 1.31 (t, J=7.5 Hz, 6 H).

The reaction described in Procedure K was repeated to synthesize the title compound, 4-{2-[[3-Bromo-4-(difluoro-phosphono-methyl)-benzyl]-(3,4-dichloro-phenyl)-amino]-thiazol-4-yl}-methyl benzoate in 95% yield as a white foam. $^1$H NMR (300 MHz, DMSO-d$_6$) δ 7.99-7.44 (m, 11 H), 5.34 (s, 2 H), 3.85 (s, 3H); LCMS m/z 678 [M+1].

EXAMPLE 32

[(2-Bromo-4-{[(3,4-dichloro-phenyl)-(4-naphthalen-2-yl-thiazol-2-yl)-amino]methyl}-phenyl)-difluoro-methyl]-phosphonic acid As described in Procedure I, (3,4-Dichloro-phenyl)-(4-naphthalen-1-yl-thiazol-2-yl)-amine was prepared from (3,4-Dichloro-phenyl)-thiourea and 2-Bromo-1-naphthalen-1-yl-ethanone in 99% yield. $^1$H NMR (300 MHz, DMSO-d$_6$) δ 10.7 (s, 1H), 8.25-7.49 (m, 11H), LCMS m/z 371 [M+1]

As described in Procedure J, [(2-Bromo-4-{[(3,4-dichloro-phenyl)-(4-naphthalen-2-yl-thiazol-2-yl)-amino]-methyl}-phenyl)-difluoro-methyl]-phosphonic acid diethyl was prepared in 75% yield as a clear, colorless oil; $^1$H NMR (300 MHz, CDCl$_3$) δ 7.91-7.22 (m, 13 H), 6.91 (s, 1 H), 5.25 (s, 2 H), 4.26-4.13 (m, 4 H), 1.31 (t, J=7.5 Hz, 6 H).

The reaction described in Procedure K was repeated to synthesize the title compound in 99% yield as a white foam. $^1$H NMR (300 MHz, DMSO-d$_6$) δ 8.40 (s, 1H), 8.08-7.48 (m, 13 H), 5.38 (s, 2 H); LCMS m/z 669 [M−1]

EXAMPLE 33

[2-Bromo-4-({(3,4-dichloro-phenyl)-[4-(4-methanesulfonyl-phenyl)-thiazol-2-yl]-amino}-methyl)-phenoxy]-acetic acid The title compound was prepared as described for example 20. $^1$H NMR (300 MHz, DMSO-d$_6$) δ 8.12-7.50 (m, 9H), 7.29 (d, 1 H), 6.91 (d, 1 H), 6.52 (d, 1 H), 5.22 (s, 2 H), 4.75 (s, 2 H), 3.22 (s, 3 H); LCMS m/z 643 [M+1].

EXAMPLE 34

3-[2-Bromo-4-({(3,4-dichloro-phenyl)-[4-(4-methanesulfonyl-phenyl)-thiazol-2-yl]-amino}-methyl)-phenyl]-acrylic acid The title compound was prepared as described for example 20. $^1$H NMR (300 MHz, DMSO-d$_6$) δ 8.10-7.38 (m, 12H), 6.52 (d, 1 H), 5.31 (s, 2 H), 3.22 (s, 3 H); LCMS m/z 639 [M+1].

EXAMPLE 35

4-({(3,4-Dichloro-phenyl)-[4-(4-methanesulfonyl-phenyl)-thiazol-2-yl]-amino}-methyl)-phenyl]-difluoro-acetic acid The title compound was prepared as described for example 20. $^1$H NMR (300 MHz, DMSO-d$_6$) δ 8.09-7.50 (m, 12 H), 5.36 (s, 2 H), 3.21 (s, 3 H); LCMS m/z 584 [M+1].

EXAMPLE 36

3-{3-[4-[3-Bromo-4-(difluoro-phosphono-methyl)-benzyl]-5-(3-trifluoromethyl-benzoylimino)-4,5-dihydro-[1,3,4]thiadiazol-2-yl]-phenoxy}-benzoic acid The title compound was prepared as as described for example 1: $^1$H NMR (300 MHz, DMSO-d$_6$) δ 8.55 (d, 1H), 8.48 (s, 1H), 7.97 (d, 1H), 7.85-7.51 (overlapping, 9H), 7.38 (d, 1H), 7.28 (d, 1H), 5.80 (s, 2H); Mass: 390.5, 391.2 (M/2−1).

EXAMPLE 37

4-{2-[(3-Bromo-4-carboxymethoxy-benzyl)-(3,4-dichloro-phenyl)-amino]-thiazol-4-yl}-benzoic acid The title compound was prepared as described for example 31 and 17 from 4-[2-(3,4-Dichloro-phenylamino)-thiazol-4-yl]-methyl benzoate and (2-Bromo-4-bromomethyl-phenoxy)-acetic acid methyl ester. $^1$H NMR (300 MHz, DMSO-d$_6$) δ 8.00-7.51 (m, 9H), 7.30 (d, J=8.4 Hz, 1H), 6.93 (d, J=9.0 Hz, 1H), 5.22 (s, 2 H); 4.75 (s, 2H); LCMS m/z 606 [M−1].

EXAMPLE 38

2-Bromo-4-{[[4-(4-carboxy-phenyl)-thiazol-2-yl]-(3,4-dichloro-phenyl)-amino]-methyl}-benzoic acid The title compound was prepared as described for example 31 and 17 from 4-[2-(3,4-Dichloro-phenylamino)-thiazol-4-yl]-benzoic acid methyl ester and 2-Bromo-4-bromomethyl-methyl benzoate. $^1$H NMR (300 MHz, DMSO-d$_6$) δ 7.97-7.44 (m, 11H), 5.35 (s, 2 H); LCMS m/z 576 [M−1].

EXAMPLE 39

4-(2-{Benzenesulfonyl-[3-bromo-4-(difluoro-phosphono-methyl)-benzyl]-amino}-thiazol-4-yl)-benzoic acid methyl ester Following the procedure as described in example 31, 4-(2-bromo-acetyl)-benzoic acid methyl ester was prepared from 4-acetyl-benzoic acid methyl ester and bromine.

As described in procedure I, 4-(2-amino-thiazol-4-yl)-benzoic acid methyl ester was prepared from 4-(2-bromo-acetyl)-benzoic acid methyl ester.

A mixture of 4-(2-amino-thiazol-4-yl)-benzoic acid methyl ester (1.17 g, 5 mmol), benzenesulfonyl chloride (1.06 g, 6 mmol) and 4-dimethylaminopyridine (2.20 g, 18 mmol) in $CH_2Cl_2$ (50 mL) was stirred at room temp for 18 h. A white solid was provided as 4-(2-benzenesulfonylamino-thiazol-4-yl)-benzoic acid methyl ester.

The title compound was prepared as described in procedure J, K. $^1$H NMR (300 MHz, DMSO-$d_6$) δ 7.98-7.96 (overlapping, 7H), 7.82 (s, 1H), 7.80 (d, 1H), 7.68 (d, 2H), 7.58 (d, 2H), 5.28 (s, 2H), 3.85 (s, 3H); 675 (M+1).

EXAMPLE 40

4-(2-{Benzenesulfonyl-[3-bromo-4-(difluoro-phosphono-methyl)-benzyl]-amino}-thiazol-4-yl)-benzoic acid As described in procedure L, the title compound was prepared: $^1$H NMR (300 MHz, DMSO-$d_6$) δ 7.99 (d, 2H), 7.96-7.93 (overlapping, 5H), 7.83 (s, 1H), 7.79 (d, 1H), 7.69 (d, 2H), 7.59 (d, 2H), 5.28 (s, 2H); LC-MS 661 (M+1).

EXAMPLE 41

[(2-Bromo-4-{[(3,4-dichloro-phenyl)-(5-{3-[3-(1H-tetrazol-5-yl)-phenoxy]-phenyl}-[1,3,4]thiadiazol-2-yl)-amino]-methyl}-phenyl)-difluoro-methyl]-phosphonic acid As described in procedure O, [(2-bromo-4-{[{5-[3-(3-cyano-phenoxy)-phenyl]-[1,3,4]thiadiazol-2-yl}-(3,4-dichloro-phenyl)-amino]-methyl}-phenyl)-difluoro-methyl]-phosphonic acid diethyl ester was prepared.

A solution of [(2-bromo-4-{[{5-[3-(3-cyano-phenoxy)-phenyl]-[1,3,4]thiadiazol-2-yl}-(3,4-dichloro-phenyl)-amino]-methyl}-phenyl)-difluoro-methyl]-phosphonic acid diethyl ester (0.40 g, 0.5 mmol), sodium azide (0.13 g, 2.0 mmol) and ammonium chloride (0.11 g, 2.0 mmol) in DMF (5 mL) was heated at 120° C. for 18 h. DMF was removed. The residue was acidified with HCl (conc. 10 mL) and extracted with ethyl acetate (100 mL). Ethyl acetate solution was washed with $H_2O$ (20 mL). Solvent was removed to provide a residue for using in next step without purification.

As described in procedure K, the title compound was prepared from [(2-bromo-4-{[(3,4-dichloro-phenyl)-(5-{3-[3-(1H-tetrazol-5-yl)-phenoxy]-phenyl}-[1,3,4]thiadiazol-2-yl)-amino]-methyl}-phenyl)-difluoro-methyl]-phosphonic acid diethyl ester: mp: 232-235° C.; $^1$H NMR (300 MHz, DMSO-$d_6$) δ 7.99 (d, 1H), 7.84-7.22 (overlapping, 13H), 5.29 (s, 2H); Mass: 389 (M/2-1).

EXAMPLE 42

3-(3-{5-[[3-Bromo-4-(difluoro-phosphono-methyl)-benzyl]-(3,4-dichloro-phenyl)-amino]-[1,3,4]thiadiazol-2-yl}-phenoxy)-benzoic acid As described in procedure L, the title compound was prepared: mp: $^1$H NMR (300 MHz, DMSO-$d_6$) δ 8.03 (d, 1H), 7.75-7.49 (overlapping, 11H), 7.36 (d, 1H), 7.18 (d, 1H), 5.33 (s, 2H); Mass: 377.4, 378.3 (M/2-1).

EXAMPLE 43

3-(3-{5-[[3-Bromo-4-(difluoro-phosphono-methyl)-benzyl]-(4-chloro-phenyl)-amino]-[1,3,4]thiadiazol-2-yl}-phenoxy)-benzoic acid The title compound was prepared as described for example 42. $^1$H NMR (300 MHz, DMSO-$d_6$) δ 7.74-7.14 (m, 15 H), 5.28 (s, 2 H); LCMS m/z 360.5 [M/2-1].

EXAMPLE 44

3-[3-(5-{[3-Bromo-4-(difluoro-phosphono-methyl)-benzyl]-phenyl-amino}-[1,3,4]thiadiazol-2-yl)-phenoxy]-benzoic acid The title compound was prepared as described for example 42. $^1$H NMR (300 MHz, DMSO-$d_6$) δ 7.74-7.13 (m, 16 H), 5.29 (s, 2 H); LCMS m/z 343.5 [M/2-1].

EXAMPLE 45

3-(3-{5-[[3-Bromo-4-(difluoro-phosphono-methyl)-benzyl]-(3-chloro-phenyl)-amino]-[1,3,4]thiadiazol-2-yl}-phenoxy)-benzoic acid The title compound was prepared as described for example 42. $^1$H NMR (300 MHz, DMSO-$d_6$) δ 7.75-7.14 (m, 15 H), 5.31 (s, 2 H); LCMS m/z 360.5 [M/2-1].

EXAMPLE 46

3-(3-{5-[[3-Chloro-4-(difluoro-phosphono-methyl)-benzyl]-(3,4-dichloro-phenyl)-amino]-[1,3,4]thiadiazol-2-yl}-phenoxy)-benzoic acid The title compound was prepared using procedure L: mp: 178-180° C.; $^1$H NMR (300 MHz, DMSO-$d_6$) δ 12.50 (bs, 2H), 8.02 (d, 1H), 7.72 (dd, 2H), 7.62-7.41 (overlapping, 9H), 7.34 (dd, 1H), 7.16 (d, 1H), 5.32 (s, 2H); Mass: 712 (M-1), 354.5, 355.5 (M/2-1).

EXAMPLE 47

3-(3-{5-[[3-Bromo-4-(difluoro-phosphono-methyl)-benzyl]-(3,4-dichloro-phenyl)-amino]-[1,3,4]thiadiazol-2-yl}-phenoxy)-benzoic acid methyl ester As described in procedure M, [(2-bromo-4-methyl-phenyl)-difluoro-methyl]-phosphonic acid diethyl ester was prepared.

As described in procedure N, [(2-bromo-4-bromomethyl-phenyl)-difluoro-methyl]-phosphonic acid diethyl ester was prepared.

As described in procedure J, 3-(3-{5-[{3-bromo-4-[(diethoxy-phosphoryl)-difluoro-methyl]-benzyl}-(3,4-dichloro-phenyl)amino]-[1,3,4]thiadiazol-2-yl}-phenoxy)-benzoic acid methyl ester and 3-{3-[4-{3-bromo-4-[(diethoxy-phosphoryl)-difluoro-methyl]-benzyl}-5-(3,4-dichloro-phenylimino)-4,5-dihydro-[1,3,4]-thiadiazol-2-yl]-phenoxy}-benzoic acid methyl ester were prepared.

As described in procedure K, the title compound was prepared from 3-(3-{5-[{3-bromo-4-[(diethoxy-phosphoryl)-difluoro-methyl]-benzyl}-(3,4-dichloro-phenyl)amino]-[1,3,4]thiadiazol-2-yl}-phenoxy)-benzoic acid methyl ester: $^1$H NMR (300 MHz, DMSO-$d_6$) δ 7.97 (d, 1H), 7.74-7.42 (overlapping, 11H), 7.35 (d, 1H), 7.13 (d, 1H), 5.28 (s, 2H), 3.79 (s, 3H); Mass: 770 (M+1).

EXAMPLE 48

3-(3-{5-[[3-Chloro-4-(difluoro-phosphono-methyl)-benzyl]-(3,4-dichloro-phenyl)-amino]-[1,3,4]thiadiazol-2-yl}-phenoxy)-benzoic acid methyl ester The title compound was prepared using procedure M, N, O and K: mp: 73-76° C.; $^1$H NMR (300 MHz, DMSO-$d_6$) δ 11.90 (bs, 2H), 8.01 (d, 1H), 7.76-7.30 (overlapping, 10H), 7.16 (d, 1H), 7.13 (s, 1H), 6.96 (s, 1H), 5.32 (s, 2H), 3.81 (s, 3H); Mass: 724 (M−1), 362.5, 363.0 (M/2−1).

EXAMPLE 49

3-(3-{5-[[3-Bromo-4-(difluoro-phosphono-methyl)-benzyl]-(3,4-dichloro-benzenesulfonyl)-amino]-[1,3,4]thiadiazol-2-yl}-phenoxy)-benzoic acid The title compound 3-(3-{5-[[3-Bromo-4-(difluoro-phosphono-methyl)-benzyl]-(3,4-dichloro-benzenesulfonyl)-amino]-[1,3,4]thiadiazol-2-yl}-phenoxy)-benzoic acid was prepared as described in procedure L. $^1$H NMR (300 MHz, DMSO-$d_6$) δ 8.71-7.30 (m, 14H), 5.44 (s, 2H); LC-MS 409 [M/2−2].

EXAMPLE 50

4-{2-Benzoylimino-3-[3-bromo-4-(difluoro-phosphono-methyl)-benzyl]-2,3-dihydro-thiazol-4-yl}-benzoic acid methyl ester 4-(2-Benzoylamino-thiazol-4-yl)-benzoic acid methyl ester was prepared from Benzoyl-thiourea and 4-(2-bromoacetyl)-methyl benzoate as described for example 31.

The title compound 4-{2-Benzoylimino-3-[3-bromo-4-(difluoro-phosphono-methyl)-benzyl]-2,3-dihydro-thiazol-4-yl}-benzoic acid methyl ester was prepared as described in procedure in J and K. $^1$H NMR (600 MHz, DMSO-$d_6$) δ 8.00-7.26 (m, 13H), 5.41 (s, 2H), 3.85 (s, 3H); LC-MS 638 [M+1].

EXAMPLE 51

4-(3-{3-Bromo-4-[difluoro-(hydroxy-isopropoxycarbonyloxymethoxy-phosphoryl)-methyl]-benzyl}-2-imino-2,3-dihydro-thiazol-4-yl)-benzoic acid 1-isopropoxycarbonyloxymethyl ester To a solution of 4-{3-[3-bromo-4-(difluorophosphonomethyl)benzyl]-2-imino-2,3-dihydro-thiazol-4-yl}benzoic acid (600 mg, 1.14 mmol) in 8 mL N,N-dimethylformamide under nitrogen atmosphere was added diisopropyl ethylamine (0.99 mL, 5.7 mmol) followed by 708 mg (4.62 mmol) of 1-chloromethyl isopropyl carbonate (prepared according to the procedure in EP 0 682 023) and catalytic amount of NaI (80 mg, 10 mol %). The mixture was stirred at 60° C. for 14 hours. Solvent was evaporated under reduced pressure. The residue was dissolved in 30 mL dichloromethane and washed with 20 mL water followed by 20 mL brine, dried over anhydrous sodium sulphate, filtered and evaporated under reduced pressure. The residue was purified on silica gel column using dichloromethane (400 mL), 25:1 dichloromethane:ethanol (600 mL) and 15:1 dichloromethane:ethanol (600 mL) and then 12:1 dichloromethane:ethanol to elute the compound. Fractions containing pure compound were combined and evaporated to obtain 275 mg (32%) of title compound.

$^1$H NMR (CDCl$_3$, 600 MHz): δ (ppm) 1.31 (s, 12H), 4.50 (s, 2H), 4.94 (m, 1H), 4.96 (m, 1H), 5.61 (s, 2H), 6.00 (s, 2H), 6.84 (s, 1H), 7.28-8.07 (m, 7H); MS (ESI): m/z 750 (M-H)$^+$.

EXAMPLE 52

4-[3-(3-Bromo-4-{difluoro-[hydroxy-(1-isopropoxycarbonyloxyethoxy)-phosphoryl]-methyl}-benzyl)-2-imino-2,3-dihydro-thiazol-4-yl]-benzoic acid isopropoxycarbonyloxy ethyl ester To a solution of 4-{3-[3-bromo-4-(difluorophosphonomethyl)benzyl]-2-imino-2,3-dihydro-thiazol-4-yl}benzoic acid (500 mg, 0.96 mmol) in 8 mL N,N-dimethylformamide under nitrogen atmosphere was added triethylamine (1.06 mL, 7.6 mmol) followed by 1.28 g (7.6 mmol) of 1-chloroethyl isopropyl carbonate (prepared according to the procedure in EP 0 682 023) and catalytic amount of NaI (70 mg, 5 mol %). The mixture was stirred at 80° C. for 36 hours. Solvent was evaporated under reduced pressure. The residue was dissolved in 30 mL dichloromethane and washed with 20 mL water followed by 20 mL brine, dried over anhydrous sodium sulphate, filtered and evaporated under reduced pressure. The residue was purified on silica gel column using dichloromethane (400 mL), 25:1 dichloromethane:ethanol (600 mL) and 20:1 dichloromethane:ethanol (until all the brown impurity come out) and 15:1 dichloromethane:ethanol to elute the compound. Fractions containing pure compound were combined and evaporated to obtain 200 mg (26.7%) of title compound.

$^1$H NMR (DMSO-$d_6$, 600 MHz): δ (ppm) 1.22 (s, 12H), 1.32 (d, J=4.2 Hz, 3H), 1.58 (d, J=4.8 Hz, 3H), 3.03 (m, 1H), 4.50 (s, 2H), 4.72 (m, 1H), 4.79 (m, 1H), 6.22 (m, 1H), 6.86 (s, 1H), 7.36-7.98 (m, 8H), 8.34 (s, 1H); MS (ESI): m/z 778 (M-H)$^+$.

EXAMPLE 53

4-[3-(3-Bromo-4-{[(2,2-dimethyl-propionyloxymethoxy)-hydroxy-phosphoryl]-difluoro-methyl}-benzyl)-2-imino-2,3-dihydro-thiazol-4-yl]-benzoic acid 2,2-dimethyl-propionyloxymethyl ester sodium salt

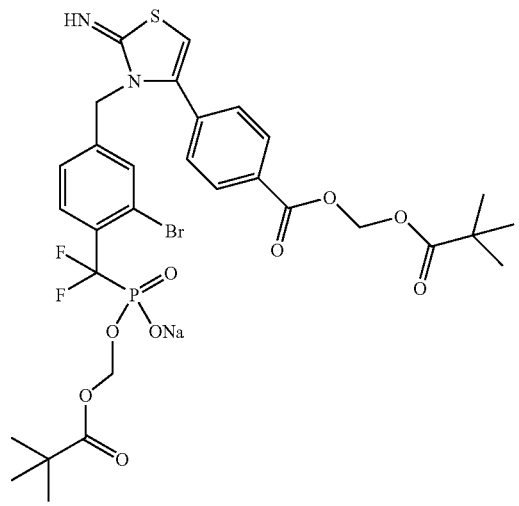

4-{3-[3-Bromo-4-(difluoro-phosphono-methyl)-benzyl]-2-imino-2,3-dihydro-thiazol-4-yl}-benzoic acid (2.00 g, 3.85 mmol), chloromethylpivalate (5.80 g, 38.2 mmol), and diisopropylethylamine (4.98 g, 38.52 mmol) were combined in 15 mL dry DMF. The resulting solution was stirred at 70° C. for 4 h then concentrated in vacuo. The residue was dissolved in 200 mL acetonitrile and 50 mL water and 20 mL saturated aqueous sodium bicarbonate was added. The mixture was concentrated then dissolved in DMSO and loaded onto a 7×13 cm C18-silica column. The column was eluted with 20 to 40% MeCN/H$_2$O. The product-containing fractions eluted around 35% MeCN/H$_2$O. The acetonitrile was removed on a rotary evaporator then the water removed by freeze-drying to give 2.10 g (71%) of a white fluffy solid. $^1$H NMR (DMSO-d$_6$, 600 MHz): δ (ppm) 1.10 (s, 9H), 1.16 (s, 9H), 4.53 (d, J=5.4 Hz, 2H), 5.40 (d, J=10.8 Hz, 2H), 5.96 (s, 2H), 7.35 (s, 1H), 7.39-7.41 (NH cis and trans, 1H), 7.67 (s, 1H), 7.74 (d, J=8.4 Hz, 1H), 7.96 (d, J=8.4 Hz, 2H), 7.99 (d, J=8.4 Hz, 2H), 8.33 (t, J=5.4 Hz, 1H); MS (ESI): m/z 747 (M-H)$^-$.

EXAMPLE 54

4-{3-[3-Bromo-4-(difluoro-phosphono-methyl)-benzyl]-2-imino-2,3-dihydro-thiazol-4-yl}-benzoic acid 2,2-dimethyl-propionyloxymethyl ester bis-sodium salt

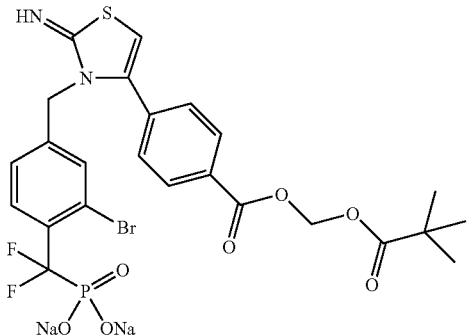

The title compound was isolated as a minor byproduct in the synthesis of the compound of Example 55. Off-white fluffy solid 180 mg (7%). MS (ESI): m/z 632 (M-H)$^-$.

EXAMPLE 55

4-[3-(3-Bromo-4-{[(2,2-dimethyl-propionyloxymethoxy)-hydroxy-phosphoryl]-difluoro-methyl}-benzyl)-2-imino-2,3-dihydro-thiazol-4-yl]-benzoic acid bis-sodium salt

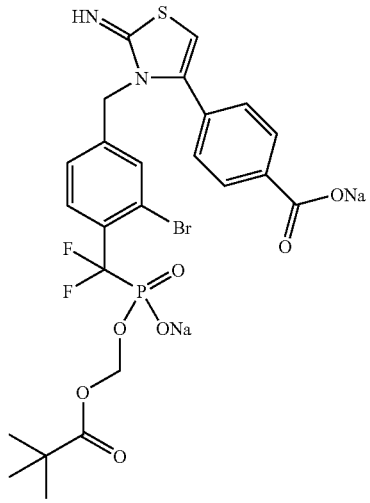

4-[3-(3-Bromo-4-{[(2,2-dimethyl-propionyloxymethoxy)-hydroxy-phosphoryl]-difluoro-methyl}-benzyl)-2-imino-2,3-dihydro-thiazol-4-yl]-benzoic acid 2,2-dimethyl-propionyloxymethyl ester sodium salt (100 mg, 0.13 mmol) was dissolved in 10 mL water. 10 mL rat plasma (RPED 04003 rat plasma from Biochemed with EDTA anti-coagulant) was added and the reaction incubated at 37° C. for 50 min. The mixture was poured into 75 mL acetonitrile to precipitate plasma proteins. The resulting suspension was filtered through celite then concentrated in vacuo. The crude product was dissolved in saturated sodium bicarbonate then loaded onto a C18-silica column. The column was eluted with 0 to 10% MeCN/H$_2$O. MeCN was removed on a rotary evaporator and the resulting aqueous solution freeze-dried to give the title compound as a white solid 50 mg (57%). $^1$H NMR (DMSO-d$_6$, 500 MHz): δ (ppm) 1.11 (s, 9H), 4.51 (d, J=6.5 Hz, 2H), 5.41 (d, J$_{P-H}$=11.0 Hz, 2H), 7.06 (s, 1H), 7.40 (d, J=8.0 Hz, 1H), 7.68-7.75 (m, 4H), 7.85 (d, J=8.5 Hz, 2H), 8.21 (t, J=6.0 Hz, 1H); $^{31}$P NMR (DMSO-d$_6$, 202 MHz, no $^1$H nor $^{19}$F decoupling): δ (ppm) –0.3 (tt, J=85.9 Hz, 10.7 Hz); MS (ESI): m/z 632 (M-H)$^-$.

EXAMPLE 56

Assay for PTP-1B Activity

Materials:
EDTA-ethylenediaminetetraacetic acid (Sigma)
HEPES-N-(2-Hydroxyethyl)piperazine-N'-(2-ethanesulfonic acid) (Sigma)
DTT-dithiothreitol (Sigma)
NaCl-sodium chloride
Enzyme: Human recombinant PTP-1B, containing amino acids 1-321, fused to GST enzyme (glutathione S-transferase) purified by affinity chromatography (Huyer et al, 1997, J. Biol. Chem., 272, 843-852).
pNPP: p-Nitrophenyl Phosphate (Calbiochem)
Assay Buffer: 50 mM HEPES (pH 7.4), 100 mM NaCl, 2 mM EDTA, 3 mM DTT
(5×) pNPP substrate: 10 mM pNPP in assay buffer
Enzyme: 1 mg/ml PTP1B (1-321), dilute 1:200 in assay buffer Enzyme Assay PTP-1B
Assay buffer: 50 mM HEPES (pH 7.4), 100 mM NaCl, 2 mM EDTA, 3 mM DTT
Enzyme dilution buffer: 50 mM HEPES (pH 7.4), 100 mM NaCl, 2 mM EDTA, 3 mM DTT
Substrate 198 mM p-Nitrophenyl Phosphate (pNPP) store at 4° C.

The assay was carried out at 30° C. in 96 well plates. The reaction mixture in 60 ul contained 50 mM HEPES (pH 7.4), 100 mM NaCl, 2 mM EDTA, 3 mM DTT, and 2 mM p-Nitrophenyl Phosphate (pNPP). 5 ul of the test compound (inhibitor) dissolved in DMSO or DMSO alone for control was added to each well and the plate was mixed for 2 min. The reaction was initiated by adding 20 ul of diluted PTP1B (5 ng/ul in 50 mM HEPES (pH 7.4), 100 mM NaCl, 2 mM EDTA, 3 mM DTT). After 20 min at 30° C., the enzyme reaction was terminated by adding 100 ul of 2 M K2CO3 to each well. The phosphatase activity was detected by using Victor II plate reader (Wallac) with absorbance detection at 405 nm. All the assays were done at least in duplicate. The initial rate of pNP is plotted against the concentration of inhibitor.

EXAMPLE 57

Cell Based Assays
Antibodies and Chemicals. The antibody against phosphorylated insulin receptor (pIR) and the ELISA kit for detection of pIR were from Biosource (Camarillo, Calif.). Rabbit anti-IR/IGF-1R [pYpY1162/1163] phosphospecific antibody recognizes both the insulin receptor (IR) and the insulin-like growth factor-1 receptor (IGF-1R) phosphorylated at the active site tyrosine residues, 1162 and 1163

(1135 and 1136 for IGF-1R) (pIR/pIGF-1R). The Insulin Receptor [pYpY1162/1163] ELISA kit specifically recognizes IR phosphorylated at tyrosine residues 1162 and 1163 (and does not recognize phosphorylated IGF-1R). HRP-conjugated secondary antibodies were from Cell Signaling Technology (Beverly, Mass.). The ECL detection system was from Amersham (Buckinghamshire, UK), and human insulin was from Invitrogen (Carlsbad, Calif.).

Tissue Culture. FAO rat hepatoma cells were obtained from ECACC (#89042701) and maintained at 37° C. in a 5% $CO_2$ environment in Dulbecco's modified Eagle's medium with high glucose (DMEM-high glucose) (4500 mg/liter) supplemented with 10% FBS and 50 units/ml penicillin, 100 □g/ml streptomycin and 0.292 mg/ml L-glutamine. For assays, cells were seeded in 24-well plates at a density of $2 \times 10^5$ cells/well and maintained until they reached confluency (about 3 days).

IR phosphorylation assays. Cells in 24-well plates were serum starved overnight in DMEM-low glucose (1000 mg/liter) without serum. Just before use, the starvation medium was discarded and replaced with 0.5 ml of DMEM without serum. Cells were treated for 1 hour with indicated concentrations of compounds, followed by stimulation with or without insulin for 15-30 minutes. For Western analysis, the reaction was stopped by discarding the medium and adding 80 μl of boiling SDS sample lysis buffer [62.5 mM Tris-HCl (pH 6.8), 50 mM DTT, 2% w/v SDS, 10% glycerol, 50 mM NaF, 1 mM $Na_3VO_4$, 2 mM pNPP, 20 mM β-glycerol phosphate and 0.1% w/v bromophenol blue]. 20 μl of the lysates were loaded onto 4-20% Tris-Glycine grandient gels (Invitrogen, Carlsbad, Calif.) and the proteins resolved by SDS-PAGE and transferred to nitrocellulose membranes. The membranes were probed for detection of pIR/pIGF-1R and total PTP-1B using the ECL chemiluminescence detection system. The pIR/pIGF-1R signals were scanned (HP scanjet 3570c) and quantified (Scion Image). For ELISA analysis, the medium was discarded and the plates placed onto a dry ice/ethanol bath for 3 minutes to stop the reaction, then placed on ice. The cells were then lysed and processed according to the ELISA instruction kit manuals for detection of pIR and pAkt (Biosource, Camarillo, Calif.)

Since modifications will be apparent to those of skill in the art, it is intended that the invention be limited only by the scope of the appended claims.

What is claimed is:

1. A compound that has formula II:

or a pharmaceutically acceptable salt, ester, enol ether, enol ester, solvate or hydrate thereof, wherein:

D is

E is $CH_2$;
s is 0;
$R^8$ and $R^9$ are H;
$R^{10}$ is halo;
$R^{11}$ is halo;
$R^{12}$ is H;
$R^{13}$ is $CF_2PO_3H_2$;
$R^{14}$ is halo;
$R^{15}$ is H;
$R^{16}$ is NHC(O)COOH or COOH; and
$R^{17}$ is COO-alkyl.

2. The compound of claim 1, wherein D is

E is $CH_2$;
s is 0;
$R^8$ and $R^9$ are H;
$R^{10}$ Cl;
$R^{11}$ is Cl;
$R^{12}$ is H;
$R^{13}$ is $CF_2PO_3H_2$;
$R^{14}$ is Cl or Br;
$R^{15}$ is H;
$R^{16}$ NHC(O)COOH or COOH; and
$R^{17}$ is COOMe.

3. The compound of claim 1, wherein $R^{10}$ is Cl.

4. The compound of claim 1, wherein $R^{11}$ is Cl.

5. The compound of claim 1, wherein $R^{13}$ is $CF_2PO_3H_2$.

6. The compound of claim 1, wherein $R^{14}$ is Br.

7. The compound of claim 1, wherein $R^{15}$ is H.

8. The compound of claim 1, wherein $R^{16}$ is NHC(O)COOH or COOH.

9. The compound of claim 1, wherein $R^{17}$ is COOMe.

10. The compound of claim 1, wherein the compound is:
N-(4-{2-[[3-Bromo-4-(difluoro-phosphono-methyl)-benzyl]-(3 ,4-dichloro-phenyl)-amino]-thiazol-4-yl}-phenyl)-oxalamic acid.

11. The compound of claim 1, wherein $R^8$ is H, $R^9$ is H, $R^{10}$ is Cl, $R^{11}$ is Cl, $R^{12}$ is H, $R^{13}$ is $CF_2PO_3H_2$, $R^{14}$ is Br, $R^{15}$ is H, $R^{16}$ is NHC(O)COOH, $R^{17}$ is COOMe and s is zero (0).

12. A compound that has formula II:

or a pharmaceutically acceptable salt, ester, enol ether, enol ester, solvate or hydrate thereof, wherein:

D is

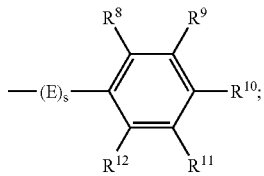

E is CH$_2$;
s is 0;
R$^8$ and R$^9$ are H;
R$^{10}$ is halo;
R$^{11}$ is halo;
R$^{12}$ is H;
R$^{13}$ is CF$_2$PO$_3$H$_2$;
R$^{13}$ is CF$_2$PO$_3$H$_2$;
R$^{14}$ is halo;
R$^{15}$ is H;
R$^{16}$ is NHC(O)COOH; and
R$^{17}$ is H or, COO-alkyl.

13. The compound of claim 12, wherein D is

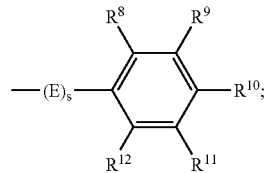

E is CH$_2$;
s is 0;
R$^8$ and R$^9$ are H;
R$^{10}$ is Cl;
R$^{11}$ is Cl;
R$^{12}$ is H;
R$^{13}$ is CF$_2$PO$_3$H$_2$;
R$^{14}$ is Cl or Br;
R$^{15}$ is H;
R$^{16}$ is NHC(O)COOH; and
R$^{17}$ is H or COOMe.

14. The compound of claim 12, wherein R$^{10}$ is Cl.
15. The compound of claim 12, wherein R$^{11}$ is Cl.
16. The compound of claim 12, wherein R$^{14}$ is Br.
17. The compound of claim 12, wherein R$^{17}$ is H or COOMe.
18. The compound of claim 17, wherein R$^{17}$ is H.
19. The compound of claim 17, wherein R$^{17}$ is COOMe.

* * * * *

UNITED STATES PATENT AND TRADEMARK OFFICE
CERTIFICATE OF CORRECTION

PATENT NO.       : 7,381,736 B2
APPLICATION NO.  : 11/219402
DATED            : June 3, 2008
INVENTOR(S)      : Zacharia S. Cheruvallath et al.

It is certified that error appears in the above-identified patent and that said Letters Patent is hereby corrected as shown below:

Column 27,
S24 Structure,

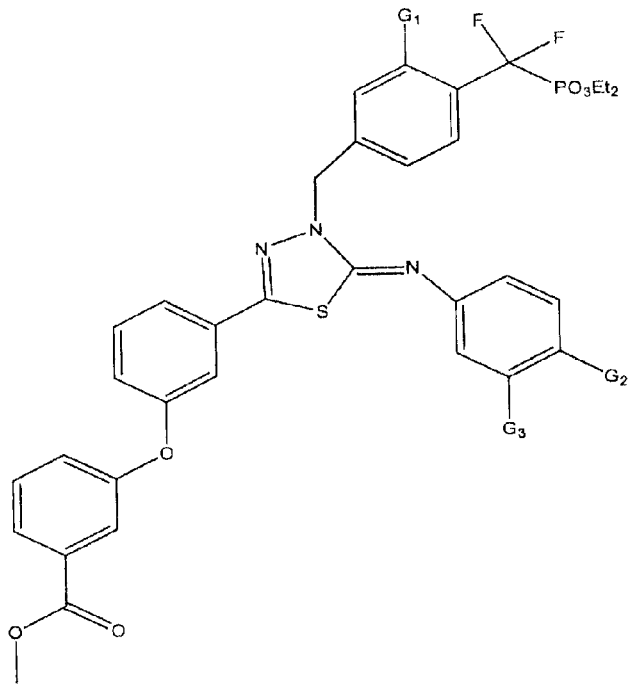

iso-Tdz intermediate
Yields: 10-20%
S24

UNITED STATES PATENT AND TRADEMARK OFFICE
CERTIFICATE OF CORRECTION

PATENT NO.      : 7,381,736 B2
APPLICATION NO. : 11/219402
DATED           : June 3, 2008
INVENTOR(S)     : Zacharia S. Cheruvallath et al.

It is certified that error appears in the above-identified patent and that said Letters Patent is hereby corrected as shown below:

should read

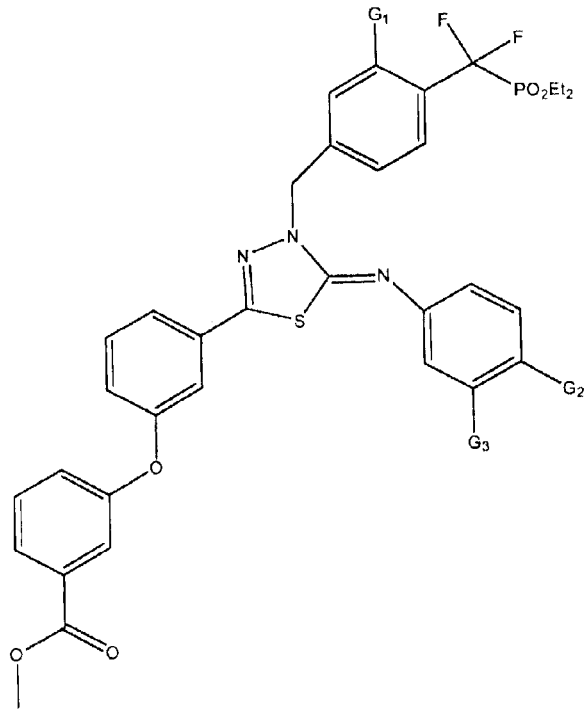

iso-Tdz intermediate
Yields: 10-20%
S24

Column 49,
Line 55, "137 (m, 6 H)" should read --1.37 (m, 6 H)--.

Column 55,
Lines 61-63, "4-(2-{([3-Bromo-4-(difluoro-phosphono-methyl)-benzyl]-naphthalen-1-yl-amino}-thiazol-4-yl)-benzoic acid methyl ester"

UNITED STATES PATENT AND TRADEMARK OFFICE
CERTIFICATE OF CORRECTION

PATENT NO. : 7,381,736 B2
APPLICATION NO. : 11/219402
DATED : June 3, 2008
INVENTOR(S) : Zacharia S. Cheruvallath et al.

It is certified that error appears in the above-identified patent and that said Letters Patent is hereby corrected as shown below:

should read

--4-(2-{[3-Bromo-4-(difluoro-phosphono-methyl)-benzyl]-naphthalen-l-yl-amino}-thiazol-4-yl)-benzoic acid methyl ester--

Signed and Sealed this

Ninth Day of December, 2008

JON W. DUDAS
*Director of the United States Patent and Trademark Office*